(12) United States Patent
Alnemri et al.

(10) Patent No.: US 6,340,740 B1
(45) Date of Patent: Jan. 22, 2002

(54) CASPASE-14, AN APOPTOTIC PROTEASE, NUCLEIC ACIDS ENCODING AND METHODS OF USE

(75) Inventors: Emad S. Alnemri; Teresa Fernandez-Alnemri, both of Ambler, PA (US)

(73) Assignee: THomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/187,789

(22) Filed: Nov. 6, 1998

Related U.S. Application Data

(63) Continuation-in-part of application No. 09/139,600, filed on Aug. 25, 1998.
(60) Provisional application No. 60/056,986, filed on Aug. 26, 1997.

(51) Int. Cl.$^7$ .......................... C07K 1/00; C07K 14/00; C12N 9/00; C12P 21/04
(52) U.S. Cl. .................. 530/350; 530/300; 435/183; 435/69.7
(58) Field of Search .................. 530/350; 435/183, 435/69.7

(56) References Cited

FOREIGN PATENT DOCUMENTS

| | | |
|---|---|---|
| WO | WO 95/24427 | 9/1995 |
| WO | WO 96/13603 | 5/1996 |
| WO | WO 96/25945 | 8/1996 |
| WO | WO 99/10504 | 3/1999 |
| WO | WO 99/23106 | 5/1999 |
| WO | WO 00/04169 | 1/2000 |

OTHER PUBLICATIONS

Ni et al. (Accession No. W47089) GENESEQ Database, Result 1, 1994.*

Cohen, "Caspases: the executioners of apoptosis," *Biochem. J.* 326: 1–16, 1997.

Juan et al., "Identification and Mapping of Casp7, a Cysteine Protease Resembling CPP32β, Interleukin–1β Converting Enzyme, and CED–3," *Genomics 40*: 86–93, 1997.

Marra et al., "The Washu–HHMI Mouse EST Project," *EMBL/Genbank Databases* Accession No. AA103647, Sequence Reference Mmaa3647, 1996.

Marra et al., "The WashuU–HHMI Mouse EST Project," *EMBL/Genbank Databases* Accession No. AA167930, Sequence Reference Mmaa67930, 1996.

Marra et al., "The WashuU–HHMI Mouse EST Project," *EMBL/Genbank Databases* Accession No. AA726845, Sequence Reference Aa726845, 1998.

Piérard et al., "Mutant and Chimeric Recombinant Plaminogen Activators," *The Journal Of Biological Chemistry* 262(24): 11771–11778, 1987.

Van de Craen et al., "Cloning Of Murine Ice Homologues," *European Cytokine Network* 7(2): p. 220, Abstract No. 102, at $6^{th}$ *International Tumor Necrosis Factor Congress* Rhodes, Greece, May 8–12, 1996.

Ahmad et al., "Identification and Characterization of Murine Caspase–14, a New Member of the Caspase Family," *Cancer Research 58*: 5201–5205, 1998.

Hu et al., "Caspase–14 Is a Novel Developmentally Regulated Protease," *The Journal of Biological Chemistry* 273(45): 29648–29653, 1998.

Scaffidi et al., "Flice Is Predominantly Expressed as Two Functionally Active Isoforms, Caspase–8/a and Caspase–8/b," *The Journal of Biological Chemistry* 272(43): 26953–26958, 1997.

Van de Craen et al., "Identification of a New Caspase Homologue: Caspase–14," *Cell Death and Differentiation 5*: 838–846, 1998.

Alnemri et al., "Human ICE/CED–3 Protease Nomenclature," *Cell 87*: 171, 1996.

Barinaga, "Cell Suicide: By ICE, Not Fire," *Science 263*: 754–756, 1994.

Black et al., "Activation of Interleukin–1β by a co–induced protease," *FEBS Letters* 247(2): 386–390, 1989.

Boldin et al., "A Novel Protein That Interacts with the Death Domain of Fas/APO1 Contains a Sequence Motif Related to the Death Domain," *J. Biol. Chem.* 270(14): 7795–7798, 1995.

Boldin et al., "Involvement of MACH, a Novel MORT1/FADD–Interacting Protease, in Fas/APO–1– and TNF Receptor–Induced Cell Death," *Cell 85*: 803–815, 1996.

Cerretti et al., "Molecular Cloning of the Interleukin–1β Converting Enzyme," *Science 256*: 97–100, 1992.

(List continued on next page.)

*Primary Examiner*—Susan Ungar
*Assistant Examiner*—Gary B. Nickol
(74) *Attorney, Agent, or Firm*—Seed Intellectual Property Law Group PLLC

(57) ABSTRACT

The invention relates to an isolated nucleic acid molecule encoding a caspase-14 polypeptide or functional fragment thereof, a vector that contains the nucleic acid molecule and a host cell that contains the vector. The invention also relates to an isolated gene encoding caspase-14, as well as functional fragments thereof. The gene or nucleic acid molecule can include single or double stranded nucleic acids corresponding to coding or non-coding strands of the caspase-14 nucleotide sequence. Isolated caspase-14 polypeptides or functional fragments thereof are also provided, as are antibodies that specifically bind thereto. In addition, the invention relates to methods of identifying compounds that modulate caspase-14 activity.

11 Claims, 15 Drawing Sheets

OTHER PUBLICATIONS

Chinnaiyan et al., "FADD, a Novel Death Domain–Containing Protein Interacts with the Death Domain of Fas and Initiates Apoptosis," *Cell 81*: 505–512, 1995.

Duan et al., "ICE–LAP3, a Novel Mammalian Homologue of the *Caenorhabditis elegans* Cell Death Protein Ced–3 Is Activated during Fas– and Tumor Necrosis Factor–induced Apoptosis," *J. Biol. Chem. 271*(3): 1621–1625, 1996.

Duan et al., "ICE–LAP6, a novel member of the ICE/Ced–3 Gene Family, Is Activated By the Cytotoxic T Cell Protease Granzyme," *J. Biol. Chem. 271*: 16720–16724, 1996.

Enari et al., "Involvement of an ICE–like protease in Fas––mediated apoptosis," *Nature 375*: 78–81, 1995.

Faucheu et al., "Identification of a cysteine protease closely related to interleukin–1β–converting enzyme," *Eur. J. Biochem. 236*: 207–213, 1996.

Fernandes–Alnemri et al., "CPP32, a Novel Human Apoptotic Protein with Homology to *Caenorhabditis elegans* Cell Death Protein Ced–3 and Mammalian Interleukin–1β–converting Enzyme," *J. Biol. Chem. 269*(49): 30761–30764, 1994.

Fernandes–Alnemri et al., "In Vitro Activation of CPP32 and Mch3 by Mch4, a novel human apoptotic cysteine protease containing two FADD–like domains," *Proc. Natl. Acad. Sci. USA 93*: 7464–7469, 1996.

Fernandes–Alnemri et al., "Mch3, A Novel Human Apoptotic Cysteine Protease Highly Related to CPP32," *Cancer Research 55*(24): 6045–6052, 1995.

Gagliardini et al., "Prevention of Vertebrate Neruonal Death by the crmA Gene," *Science 263*: 826–828, 1994.

Hillier et al., "The WashU–Merck EST Project," *EMBL/Genbank Databases*, Accession No. T96912, Sequence Reference HS91272, 1995; http://www.ncbi.clm.cih.gov/htbin–post/Entrez/query?uid=735536&form=6&db=n&Dopt=g. [Accessed Jan. 21, 1999].

Hillier et al., "The WashU–Merck EST Project," *EMBL/Genbank Databases*, Accession No. N42544, Sequence Reference HS544281, 1996; http://www.ncbi.nlm.nih.gov/ht-bin–post/Entrez/query?uid=1166974&form=6&db=n&Dopt=g. [Accessed Jan. 21, 1999].

Howard et al., "IL–1–Converting Enzyme Requires Aspartic Acid Residues for Processing of the IL–1β Precursor at Two Distinct Sites and Does Not Cleave 31–kDa IL–1α," *J. Immunol. 147*(9): 2964–2969, 1991.

Hsu et al., "TRADD–TRAF2 and TRADD–FADD Interactions Define Two Distinct TNF Receptor 1 Signal Transduction Pathways," *Cell 84*: 299–308, 1996.

Humke et al., "ERICE, A Novel FLICE–activatable Caspase," *J. Biol. Chem. 273*(25): 15702–15707, 1998.

Kischkel et al., "Cytotoxicity–dependent APO–1 (Fas/CD95)–associated proteins form a death–inducing signaling complex (DISC) with the receptor," *The EMBO Journal 14*(22): 5579–5588, 1995.

Korsmeyer, "Regulators of cell death," *TIG 11*(3): 101–105, 1995.

Kostura et al., "Identification of a monocyte specific pre-interleukin 1β convertase activity," *Proc. Natl. Acad. Sci. USA 86*: 5227–5231, 1989.

Kumar et al., "Induction of apoptosis by the mouse Nedd2gene, which encodes a protein similar to the product of the *Caenorhabditis elegans* cell death gene ced–3 and the mammalian IL–1β–converting enzyme," *Genes Dev. 8*: 1613–1626, 1994.

Lippke et al., "Identification and Characterization of CPP32/Mch2 Homolog 1, a Novel Cysteine Protease Similar to CPP32," *J. Biol. Chem. 271*(4): 1825–1828, 1996.

Los et al., "Requirements of an ICE/CED–3 protease for Fas/APO–1–mediated apoptosis," *Nature 375*: 81–83, 1995.

Mann and Wilm, "Electrospray mass spectrometry for protein characterization," *TIBS 20*: 219–224, 1995.

Miura et al., "Induction of Apoptosis in Fibroblasts by IL–1β–Converting Enzyme, a Mammalian Homolog of the *C. elegans* Cell Death Gene ced–3," *Cell 75*: 653–660, 1993.

Muzio et al., "FLICE, A Novel FADD–Homologous ICE/CED–3–like Protease, Is Recruited to the CD95 (Fas/APO–1) Death–Inducing Signaling Complex," *Cell 85*: 817–827, 1996.

Nagata and Golstein, "The Fas Death Factor," *Science 267*: 1449–1456, 1995.

Nagata, "Apoptosis by Death Factor," *Cell 88*: 355–365, 1997.

Nicholson et al., "Identification and inhibition of the ICE/CED–3 protease necessary for mammalian apoptosis," *Nature 376*: 37–43, 1995.

Ray et al., "Viral Inhibition of Inflammation: Cowpox Virus Encodes an Inhibitor of the Interleukin–1β Converting Enzyme," *Cell 69*: 597–604, 1992.

Reed, "Mini–Review: Cellular Mechanisms of Disease Series: Bcl–2 and the Regulation of Programmed Cell Death," *J. Cell Biol. 124*(1 & 2): 1–6, 1994.

Sakamaki et al., "Molecular cloning and characterization of mouse caspase–8," *Eur. J. Biochem. 253*(2): 399–405, 1998.

Salvesen and Dixit, "Caspases: Intracellular Signaling by Proteolysis," *Cell 91*: 443–446, 1997.

Sleath et al., "Substrate Specificity of the Protease That Processes Human Interleukin–1β," *J. Biol. Chem. 265*(24): 14526–14528, 1990.

Srinivasula et al., "Autoactivation of Procaspase–9 by Apaf–1–Mediated Oligomerization," *Mol. Cell. 1*: 949–957, 1998.

Srinivasula et al., "Generation of Constitutively Active Recombinant Caspases–3 and –6 by Rearrangement of Their Subunits," *J. Biol. Chem. 273*(17): 10107–10111, 1998.

Srinivasula et al., "The Ced–3/Interleukin 1β Converting Enzyme–like Homolog Mch6 and the Lamin–cleaving Enzyme Mch2α Are Substrates for the Apoptotic Mediator CPP32," *J. Biol. Chem. 271*(43): 27099–27106, 1996.

Steller, "Mechanisms and Genes of Cellular Suicide," *Science 267*: 1445–1449, 1995.

Tewari et al., "Yama/CPP32β, a Mammalian Homolog of CED–3, Is a CrmA–Inhibitable Protease That Cleaves the Death Substrate Poly(ADP–Ribose) Polymerase," *Cell 81*: 801–809, 1995.

Thompson, "Apoptosis in the Pathogenesis and Treatment of Disease," *Science 267*: 1456–1462, 1995.

Thornberry et al., "A novel heterodimeric cysteine protease is required for interleukin–1β processing in monocytes," *Nature 356*: 768–774, 1992.

Van de Craen et al., "Characerization of seven murine caspase family members," *FEBS Letters 403*: 61–69, 1997.

Walker et al., "Crystal Structure of the Cysteine Protease Interleukin–1β–Converting Enzyme: A(p20/p10)$_2$ Homodimer," *Cell 78*: 343–352, 1994.

Wang et al., "Ich–1, an Ice/ced–3–Related Gene, Encodes Both Positive and Negative Regulators of Programmed Cell Death," *Cell 78*: 739–750, 1994.

Williams and Smith, "Molecular Regulation of Apoptosis: Genetic Controls on Cell Death," *Cell 74*: 777–779, 1993.

Wilm et al., "Femtomole sequencing of proteins from polyacrylamide gels by nano–electrospray mass spectrometry," *Nature 379*: 466–469, 1996.

Wilson et al., "Structure and mechanism of interleukin–1β converting enzyme," *Nature 370*: 270–275, 1994.

Yuan et al., "The *C. elegans* Cell Death Gene ced–3 Encodes a Protein Similar to Mammalian Interleukin–1β–Converting Enzyme," *Cell 75*: 641–652, 1993.

\* cited by examiner

```
      CACGCGTCCGCCCACGCGTCCGGTGAGACAGAGGCAAAACAAAGGTGCTGAAAGCCAGAC
   1  ----------+---------+---------+---------+---------+---------+  60
      GTGCGCAGGCGGGTGCGCAGGCCACTCTGTCTCCGTTTTGTTTCCACGACTTTCGGTCTG a     H  A  S  A  H  A  S  G  E  T  E  A  K  Q  R  C  *  K  P  D  -

ATGGAGTCAGAGATGAGTGATCCTCAGCCATTGCAGGAGGAAAGATATGATATGTCAGGT
  61  ----------+---------+---------+---------+---------+---------+ 120
      TACCTCAGTCTCTACTCACTAGGAGTCGGTAACGTCCTCCTTTCTATACTATACAGTCCA a     M  E  S  E  M  S  D  P  Q  P  L  Q  E  E  R  Y  D  M  S  G  -

GCCCGCCTGGCCCTGACGCTGTGTGTCACCAAAGCCCGGGAGGGTTCCGAGGTAgACATG
 121  ----------+---------+---------+---------+---------+---------+ 180
      CGGGCGGACCGGGACTGCGACACACAGTGGTTTCGGGCCCTCCCAAGGCTCCATcTGTAC a     A  R  L  A  L  T  L  C  V  T  K  A  R  E  G  S  E  V  D  M  -

GAGGCCCTGGAACGCATGTTCCGTTACCTGAAATTTGAAAGCACCATGAAGAGGGATCCC
 181  ----------+---------+---------+---------+---------+---------+ 240
      CTCCGGGACCTTGCGTACAAGGCAATGGACTTTAAACTTTCGTGGTACTTCTCCCTAGGG a     E  A  L  E  R  M  F  R  Y  L  K  F  E  S  T  M  K  R  D  P  -

ACCGCCCAGCAATTTCTGGAAGAGTTGGATGAATTTCAGCAGACCATAGATAATTGGGAA
 241  ----------+---------+---------+---------+---------+---------+ 300
      TGGCGGGTCGTTAAAGACCTTCTCAACCTACTTAAAGTCGTCTGGTATCTATTAACCCTT a     T  A  Q  Q  F  L  E  E  L  D  E  F  Q  Q  T  I  D  N  W  E  -

GAGCCTGTCAGCTGTGCCTTTGTGGTACTCATGGCACATGGTGAGGAAGGCCTCCTCAAG
 301  ----------+---------+---------+---------+---------+---------- 360
      CTCGGACAGTCGACACGGAAACACCATGAGTACCGTGTACCACTCCTTCCGGAGGAGTTC a     E  P  V  S  C  A  F  V  V  L  M  A  H  G  E  E  G  L  L  K  -

GGAGAAGATGAGAAGATGGTCAGACTAGAAGACCTTTTTGAAGTCTTGAACAACAAGAAC
 361  ----------+---------+---------+---------+---------+---------- 420
      CCTCTTCTACTCTTCTACCAGTCTGATCTTCTGGAAAAACTTCAGAACTTGTTGTTCTTG a     G  E  D  E  K  M  V  R  L  E  D  L  F  E  V  L  N  N  K  N  -

TGCAAGGCCCTGAGAGGCAAGCCAAAGGTGTACATCATCCAGGCTTGTAGAGGAGAGCAC
 421  ----------+---------+---------+---------+---------+---------- 480
      ACGTTCCGGGACTCTCCGTTCGGTTTCCACATGTAGTAGGTCCGAACATCTCCTCTCGTG
```

AGAGACCCCGGTGAGGAACTACGTGGAAATGAGGAACTAGGTGGAGATGAGGAACTNGGT
481  ---------+---------+---------+---------+---------+---------+ 540
     TCTCTGGGGCCACTCCTTGATGCACCTTTACTCCTTGATCCACCTCTACTCCTTGANCCA a    R  D  P  G  E  E  L  R  G  N  E  E  L  G  G  D  E  E  L  G  -

GGAGATGAGGTTGCTGTGCTCAAGAACAACCCCCAAAGTATCCCAACCTATACGGATACC
541  ---------+---------+---------+---------+---------+---------+ 600
     CCTCTACTCCAACGACACGAGTTCTTGTTGGGGGTTTCATAGGGTTGGATATGCCTATGG a    G  D  E  V  A  V  L  K  N  N  P  Q  S  I  P  T  Y  T  D  T  -

CTCCACATCTACTCCACGGTAGAGGGGTACCTCTCCTATAGACATGACGAGAAAGGCTCT
601  ---------+---------+---------+---------+---------+---------+ 660
     GAGGTGTAGATGAGGTGCCATCTCCCCATGGAGAGGATATCTGTACTGCTCTTTCCGAGA a      L  H  I  Y  S  T  V  E  G  Y  L  S  Y  R  H  D  E  K  G  S  -

GGCTTCATCCAGACCCTGACGGATGTGTTCATTCATAAAAAAGGATCCATCTTAGAACTG
661  ---------+---------+---------+---------+---------+---------+ 720
     CCGAAGTAGGTCTGGGACTGCCTACACAAGTAAGTATTTTTTCCTAGGTAGAATCTTGAC a      G  F  I  Q  T  L  T  D  V  F  I  H  K  K  G  S  I  L  E  L  -

ACAGAAGAGATCACCCGACTTATGGCAAACACGGAGGTGATGCAGGAAGGAAAACCAAGG
721  ---------+---------+---------+---------+---------+---------+ 780
     TGTCTTCTCTAGTGGGCTGAATACCGTTTGTGCCTCCACTACGTCCTTCCTTTTGGTTCC a    T  E  E  I  T  R  L  M  A  N  T  E  V  M  Q  E  G  K  P  R  -

AAAGTGAACCCTGAAGTCCAAAGCACCCTCCGGAAGAAGCTCTATTTGCAATAAAAGAGA
781  ---------+---------+---------+---------+---------+---------+ 840
     TTTCACTTGGGACTTCAGGTTTCGTGGGAGGCCTTCTTCGAGATAAACGTTATTTTCTCT a    K  V  N  P  E  V  Q  S  T  L  R  K  K  L  Y  L  Q  *  K  R  -

GGGCAGGGAT
841  ---------+ 850
     CCCGTCCCTA a    G  Q  G   -
```

Fig. 1B

Inventor(s): Emad S. Alnemri et al.   Serial No. 09/187,789   Docket No. 480140.434C1

```
casp-11  ----------------------------------------------------------------------------------
casp-12  --------------------------------------------------------MAARRTHERDPIYKIKGLAKDMLDGV    26
casp-1   ---------------------------------------------------------MADKILRAKRKQFINSVSIGTINGL    25
casp-3   ----------------------------------------------------------------------------------
casp-7   ----------------------------------------------------------------------------------
casp-6   ----------------------------------------------------------------------------------
casp-8   MDFQSCLDAIAEELGSEDLAALKFLCLDYIPHKKLETIEDAQKLFLRLREKGMLEEGNLSFLKELLFHISRWDLLVNFLDCNREEMVRELRDPRQCPRFL   100
casp-2   -----------------------------MAAPSGRSQSSLHRKGLMAADRRSRILAVCGMHPDHQETLKKNRVVLAKQLL    52
casp-14  ---------------------------------------------------------------------------------- casp-11  ---------------MAENKHPDKPLKVLEQLGKEVL..TEYLEKLVQSNVLKLKEEDKQKFNNAERSDKRWVFV.DAMKKKHSKVGEMLLQTFFSVDPG    82
casp-12  FDDLVEKNVLNGDELLKIGESASFILNKAENLVENFLEKTDMAGKIFAGHIANSQEQLSLQFSNDEDDGPQKICTPSSPSESKRKVEDDEMEVNAGLAHE   126
casp-1   LDELLEKRVLNQEEMDKIKLANITAMDKARDLCDHVSKKGPQASQIFITYICNEDCYLAGILELQSAPSAETFVATEDSKGGHPSSSETKEEQN..KEDG   123
casp-3   -------------------------------------------------------------------------MENNKTSV    8
casp-7   --------------------------------------------------------MTDDQDCAAELEKVDSSSEDGVDAKPDRSSI    31
casp-6   ----------------------------------------------------------------------------------
casp-8   PYRSCSFRLSEEVSELELRSFKFLLNNEIPKCKLEDDLSLLEIFVEMEKRTMLAENNLETLKSICDQVNKSLLGKIEDYERSSTERRMSLEGREELPPSV   200
casp-2   LSELLEHLLEKDIITLEMRELIQAKGGSFSQNVELLNLLPKRGPQAFDAFCEALRETRQGHLEDLLLTTLSDIQHVLPPLSCDYDTSLPFSVCESCPPHK   152
casp-14  ---------------------------------------------------------------------------------- casp-11  SHHGEANLEMEEPEESLNTLKLCSPEEFTRLCREKTQEIYPIKEAN.GRTRKALIICNTEFKHLSLRYGANFDIIGMKGLLEDLGYDVVVKEELTAEGME   181
casp-12  SHLMLTAPHGLQSSEVQDTLKLCPRDQFCKIKTERAKEIYPVMEKE.GRTRLALIICNKKFDYLFDRDNADTDILNMQELLENLGYSVVLKENLTAQEME   225
casp-1   TFPGLTG..........TLKFCPLEKAQKLWKENPSEIYPIMNTT.TRTRLALIICNTEFQHLSPRVGAQVDLREMKLLLEDLGYTVKVKENLTALEMV   211
casp-3   DSKSINNFEVKTIHGSKSVDSGIYLDSSYKMDYPEMGICIIINNKNFHKS..........TGMSSRSGTDVDAANLRETFMGLKYCVRNKNDLTREDIL    97
casp-7   ISSILLKKKRNASAGPVRTGRDRVPTYLYRMDFQKMGKCIIINNKNFDKA..........TGMDVRNGTDKDAGALFKCFQNLGFEVTVHNDCSCAKMQ   120
casp-6   ---------MTETDGFYKSREVFDPAEQYKMDHKRRGVALIFNHERFFWH..........LTLPERRGTNADRDNLTRRFSDLGFEVKCFNDLRAEELL    80
casp-8   LDEMSLKMAELCDSPREQDSESRTSDKVYQMKNKPRGYCLIINNHDFSKA....REDITQLRKMKDRKGTDCDKEALSKTFKELHFEIVSYDDCTANEIH   296
casp-2   QLRLSTDATEHSLDNGDGPPCLLVKPCTPEFYQAHYQLAYRLQSQPRGLALVLSNVHFTGEKDLEFRSGGDVDHTTLVTLFKLLGYNVHVLHDQTAQEMQ   252
casp-14  ------------------------------MESEMSDPQPLQEERYDMSGARLALTLCVTK...AREGSEVDMEALERMFRYLKFESTMKRDPTAQQFL    66 casp-11  SEMDKFAAL..SEHQTSDSTFLVLMSHGTLHGICGTMHSEKTPDVLQYDTIYQIFNNCHCPGLRDKPKVIIVQACRGGNSGEMWIRESSKPQLCRGVDLP   279
casp-12  TELMQFAGR..PEHQSSDSTFLVFMSHGILEGICGVKHRNKKPDVLHDDTIFKIFNNSNCRSLRNKPKILIMQACRGRYNGTIWV.STNKGIATADTDEE   322
casp-1   KEVKEFAAC..PEHKTSDSTFLVFMSHGIQEGICGTTYSNEVSDILKVDTIFQMMNTLKCPSLKDKPKVIIIQACRGEKQGVVLLKDS.....VRDSEED   304
casp-3   ELMDSVSK...EDHSKRSSFVCVILSHGDEGVIYGTNGP......VELKKLTSFFRGDYCRSLTGKPKLFIIQACRGTELDCGI........ETDS...G   177
casp-7   DLLRKASE...EDHSNSACFACVLLSHGEEDLIYGKDGV......TPIKDLTAHFRGDRCKTLLEKPKLFFIQACRGTELDDGI........QADS...G   200
casp-6   LKIHEVST...SSHIDADCFICVFLSHGEGNHVYAYDAK......IEIQTLTGLFKGDKCQSLVGKPKIFIIQACRGSQHDVPVVPLDMVDHQTDK..LD   169
casp-8   EILEGYQS...ADHKNKDCFICCILSHGDKGVVYGTDGK.....EASIYDLTSYFTGSKCPSLSGKPKIFFIQACRGSNFQKGVPDEAGFEQQNHT..LE   356
casp-2   EKLQNFAQ.LPAHRVTDSVC.VALLSHGVEGGIYGVDGK.....LLQLQEVFRLFDNANCPSLQNKPKMFFIQACRGDETDRGVDQQDGKNHTQSPGCEE   345
casp-14  EELDEFQQTIDNWEEPVSCAFVVLMAHGEEGLLKGEDEK......MVRLEDLFEVLNNKNCKALRGKPKVYIIQACRGEHRDPGEELRGNEELGGDEELGG   161
```

*Fig. 2A-1*

```
casp-11  RNMEA....DAVKLSHVEKDFIAFYSTTPHHLSYRDKTGGSYFITRLISCFRKHACSCHLFDIFLKVQQSFEKASIHSQMPTIDRATLTRYFYLFPGN--  373
casp-12  RVLSCKW.NNSITKAHVETDFIAFKSSTPHNISWRVGKTGSLFISKLIDCFKKYCWCYHLEEIFRKVQHSFEVPGELTQMPTIERVSMTRYFYLFPGN--  419
casp-1   FLTDAIFEDDGIKKAHIEKDFIAFCSSTPDNVSWRHPVRGSLFIESLIKHMKEYAWSCDLEDIFRKVRFSFEQPEFRLQMPTADRVTLTKRFYLFPGH--  402
casp-3   ..TDEEMAC...QKIPVEADFLYAYSTAPGYYSWRNSKDGSWFIQSLCSMLKLY..AHKLEFMHILTRVNRKVATEFESFSLDSTFHAKKQIPCIVSMLT  270
casp-7   ..PINDIDANPRNKIPVEADFLFAYSTVPGYYSWRNPGKGSWFVQALCSILNEH..GKDLEIMQILTRVNDRVARHFESQSDDPRFNEKKQIPCMVSMLT  296
casp-6   ..NVTQVDAASVYTLPAGADFLMCYSVAEGYYSHRETVNGSWYIQDLCEMLARY..GSSLEFTELLTLVNRKVSQRRVDFCKDPDAIGKKQVPCFASMLT  265
casp-8   ..VDS...SSHKNYIPDEADFLLGMATVLMCVSYRDPVNGTWYIQSLCQSLRERC.PQGDDILSILTGVNYDVSN......KDDRRNKGKQMPQPTFTLR  474
casp-2   ..SDAGKEELMKMRLPTRSDMICGYACLKGNAAMRNTKRGSWYIEALTQVFSERA.C.DMHVADMLVKVNALIKER.EGYAPGTEFHRCKEMSEYCSTLC  440
casp-14  ..DEVAVLKNNPQSIPTYTDTLHIYSTVEGYLSYRHDEKGSGFIQTLTDVFIHKK.G.S..ILELTEEITRLMANT.EVMQEGKP...RKVNPEVQSTLR  251 casp-11  ------------
casp-12  ------------
casp-1   ------------
casp-3   KELYFYH-----  277
casp-7   KELYFSR-----  303
casp-6   KKLHFCPKPSK-  276
casp-8   KKL---------  477
casp-2   QQLYLFPGYPPT  452
casp-14  KKLYLQ------  257
```

Fig. 2A-2

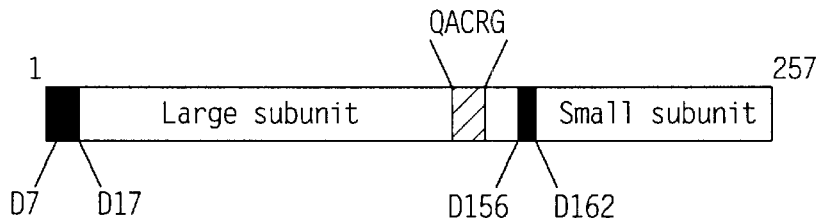

Fig. 2B

```
aggatcagac aagggtgctg agagccggga ctcacaacca aaggagaa atg agc aat    57
                                                    Met Ser Asn
                                                     1 ccg cgg tct ttg gaa gag gag aaa tat gat atg tca ggt gcc cgc ctg   105
Pro Arg Ser Leu Glu Glu Glu Lys Tyr Asp Met Ser Gly Ala Arg Leu
      5              10                  15 gcc cta ata ctg tgt gtc acc aaa gcc cgg gaa ggt tcc gaa gaa gac   153
Ala Leu Ile Leu Cys Val Thr Lys Ala Arg Glu Gly Ser Glu Glu Asp
 20              25                  30                  35 ctg gat gct ctg gaa cac atg ttt cgg cag ctg aga ttc gaa agc acc   201
Leu Asp Ala Leu Glu His Met Phe Arg Gln Leu Arg Phe Glu Ser Thr
                 40                  45                  50 atg aaa aga gac ccc act gcc gag caa ttc cag gaa gag ctg gaa aaa   249
Met Lys Arg Asp Pro Thr Ala Glu Gln Phe Gln Glu Glu Leu Glu Lys
             55                  60                  65 ttc cag cag gcc atc gat tcc cgg gaa gat ccc gtc agt tgt gcc ttc   297
Phe Gln Gln Ala Ile Asp Ser Arg Glu Asp Pro Val Ser Cys Ala Phe
                 70                  75                  80 gtg gta ctc atg gct cac ggg agg gaa ggc ttc ctc aag gga gaa gat   345
Val Val Leu Met Ala His Gly Arg Glu Gly Phe Leu Lys Gly Glu Asp
         85                  90                  95 ggg gag atg gtc aag ctg gag aat ctc ttc gag gcc ctg aac aac aag   393
Gly Glu Met Val Lys Leu Glu Asn Leu Phe Glu Ala Leu Asn Asn Lys
100                 105                 110                 115 aac tgc cag gcc ctg cga gct aag ccc aag gtg tac atc ata cag gcc   441
Asn Cys Gln Ala Leu Arg Ala Lys Pro Lys Val Tyr Ile Ile Gln Ala
                120                 125                 130 tgt cga gga gaa caa agg gac ccc ggt gaa aca gta ggt gga gat gag   489
Cys Arg Gly Glu Gln Arg Asp Pro Gly Glu Thr Val Gly Gly Asp Glu
            135                 140                 145 att gtg atg gtc atc aaa gac agc cca caa acc atc cca aca tac aca   537
Ile Val Met Val Ile Lys Asp Ser Pro Gln Thr Ile Pro Thr Tyr Thr
        150                 155                 160
```

*Fig. 7A*

```
gat gcc ttg cac gtt tat tcc acg gta gag gga tac atc gcc tac cga   585
Asp Ala Leu His Val Tyr Ser Thr Val Glu Gly Tyr Ile Ala Tyr Arg
    165                 170                 175 cat gat cag aaa ggc tca tgc ttt atc cag acc ctg gtg gat gtg ttc   633
His Asp Gln Lys Gly Ser Cys Phe Ile Gln Thr Leu Val Asp Val Phe
180                 185                 190                 195 acg aag agg aaa gga cat atc ttg gaa ctt ctg aca gag gtg acc cgg   681
Thr Lys Arg Lys Gly His Ile Leu Glu Leu Leu Thr Glu Val Thr Arg
                200                 205                 210 cgg atg gca gaa gca gag ctg gtt caa gaa gga aaa gca agg aaa acg   729
Arg Met Ala Glu Ala Glu Leu Val Gln Glu Gly Lys Ala Arg Lys Thr
            215                 220                 225 aac cct gaa atc caa agc acc ctc cgg aaa cgg ctg tat ctg cag tag   777
Asn Pro Glu Ile Gln Ser Thr Leu Arg Lys Arg Leu Tyr Leu Gln
        230                 235                 240
```

*Fig. 7B*

```
aggatcagac aagggtgctg agagccggga ctcacaacca aaggagaa atg agc aat    57
                                                     Met Ser Asn
                                                       1 ccg cgg tct ttg gaa gag gag aaa tat gat atg tca ggt gcc cgc ctg   105
Pro Arg Ser Leu Glu Glu Glu Lys Tyr Asp Met Ser Gly Ala Arg Leu
      5               10                  15 gcc cta ata ctg tgt gtc acc aaa gcc cgg gaa ggt tcc gaa gaa gac   153
Ala Leu Ile Leu Cys Val Thr Lys Ala Arg Glu Gly Ser Glu Glu Asp
 20              25                  30                  35 ctg gat gct ctg gaa cac atg ttt cgg cag ctg aga ttc gaa agc acc   201
Leu Asp Ala Leu Glu His Met Phe Arg Gln Leu Arg Phe Glu Ser Thr
                 40                  45                  50 atg aaa aga gac ccc act gcc gag caa ttc cag gaa gag ctg gaa aaa   249
Met Lys Arg Asp Pro Thr Ala Glu Gln Phe Gln Glu Glu Leu Glu Lys
             55                  60                  65 ttc cag cag gcc atc gat tcc cgg gaa gat ccc gtc agt tgt gcc ttc   297
Phe Gln Gln Ala Ile Asp Ser Arg Glu Asp Pro Val Ser Cys Ala Phe
                 70                  75                  80 gtg gta ctc atg gct cac ggg agg gaa ggc ttc ctc aag gga gaa gat   345
Val Val Leu Met Ala His Gly Arg Glu Gly Phe Leu Lys Gly Glu Asp
         85                  90                  95 ggg gag atg gtc aag ctg gag aat ctc ttc gag gcc ctg aac aac aag   393
Gly Glu Met Val Lys Leu Glu Asn Leu Phe Glu Ala Leu Asn Asn Lys
100                 105                 110                 115 aac tgc cag gcc ctg cga gct aag ccc aag gtg tac atc ata cag gcc   441
Asn Cys Gln Ala Leu Arg Ala Lys Pro Lys Val Tyr Ile Ile Gln Ala
                 120                 125                 130 tgt cga gga gaa caa agg gac ccc ggt gaa aca gta ggt gga gat gag   489
Cys Arg Gly Glu Gln Arg Asp Pro Gly Glu Thr Val Gly Gly Asp Glu
             135                 140                 145 att gtg atg gtc atc aaa gac agc cca caa acc atc cca aca tac aca   537
Ile Val Met Val Ile Lys Asp Ser Pro Gln Thr Ile Pro Thr Tyr Thr
                150                 155                 160
```

*Fig. 8A*

```
gat gcc ttg cac gtt tat tcc acg gta gag gga ccc acg ccc ttc cag    585
Asp Ala Leu His Val Tyr Ser Thr Val Glu Gly Pro Thr Pro Phe Gln
    165                 170                 175 gat ccc ctc tac cta ccc tct gaa gct ccc ccg aac cca cct ctc tgg    633
Asp Pro Leu Tyr Leu Pro Ser Glu Ala Pro Pro Asn Pro Pro Leu Trp
180                 185                 190                 195 aat tcc cag gat aca tcg cct acc gac atg atc aga aag gct cat gct    681
Asn Ser Gln Asp Thr Ser Pro Thr Asp Met Ile Arg Lys Ala His Ala
                200                 205                 210 tta tcc aga ccc tgg tgg atg tgt tca cga aga gga aag gac ata tct    729
Leu Ser Arg Pro Trp Trp Met Cys Ser Arg Arg Gly Lys Asp Ile Ser
                215                 220                 225 tgg aac ttc tgacagaggt gacccggcgg atggcagaag cagagctggt            778
Trp Asn Phe
        230 tcaagaagga aaagcaagga aaacgaaccc tgaaatccaa agcaccctcc ggaaacggct  838 gtatctgcag tag                                                     851
```

*Fig. 8B* aggatcagac aagggtgctg agagccggga ctcacaacca aaggagaa atg agc aat   57
                                                        Met Ser Asn
                                                         1 ccg cgg tct ttg gaa gag gag aaa tat gat atg tca ggt gcc cgc ctg  105
Pro Arg Ser Leu Glu Glu Glu Lys Tyr Asp Met Ser Gly Ala Arg Leu
     5              10                  15 gcc cta ata ctg tgt gtc acc aaa gcc cgg gaa ggt tcc gaa gaa gaa  153
Ala Leu Ile Leu Cys Val Thr Lys Ala Arg Glu Gly Ser Glu Glu Glu
 20              25                  30                  35 gag ctg gaa aaa ttc cag cag gcc atc gat tcc cgg gaa gat ccc gtc  201
Glu Leu Glu Lys Phe Gln Gln Ala Ile Asp Ser Arg Glu Asp Pro Val
             40                  45                  50 agt tgt gcc ttc gtg gta ctc atg gct cac ggg agg gaa ggc ttc ctc  249
Ser Cys Ala Phe Val Val Leu Met Ala His Gly Arg Glu Gly Phe Leu
                 55                  60                  65 aag gga gaa gat ggg gag atg gtc aag ctg gag aat ctc ttc gag gcc  297
Lys Gly Glu Asp Gly Glu Met Val Lys Leu Glu Asn Leu Phe Glu Ala
             70                  75                  80 ctg aac aac aag aac tgc cag gcc ctg cga gct aag ccc aag gtg tac  345
Leu Asn Asn Lys Asn Cys Gln Ala Leu Arg Ala Lys Pro Lys Val Tyr
 85                  90                  95 atc ata cag gcc tgt cga gga gaa caa agg gac ccc ggt gaa aca gta  393
Ile Ile Gln Ala Cys Arg Gly Glu Gln Arg Asp Pro Gly Glu Thr Val
100                 105                 110                 115 ggt gga gat gag att gtg atg gtc atc aaa gac agc cca caa acc atc  441
Gly Gly Asp Glu Ile Val Met Val Ile Lys Asp Ser Pro Gln Thr Ile
                120                 125                 130 cca aca tac aca gat gcc ttg cac gtt tat tcc acg gta gag gga tac  489
Pro Thr Tyr Thr Asp Ala Leu His Val Tyr Ser Thr Val Glu Gly Tyr
             135                 140                 145 atc gcc tac cga cat gat cag aaa ggc tca tgc ttt atc cag acc ctg  537
Ile Ala Tyr Arg His Asp Gln Lys Gly Ser Cys Phe Ile Gln Thr Leu
                 150                 155                 160

Fig. 9A

```
gtg gat gtg ttc acg aag agg aaa gga cat atc ttg gaa ctt ctg aca    585
Val Asp Val Phe Thr Lys Arg Lys Gly His Ile Leu Glu Leu Leu Thr
    165                 170                 175 gag gtg acc cgg cgg atg gca gaa gca gag ctg gtt caa gaa gga aaa    633
Glu Val Thr Arg Arg Met Ala Glu Ala Glu Leu Val Gln Glu Gly Lys
180                 185                 190                 195 gca agg aaa acg aac cct gaa atc caa agc acc ctc cgg aaa cgg ctg    681
Ala Arg Lys Thr Asn Pro Glu Ile Gln Ser Thr Leu Arg Lys Arg Leu
                200                 205                 210 tat ctg cag tag                                                    693
Tyr Leu Gln
```

*Fig. 9B*

```
  1 MESEMSDPQPLQEERYDMSGARLALTLCVTKAREGSEVDMEALERMFRYL  50
    ||.|. |:||:|||||||||| |||||||||||| |::||| ||| |
  1 ....MSNPRSLEEEKYDMSGARLALILCVTKAREGSEEDLDALEHMFRQL  46

51 KFESTMKRDPTAQQFLEELDEFQQTIDNWEEPVSCAFVVLMAHGEEGLLK 100
    :||||||||||:|| |||:..||| ||. |:|||||||||||| || ||
 47 RFESTMKRDPTAEQFQEELEKFQQAIDSREDPVSCAFVVLMAHGREGFLK  96

101 GEDEKMVRLEDLFEVLNNKNCKALRGKPKVYIIQACRGEHRDPGEELRGN 150
    ||| .||:||.||| ||||||.||| |||||||||||||||||| ||||
 97 GEDGEMVKLENLFEALNNKNCQALRAKPKVYIIQACRGEQRDPG...... 140

151 EELGGDEELGGDEVAVLKNNPQSIPTYTDTLHIYSTVEGYLSYRHDEKGS 200
    | .||||       | |:|..||.|||||| ||:|||||||:.||||:|||
141 ETVGGDE.....IVMVIKDSPQTIPTYTDALHVYSTVEGYIAYRHDQKGS 185

201 GFIQTLTDVFIHKKGSILELTEEITRLMANTEVMQEGKPRKVNPEVQSTL 250
    ||||| ||| :|| |||| |:|| || |..|||| || |||:||||
186 CFIQTLVDVFTKRKGHILELLTEVTRRMAEAELVQEGKARKTNPEIQSTL 235

251 RKKLYLQ* 257
    ||:||||
236 RKRLYLQ* 242
```

*Fig. 10*

CASPASE-14, AN APOPTOTIC PROTEASE, NUCLEIC ACIDS ENCODING AND METHODS OF USE

CROSS-REFERENCE TO RELATED APPLICATION

This application is a continuation-in-part of U.S. Ser. No. 09/139,600, filed Aug. 25, 1998, now pending, which application claims the benefit of priority from U.S. Provisional Application Serial No. 60/056,986, filed Aug. 26, 1997 now abandoned.

STATEMENT OF GOVERNMENT INTEREST

This invention was made with government support under grant AI 35035-1 from the National Institutes of Health. Accordingly, the government has certain rights to this invention.

TECHNICAL FIELD

This invention relates generally to caspase-14, and in particular, to nucleic acids encoding caspase-14, the encoded polypeptides, antibodies thereto, and methods of identifying modulators of caspase-14 activity.

BACKGROUND OF THE INVENTION

Apoptosis, also referred to as physiological cell death or programmed cell death, is a normal physiological process of cell death that plays a critical role in the regulation of tissue homeostasis by ensuring that the rate of new cell accumulation produced by cell division is offset by a commensurate rate of cell loss due to death. Apoptosis can be characterized by morphological changes in the cell, including fragmentation of nuclear chromatin, compaction of cytoplasmic organelles, dilatation of the endoplasmic reticulum, a decrease in cell volume and alterations to the plasma membrane, resulting in the recognition and phagocytosis of apoptotic cells and prevention of an inflammatory response. Disturbances in apoptosis that prevent or delay normal cell turnover can be just as important to the pathogenesis of diseases as are known abnormalities in the regulation of proliferation and the cell cycle. Like cell division, which is controlled through complex interactions between cell cycle regulatory proteins. apoptosis is similarly regulated under normal circumstances by the interaction of gene products that either induce or inhibit cell death.

The stimuli that regulate the function of these apoptotic gene products include both extracellular and intracellular signals. Either the presence or the removal of a particular stimulus can be sufficient to evoke a positive or negative apoptotic signal. Physiological stimuli that inhibit or reduce the likelihood of apoptosis include, for example, growth factors, extracellular matrix, CD40 ligand, viral gene products, neutral amino acids, zinc, estrogen and androgens. In contrast, stimuli that promote apportions include, for example, tumor necrosis factor (TNF). Fas, transforming growth factor β (TGFβ), neurotransmitters, growth factor withdrawal, loss of extracellular matrix attachment, intracellular calcium and glucocorticoids. Other stimuli, including those of environmental and pathogenic origin, also exist and can either induce or inhibit apoptosis. Although apoptosis is mediated by diverse signals and complex interactions of cellular gene products, the results of these interactions ultimately lead into a cell death pathway that is evolutionarily conserved between humans and invertebrates.

Several gene products that modulate the apoptotic process have been identified. Although these products can, in general, be separated into two basic categories, gene products from each category can function to either inhibit or induce apoptosis. One family of gene products is the Bcl-2 family of proteins. Bcl-2 is the best characterized member of this family and inhibits apoptosis when overexpressed in cells. Other members of the Bcl-2 family of proteins include, for example, Bax, Bak, Bcl-$x_L$, Bcl-$x_S$ and Bad. While some of these proteins can inhibit apoptosis, others can induce apoptosis (for example, Bcl-$x_S$ and Bak, respectively).

A second family of gene products, the caspase family, is related genetically to the C. elegans ced-3 gene product, which is required for apoptosis in the roundworm, C. elegans. The caspase family includes, for example, caspase-1, caspase-2, caspase-3, caspase-4, caspase-5, caspase-6, caspase-7, caspase-8, caspase-9 and caspase-10. Among the common features of the caspase gene products is that 1) they are cysteine proteases with specificity for substrate cleavage at Asp-X bonds, where "X" is an amino acid; 2) they share a conserved pentapeptide sequence within the active site; and 3) they are synthesized as proenzymes that require proteolytic cleavage at specific aspartate residues for activation of protease activity. Cleavage of the proenzyme produces two polypeptide protease subunits, which combine non-covalently to form a tetramer comprised of two heterodimers. Although these proteases, when expressed in cells, induce apoptosis, several alternative structural forms of these proteases, such as caspase-1δ (ICEδ). caspase-1ε (ICEε), caspase-$2_S$ (ICH-$1_S$). caspase-6β(Mch2β) and caspase-7β (Mch3β), inhibit apoptosis.

In addition to the Bcl-2 and caspase families, which play a role in apoptosis in mammalian cells, other gene products are important in mammalian apoptosis. For example, in addition to ced-3, another C. elegans gene product, ced-4, is required for apoptosis in C. elegans. Apaf-1, a human protein homologous to ced-4, binds cytochrome c and may activate caspase-3, leading to apoptosis. In addition, another protein, casper, while not a caspase, has sequence similarity to caspase-8 throughout its length and interacts with caspase-8 and caspase-3 through distinct domains. Overexpression of casper in mammalian cells induces apoptosis.

It is uncertain whether other genes encode members of either of the Bcl-2 or caspase gene families and, if so, what role they play in the apoptotic pathway. It also is unclear what physiological control mechanisms regulate apoptosis and how the apoptotic pathways interact with other physiological processes. For example, it has been suggested that cytotoxic T lymphocytes mediate their destructive function by inducing apoptosis in their target cells.

The process of apoptosis maintains tissue homeostasis in various physiological processes, including embryonic development, immune cell regulation and normal cell turnover. It follows that the loss of apoptosis can lead to a variety of pathological disease states. For example, the inappropriate loss of apoptosis can lead to the pathological accumulation of self-reactive lymphocytes such as those occurring in association with many autoimmune diseases. Inappropriate loss of apoptosis also can lead to the accumulation of virally infected cells and of hyperproliferative cells such as tumor cells. Similarly, the inappropriate activation of apoptosis can contribute to a variety of pathological disease states including, for example, acquired immunodeficiency syndrome (AIDS), neurodegenerative diseases and ischemic injury. Treatments that are specifically designed to modulate the apoptotic pathways in these and other pathological conditions can change the natural progression of many of these diseases.

Thus, there exists a need to identify apoptotic genes and their gene products and for methods of modulating apoptosis for the therapeutic treatment of human diseases. The present invention satisfies this need and provides related advantages as well.

SUMMARY OF THE INVENTION

The invention generally provides caspase-14. In one aspect, the invention provides an isolated nucleic acid molecule encoding a caspase-14 polypeptide or a functional fragment thereof. Nucleic acid and amino acid sequences of caspase-14 are provided. The invention also provides caspase-14 polypeptides or a functional fragment thereof.

In another aspect, a vector that contains the nucleic acid molecule and a host cell that contains the vector is also provided. Also provided is an expression vector comprising the nucleic acid molecule encoding caspase- 14 that is operatively linked to a promoter.

In other aspects, an isolated caspase-14 polypeptide and functional fragment thereof are also provided, as are antibodies that specifically bind thereto. In addition, the invention provides methods of identifying compounds that modulate caspase-14 activity comprising: (a) contacting a sample containing a caspase-14 polypeptide or functional fragment thereof with a test compound, and thereafter (b) determining the activity of caspase-14 polypeptide or functional fragment thereof.

Methods are also provided for identifying inhibitors and enhancers of caspase-14 activity, comprising: (a) contacting an activated caspase-14 polypeptide with a substrate in the presence of a test compound under conditions in which the caspase-14 processes the substrate in the absence of the test compound; and thereafter (b) detecting increased or decreased substrate turnover, wherein increased substrate turnover indicates the presence of an enhancer and wherein decreased substrate turnover indicates the presence of an inhibitor.

These and other aspects of the present invention will become evident upon reference to the following detailed description and attached drawings. In addition, the various references set forth below that describe in more detail certain procedures or compositions (e.g., plasmids, etc.), and are therefore incorporated herein, by reference, in their entirety.

BRIEF DESCRIPTION OF THE DRAWINGS

FIG. 1 illustrates the nucleotide sequence (SEQ ID NO:1 and SEQ ID NO:76 ) for compliant strand and deduced amino acid sequence (SEQ ID NO:2) of caspase-14. The double-stranded nucleotide sequence is shown, with nucleotide position numbers shown on the left and right sides. The encoded amino acids are shown below each row of nucleotides, with stop codons designated by an asterisk. The start codon, which is shown at nucleotide positions 61 to 63. was identified based on the presence of a stop codon upstream of this position (nucleotide positions 49 to 51). Amino acid position numbers are shown on the right side of the sequence, with the letter "a" shown on the left side of the amino acid sequence and the initial methionine designated position 1. The open reading frame encodes caspase-14, which is 257 amino acids in length, and ends with a stop codon at nucleotide positions 832 to 834.

FIG. 2 illustrates the amino acid sequence analysis and primary structure of caspase-14. FIG. 2A shows a colinear alignment of the predicted amino acid sequence of procaspase-14 with the amino acid sequence of 8 other known caspases. Noncontiguous sequences of caspase-14 (SEQ ID NOS:62–68), Mch5 (caspase-8; SEQ ID NOS:48–54), Mch3 (caspase-7; SEQ ID NOS:35–41) Mch2 (caspase-6; SEQ ID NOS:42–47), CPP32 (caspase-3; SEQ ID NOS:27–34), ICE (caspase-1; SEQ ID NOS:21–26), ICH-1 (caspase-2; SEQ ID NOS: 55–61) capase-11 (SEQ ID NO: 10–15), and capase-12 (SEQ ID NO: 16–20) are shown. The amino acid position of the first amino acid shown in the respective proteins is indicated on the left. FIG. 2B depicts the primary structure of procaspase-14 represented by a bar diagram. The active site QACRG (SEQ ID NO:3) pentapeptide and potential aspartate processing sites are indicated.

FIG. 7 illustrates the nucleotide sequence (SEQ ID NO:4) and the deduced amino acid sequence (SEQ ID NO:5) of caspase-14. The nucleotide sequence is shown with nucleotide position numbers shown on the right side. The encoded amino acids are shown below each row of nucleotides, with stop codons designated by an asterisk. The start codon, which is shown at nucleotide positions 49 to 51. Amino acid position numbers are shown below the sequence and the initial methionine designated position 1. The open reading frame encodes a caspase-14, which is 242 amino acids in length, and ends with a stop codon at nucleotide positions 775–777.

FIG. 8 illustrates the nucleotide sequence (SEQ ID NO:6) and the deduced amino acid sequence (SEQ ID NO:7) of a splice variant of human caspase-14. The nucleotide sequence is shown, with nucleotide position numbers shown to the right side. The encoded amino acids are shown below each row of nucleotides, with stop codon designated by an asterisk. The start codon, which is shown at nucleotide positions 49 to 51. Amino acid position numbers are shown below the sequence and the initial methionine designated position 1. The open reading frame encodes a caspase-14, which is 230 amino acids in length. The active site is at amino acid positions 130–134 and the cleavage between the large and small subunit is at positions 146 and 147. This sequence differs from that in FIG. 7 in that there is an intronic insertion at position 568 which results in a shift in the reading frame and a shorter protein.

FIG. 9 illustrates the nucleotide sequence (SEQ ID NO:8) and the deduced amino acid sequence (SEQ ID NO:9) of a splice variant of human caspase-14. The nucleotide sequence is shown, with nucleotide position numbers shown to the right side. The encoded amino acids are shown below each row of nucleotides. with stop codon designated by an asterisk. The start codon, which is shown at nucleotide positions 49 to 51. Amino acid position numbers are shown below the sequence and the initial methionine designated position 1. The open reading frame encodes a caspase-14, which is 214 amino acids in length. The active site is at amino acid positions 102–106 and the cleavage site separating the large and small subunit is between positions 118 and 119. This sequence differs from that in FIG. 7 in that it has an internal deletion at position 151, which results in a shorter protein.

FIG. 10 is an identity comparison between the mouse and human caspase-14 polypeptide sequences as described in Example 1. The mouse sequence (SEQ ID NO:2) is represented on the top line and the human sequence (SEQ ID NO:5) is represented on the bottom line.

DETAILED DESCRIPTION OF THE INVENTION

Figure 3:
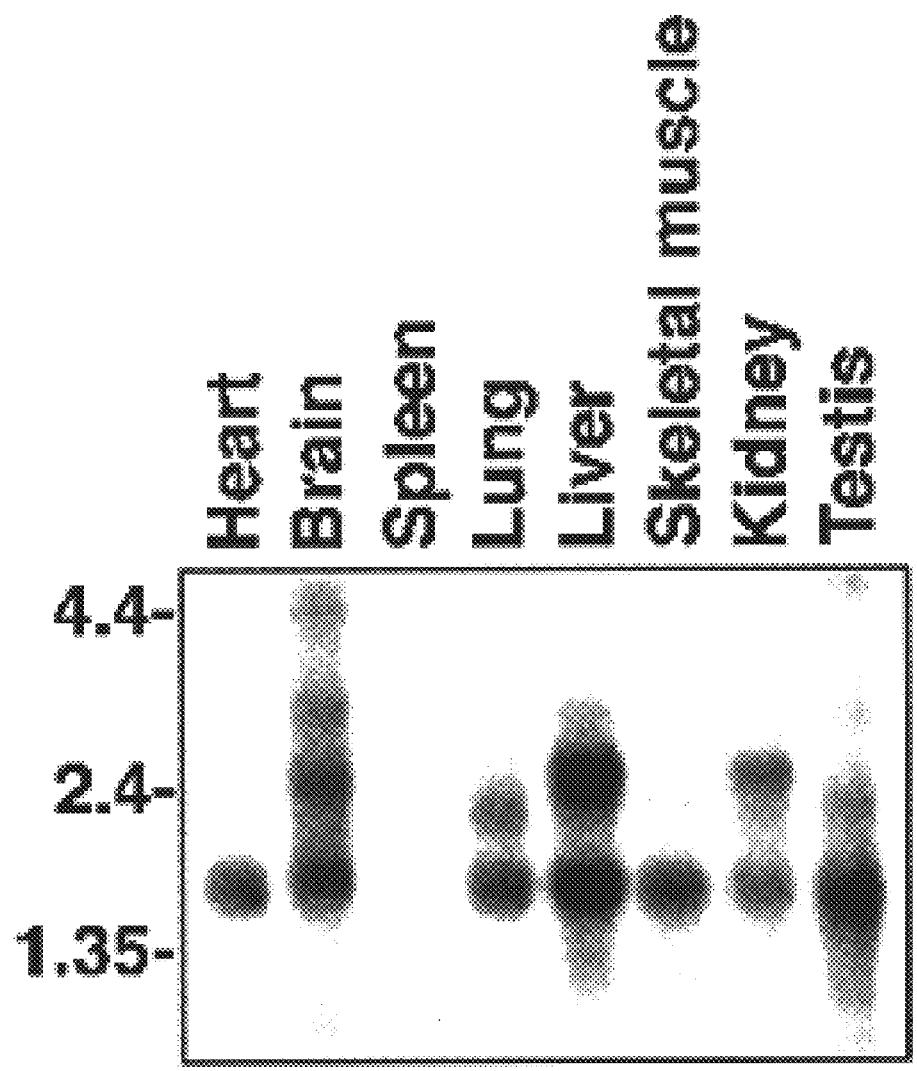
FIG. 3 is a scanned image of an autoradiogram representing a Northern blot of the tissue distribution in mouse of caspase-14 mRNA.

This invention relates to a cell death specific protease, termed caspase-14, which is a member of the caspase family of proteases that includes, for example, with alternate designations in parentheses, caspase-1 (ICE, interleukin-1-β converting enzyme). caspase-$2_L$ (ICH-$1_L$), caspase-$2_S$ (ICH-$1_S$), caspase-3 (CPP32), caspase-4 (TX, ICH2, ICE$_{rel}$-II), caspase-5 (ICE$_{rel}$-III, TY), caspase-6 (Mch2), caspase-7 (Mch3, ICE-LAP3, CMH-1), caspase-8 (Mch5, MACH, FLICE), caspase-9 (Mch6, ICE-LAP6) and caspase-10 (Mch4). Similar to other caspases, caspase-14 is produced as a proenzyme and becomes active following proteolytic cleavage into a larger and smaller subunit. The two subunits form heterodimers that associate with each other into a heterotetrameric active complex, which induces apoptosis. Substrate specificity uniquely requires an aspartic acid residue in the P1 position of the substrate binding site with a small, preferably hydrophobic residue in the P1 position.

A nucleic acid molecule (SEQ ID NO:1), which encodes a caspase-14 polypeptide (SEQ ID NO:2) was identified and isolated based on identifying an expressed sequence tag (EST) having GenBank accession number AA103647, a sequence of 483 nucleotides in length. The EST was identified during a homology search of the GenBank database using a query nucleotide sequence based on caspase-3 and caspase-6 coding sequences (see Example 1). The mouse cell clone that contained the sequence from which the EST was derived was obtained from IMAGE Consortium. It was discovered that the clone, which had been only partially and inaccurately sequenced, contained a nucleotide sequence (SEQ ID NO:1) encoding caspase-14. This caspase had the highest homology with procaspase-3 (32% identity) and procaspase-7 (31% identity). The differences between the EST and the corresponding sequence of the coding strand shown in FIG. 1 (SEQ ID NO:1) include, for example, that the coding strand shown in FIG. 1 (SEQ ID NO:1) contains a cytosine at nucleotide position 13 and guanines at nucleotide positions 54 and 164, while the EST contains nothing at the corresponding positions.

The invention also provides additional caspase-14 nucleic acid molecules such as (SEQ ID NO:4), that encodes human caspase-14 (SEQ ID NO:5), which is preferentially expressed in keratenocytes as determined by RT-PCR in normal keratenocytes as well as transformed keratenocytes such as the A431 cell line. As demonstrated by FIG. 7, the nucleotide sequence is 777 nucleotides, while the encoded polypeptide is 242 amino acids in length. This human sequence was identified as demonstrated in Example 1, using nested PCR primers corresponding to the mouse sequence (SEQ ID NO:1). Further provided are splice variant isoforms of SEQ ID NO:4. In one embodiment such isoforms are provided by nucleic acid molecules illustrated in FIG. 8 (SEQ ID NO:6) and FIG. 9 (SEQ ID NO:8) as well as their respectively encoded human caspase-14 polypeptides (SEQ ID NOS:7 and 9). Such splice variants are identified using high stringency probes derived from SEQ ID NOS:1 or 4.

The invention provides isolated caspase-14 polypeptides such as SEQ ID NOS:2 or 5 as well as splice variants thereof (e.g., SEQ ID NOS:7 and 9). The term "isolated" means in a form that is relatively free from contaminating lipids. unrelated polypeptides, nucleic acids and other cellular material normally associated with the polypeptide in the cell and at least about 30% of the total material. In another embodiment of the invention, the isolated caspase-14 polypeptide is about 50% of the total material. In another embodiment of the invention, the isolated caspase-14 polypeptide is about 70% of the total material. In another embodiment of the invention, the isolated caspase-14 polypeptide is about 90% of the total material. In yet another embodiment of the invention, the isolated caspase-14 polypeptide is greater than about 95% of the total material. Thus, an isolated polypeptide of the invention is one that is in a form that is different from the naturally occurring state.

Exemplary polypeptides of the invention are the isolated mouse caspase-14 polypeptide 257 amino acids in length and shown as SEQ ID NO:2 (FIG. 1), the isolated human caspase-14 polypeptide 242 amino acids in length and shown as SEQ ID NO:5 (FIG. 7), and the isolated human caspase-14 isoforms shown as SEQ ID NOS:7 and 9. The invention further provides an isolated caspase-14 polypeptide, which has greater than about 33% amino acid sequence identity with SEQ ID NOS:2, 5 or their respective isoforms. In other embodiments of the invention, the polypeptide has generally greater than about 50% or 60% amino acid sequence identity with SEQ ID NOS:2, 5 or their respective splice variant isoforms. In yet other embodiments of the invention, the polypeptide has generally greater than about 70% or 80% amino acid sequence identity with SEQ ID NOS:2, 5, or their respective isoforms. Such amino acid sequence identity may be determined by standard methodologies, including use of the National Center for Biotechnology Information BLAST search methodology available at www.ncbi.nlm.nih.gov. The identity methodologies preferred are those described in U.S. Pat. No. 5,691,179 and Altschul et al., Nucleic Acids Res. 25:3389–3402, 1997 all of which are incorporated herein by reference. Most preferred and that which is used to calculate percentages herein is the pileUP algorithm as described in Example 1.

A caspase-14 polypeptide includes polypeptides having substitutions of conserved and non-essential amino acids of SEQ ID NOS:2 or 5 and, generally includes, for example, mammalian homologues of SEQ ID NOS:2 or 5 such as rat or other mammalian caspase-14. A caspase-14 polypeptide also can include polypeptides having related but different sequences, provided the polypeptide has at least one functional activity of SEQ ID NOS:2 or 5, such as protease activity. For example, splice variant isoforms of SEQ ID NOS:1 or 4, such as those provided by SEQ ID NOS:6 and 8 are included in such a definition. Therefore, it should be understood that when referencing the various polypeptides and nucleic acid molecules, the splice variant isoforms and homologous sequences thereof are implicated as well. Accordingly, with regard to fragments, the specific disclaimers to contiguous sequences found in the prior art as to SEQ ID NOS: 1, 2, 4, and 5, also includes the identical sequences found in SEQ ID NOS:6–9.

It is understood that limited modifications may be made to a caspase-14 polypeptide without destroying its biological function and that only a portion of the entire primary structure may be required in order to effect activity. Thus, for example, minor modifications of SEQ ID NOS:2 or 5 provide examples of caspase-14 polypeptides. Such minor modifications may result in polypeptides that have substantially equivalent or enhanced function as compared to SEQ ID NOS:2 or 5. These modifications may be deliberate, such as through site-directed mutagenesis, or may be accidental, such as through mutation in hosts that are caspase-14 producers. It also is understood that allelic variants and splice variants of caspase-14 are caspase-14 polypeptides encompassed within the invention.

In addition, the invention provides a functional fragment of SEQ ID NOS:2 or 5 or splice variants thereof. A functional fragment of SEQ ID NOS:2 or 5 is defined structurally and functionally in that it has the same contiguous sequence as a portion of SEQ ID NOS:2 or 5 and at least one biological activity characteristic of caspase-14. A functional fragment of SEQ ID NOS:2, 5, or a splice variant thereof comprises at least 8 contiguous residues of SEQ ID NOS:2, 5, or a splice variant thereof. In other embodiments of the invention, a functional fragment of SEQ ID NOS:2, 5, or a splice variant thereof, comprises an amino acid sequence of at least 10 or 12 contiguous residues. In other embodiments of the invention, a functional fragment of SEQ ID NOS:2 or 5 comprises an amino acid sequence of at least 15 or 20 contiguous residues. In other embodiments of the invention, a functional fragment of SEQ ID NOS:2. 5, or splice variants thereof, comprises an amino acid sequence of a; least 25 or 30 continuous residues. In another embodiment of the invention, a functional fragment of SEQ ID NOS:2, 5, or splice variants thereof comprises an amino acid sequence of at least 50 contiguous residues. In yet other embodiments of the invention, a functional fragment of SEQ ID NO:2 comprises an amino acid sequence of at least 6 or 7 contiguous residues of SEQ ID NO:2, provided that such sequence does not include amino acid positions 132 to 138 or 134 to 139 of SEQ ID NO:2 or the homologous sequences from splice variant forms. In yet other embodiments of the invention, a functional fragment of SEQ ID NO:5 comprises an amino acid sequence of at least 6 or 7 contiguous residues of SEQ ID NO:2, provided that such sequence does not include amino acid positions 128 to 133 or 130 to 135 of SEQ ID NO:5 or the homologous sequences from splice variant forms. However, an amino acid sequence that consists of the identical amino acid sequence encoded by the EST having GenBank accession number AA103647, or any contiguous portion thereof, is not a functional fragment of SEQ ID NOS:2 or 5 encompassed within the invention. Similarly, a contiguous portion of caspase-l, caspase-2, caspase-3, caspase-4, caspase-5, caspase-6, caspase-7, caspase-8, caspase-9, caspase-10 or ced-3 is not a functional fragment of SEQ ID NOS:2, 5, 7, or 9, encompassed within the invention. A biological activity of a functional fragment of SEQ ID NOS:2 or 5 is an activity of caspase-14 and can be, for example, the ability to bind a ligand, have protease or other enzymatic activity, enhance or inhibit apoptosis or bind or induce the production of an anti-caspase-14 antibody.

The invention also provides a functional fragment of a caspase-14 polypeptide. Such a functional fragment is defined structurally and functionally in that it has amino acid sequence identity to a portion of SEQ ID NOS:2 or 5, as described below, and has at least one biological activity of caspase-14, as described above. A functional fragment of a caspase-14 polypeptide that does not include QACRG (SEQ ID NO:3, amino acid positions 134 to 138 of SEQ ID NO:2; amino acid positions 130–134 of SEQ ID NO:5 or the homologous portions of a splice variant) has several embodiments. In one embodiment such a functional fragment comprises at least 10 amino acids and has at least about 70% amino acid sequence identity with a portion of SEQ ID NOS:2, 5, 7, or 9. In other embodiments. such a functional fragment comprises at least 10 amino acids and has at least about 75% or 80% amino acid sequence identity with a portion of SEQ ID NOS:2, 5, 7, or 9. In other embodiments, such a functional fragment comprises at least 10 amino acids and has at least about 85% or 90% amino acid sequence identity with a portion of SEQ ID NOS:2, 5, 7, or 9. In another embodiment, such a functional fragment comprises at least 25 amino acids and has at least about 65% amino acid sequence identity with a portion of SEQ ID NOS:2, 5, 7, or 9. In other embodiments, such a functional fragment comprises at least 25 amino acids and has at least about 70% or 75% amino acid sequence identity with a portion of SEQ ID NOS:2, 5, 7, or 9. In other embodiments, such a functional fragment comprises at least 25 amino acids and has at least about 80% or 85% amino acid sequence identity with a portion of SEQ ID NOS:2, 5, 7, or 9. In other embodiments, such a functional fragment comprises at least 40 amino acids and has at least about 50% or 60% amino acid sequence identity with a portion of SEQ ID NOS:2, 5, 7, or 9. In yet other embodiments, such a functional fragment comprises at least 40 amino acids and has at least about 70% or 80% amino acid sequence identity with a portion of SEQ ID NOS:2, 5, 7, or 9. The aforementioned identities being calculated with the pileUP algorithm as defined in Example 1.

In comparison, a functional fragment of a caspase-14 polypeptide that includes QACRG (SEQ ID NO:3; amino acid positions 134 to 138 of SEQ ID NO:2; amino acid positions 130 to 134 of SEQ ID NO:5 or homologous portions of splice variants) comprises at least about 13 amino acids and has greater than about 92% amino acid sequence identity with a portion of SEQ ID NOS:2, 5, 7, or 9. In other embodiments of the invention, such a functional fragment comprises at least about 13 amino acids and has greater than about 93% or 95% amino acid sequence identity with a portion of SEQ ID NOS:2, 5, 7, or 9. In another embodiment of the invention, such a functional fragment comprises at least about 13 amino acids and has greater than about 98% amino acid sequence identity with a portion of SEQ ID NOS:2, 5, 7, or 9. In another embodiment of the invention, such a functional fragment comprises at least about 25 amino acids and has greater than about 72% amino acid sequence identity with a portion of SEQ ID NOS:2, 5, 7, or 9. In other embodiments of the invention, such a functional fragment or comprises at least about 25 amino acids and has greater than about 75% or 80% amino acid sequence identity with a portion of SEQ ID NOS:2, 5, 7, or 9. In yet other embodiments of the invention, such a functional fragment or comprises at least about 25 amino acids and has greater than about 85% or 90% or 95% amino acid sequence identity with a portion of SEQ ID NOS:2, 5, 7, or 9. A fragment that consists of the identical amino acid sequence encoded by the EST having GenBank accession number AA103647, or any contiguous portion thereof, or of any contiguous portion of caspase-1, caspase-2, caspase-3, caspase-4, caspase-5, caspase-6, caspase-7, caspase-8, caspase-9, caspase-10 or ced-3, is not considered a functional fragment of a caspase-14 polypeptide.

It is understood that functional fragments of a caspase-14 polypeptide include fragments with substitutions of conserved and non-essential amino acids of portions of SEQ ID NO:2 and, therefore, include for example, fragments of eukaryotic homologs of SEQ ID NO:2 such as fragments of yeast or Drosophila or C. elegans caspase-14. However, it also is understood, that contiguous fragments of caspase-1, caspase-2, caspasc-3, caspase-4, caspase-5, caspase-6, caspase-7, caspase-8, caspase-9, caspase-10 or ced-3 polypeptides, for example, are not functional fragments of a caspase-14 polypeptide encompassed within the invention.

SEQ ID NOS:2 or 5 are inactive proenzymes, which are proteolytically cleaved to form a large subunit and a small subunit, which provide examples of functional fragments of SEQ ID NOS:2 or 5. Proteolytic cleavage of SEQ ID NO:2 occurs between the aspartic acid and glutamic acid residues of the shown in FIG. 2. Thus, cleavage occurs between amino acid positions 156 and 157 of SEQ ID NO:2 and between amino acid positions 162 and 163 of SEQ ID NO:2, resulting in a large subunit comprising amino acid positions 1 to 156 of SEQ ID NO:2 and a small subunit comprising amino acid positions 163 to 257 of SEQ ID NO:2. Proteolytic cleavage of SEQ ID NO:5 occurs between the aspartic acid and glutamic acid residues at positions 146 and 147 of SEQ ID NO:5, resulting in a large subunit comprising amino acids 1–146 of SEQ ID NO:5 and a small subunit comprising amino acid positions 147–242 of SEQ ID NO:5. Other caspase-14 polypeptides, which are inactive proenzymes, also are proteolytically cleaved to form large subunits and small subunits, which provide examples of functional fragments of caspase-14. The large and small subunits of a caspase-14 polypeptide can combine non-covalently to produce a heterotetramer having apoptotic activity.

If desired, the large subunit of a caspase-14 polypeptide can be combined with a small subunit of another caspase polypeptide such as caspase-3 (CPP32) to form an apoptotic complex, or the small subunit of a caspase-14 polypeptide can be combined with a large subunit of another caspase protein such as caspase-3 (CPP32) to form an apoptotic complex. Such complexes can be formed in vitro, in cells in culture, or in vivo by heterodimerization of the large and small subunits.

The activity of a caspase-14 polypeptide or functional fragment thereof can be measured enzymatically (see Example 2). If desired, a caspase-14 polypeptide or functional fragment thereof can be attached to a second molecule such as, for example, a protein, carbohydrate, lipid or chemical moiety. For example, a caspase-14 polypeptide or functional fragment thereof can be fused to a heterologous protein such as a fusion protein that retains caspase-14 enzymatic or other biological activity and has a characteristic of the heterologous protein.

An isolated caspase-14 polypeptide or functional fragment thereof can be obtained by a variety of methods known in the art. For example, a caspase-14 polypeptide can be isolated by biochemical methods such as affinity chromatography. Affinity matrices that can be used for caspase-14 isolation can be a solid phase having attached thereto anti-caspase-14 monoclonal or polyclonal antibodies prepared against a caspase-14 polypeptide or a functional fragment thereof comprising a caspase-14 epitope. Alternatively, ligands such as substrate analogues or enzymatic inhibitors of caspase-14 can be used as affinity matrices to isolate a caspase-14 polypeptide or functional fragment thereof that binds the ligand.

Other biochemical methods for isolating a caspase-14 polypeptide or functional fragment thereof include preparative gel electrophoresis, gel filtration, affinity chromatography, ion exchange and reversed phase chromatography, chromatofocusing, isoelectric focusing and sucrose or glycerol density gradients (Deutscher, *Methods in Enzymology: Guide to Protein Purification,* Vol. 182, Academic Press, Inc., San Diego (1990), Chapter 38; Balch et al., *Methods in Enzymology,* Vol. 257, Academic Press, Inc., San Diego (1995), Chapter 8). For example, a caspase-14 polypeptide or functional fragment thereof can be isolated by preparative polyacrylamide gel electrophoresis and elution by diffusion or electroelution (Deutscher, supra, 1990, Chapter 33). Continuous elution gel electrophoresis using a system such as the Model 491 Prep Cell (BioRad, Hercules, Calif.) can be used to isolate a caspase-14 polypeptide or functional fragment thereof. If desired, continuous elution gel electrophoresis can be combined with further purification steps such as liquid phase preparative isoelectric focusing using, for example, the Rotofor system (BioRad).

A caspase-14 polypeptide or functional fragment thereof also can be produced by chemical synthesis, for example, by the solid phase peptide synthesis method (Merrifield et al., *J. Am. Chem. Soc.* 85:2149 (1964)). Standard solution methods well known in the art also can be used to synthesize a caspase-14 polypeptide or functional fragment thereof (Bodanszky, *Principles of Peptide Synthesis,* Springer-Verlag, Berlin (1984); Bodanszky, *Peptide Chemistry,* Springer-Verlag, Berlin (1993)). A newly synthesized caspase-14 polypeptide or functional fragment thereof can be isolated, for example, by high performance liquid chromatography and can be characterized using mass spectrometry or amino acid sequence analysis.

A caspase-14 polypeptide or functional fragment thereof also can be produced by recombinant DNA methods. Accordingly, the invention provides a nucleic acid molecule encoding a caspase-14 polypeptide or functional fragment thereof. Such a nucleic acid molecule can be cloned into an appropriate vector for propagation, manipulation or expression as desired. Such a vector is commercially available or can be constructed by those skilled in the art and contains expression elements necessary for the transcription, translation, regulation, and, if desired, sorting of the caspase-14 polypeptide or functional fragment thereof. The selected vector also can be used in a procaryotic or eukaryotic host system, as appropriate, provided the expression and regulatory elements are of compatible origin. A recombinant caspase-14 polypeptide or functional fragment thereof produced in a host cell or secreted from the cell can be isolated using, for example, an anti-caspase-14 antibody, as described herein.

Caspase-14 may be expressed in a variety of host organisms. In certain embodiments, caspase-14 is produced in bacteria, such as *E. coli,* or mammalian cells (e.g., CHO and COS-7), for which many expression vectors have been developed and are available. Other suitable host organisms include other bacterial species, and eukaryotes, such as yeast (e.g., *Saccharomyces cerevisiae*), and insect cells (e.g., Sf9).

In one embodiment, a DNA sequence encoding, caspase-14 is introduced into an expression vector appropriate for the host cell. In certain embodiments, caspase-14 is inserted into a vector such that a fusion protein is produced. The caspase-14 sequence is derived as described herein. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At a minimum, the vector will contain a promoter sequence. As used herein, a "promoter" refers to a nucleotide sequence that contains elements that direct the transcription of a linked gene. At a minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked".

Other regulatory sequences may be included. Such sequences include a transcription termination sequence, secretion signal sequence, origin of replication, selectable marker, and the like. The regulatory sequences are operationally associated with one another to allow transcription or translation.

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5. and SP6, and the trp, lpp, and lac operons. Hybrid promoters (see, U.S. Pat. No. 4,551,433), such as tac and trcy may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009). ecdysone response element system, tetracycline-reversible silencing system (tet-on, tet-off), and the like.

The promoter controlling transcription of caspase-14 may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the $E.$ $coli$ lacI repressor responsive to IPTG induction, the temperature sensitive $\lambda$cI857 repressor, and the like.

In other optional embodiments, the vector also includes a transcription termination sequence. A "transcription terminator region" has either a sequence that provides a signal that terminates transcription by the polymerase that recognizes the selected promoter and/or a signal sequence for polyadenylation.

In one aspect, the vector is capable of replication in the host cells. Thus, when the host cell is a bacterium, the vector preferably contains a bacterial origin of replication. Bacterial origins of replication include the fl-ori and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g, thymidine kinase (tk) in tk- hosts). However, drug markers are also available (e.g., G418 resistance and hygromycin resistance).

The sequence of nucleotides encoding caspase-14 may also include a secretion signal, whereby the resulting peptide is a precursor protein processed and secreted. The resulting processed protein may be recovered from the periplasmic space or the fermentation medium. Secretion signals suitable for use are widely available and are well known in the art (von Heijne, $J.$ $Mol.$ $Biol.$ 184:99–105, 1985). Prokaryotic and eukaryotic secretion signals that are functional in $E.$ $coli$ (or other host) may be employed. The presently preferred secretion signals include, but are not limited to. those encoded by the following $E.$ $coli$ genes: pelB (Lei el al., $J.$ $Bacteriol.$ 169:4379, 1987), phoA, ompA, ompT, ompF, ompC, beta-lactamase, and alkaline phosphatase.

One skilled in the art will appreciate that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ 18 (Amersham International plc, England), pACYC 177, pGEX series, and the like are suitable for expression of caspase-14. Baculovirus vectors, such as pBlueBac (see, e.g., U.S. Pat. Nos. 5,278, 050, 5,244.805, 5,243,041, 5,242,687, 5,266,317, 4,745,051, and 5,169,784; available from Invitrogen, San Diego) may be used for expression in insect cells, such as $Spodoptera$ $frugiperda$ sf9 cells (see, U.S. Pat. No. 4,745,051). The choice of a bacterial host for the expression of caspase-14 is dictated in part by the vector. Accordingly, commercially available vectors are paired with suitable hosts.

A wide variety of suitable vectors for expression in eukaryotic cells are also available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, the caspase-14 nucleic acid molecule is cloned into a gene targeting vector, such as pMC1neo, a pOG series vector (Stratagene Cloning Systems).

Caspase-14 polypeptides may be isolated by standard methods, such as affinity chromatography, size exclusion chromatography, metal ion chromatography, ionic exchange chromatography, HPLC, and other known protein isolation methods. (see generally Ausubel et al. supra: Sambrook et al. supra). An isolated purified protein gives a single band on SDS-PAGE when stained with Coomassie blue.

In another embodiment, chimeric caspases or protein fusion-caspases can be constructed by standard molecular biological techniques as described by Sambrook et al., supra; Ausubel et al., supra. Briefly, the region of interest of one caspase can be cloned into a cloning vector and with the aid of restriction enzymes digested such that the nucleic acid sequence of another caspase may be fused thereto, thereby creating a chimeric nucleic acid molecule encoding a chimeric protein. The same procedure can be used to create a caspase fusion protein, however, in this case many vectors are commercially available which contain fusion constructs and allow direct cloning of the insert of interest into the vector in a simple one step process.

Purified caspase-14 fusion proteins may be used in assays to screen for molecules which modulate apoptosis as described in detail infra. In further embodiments, these proteins may also be crystallized and subjected to X-ray analysis to determine the 3-dimensional structure or utilized to generate antibodies.

A recombinant caspase-14 polypeptide or functional fragment thereof can be expressed as a fusion protein with a heterologous "tag" for convenient isolation from bacterial or mammalian host proteins. For example, a histidine-tagged recombinant caspase-14 polypeptide can be isolated by nickel-chelate chromatography. Similarly, a glutathione-S-transferase tag or an antigenic tag such as "FLAG," "AU" or a myc epitope tag also can be included in a recombinant caspase-14 polypeptide or functional fragment thereof (Sambrook et al., *Molecular Cloning: A Laboratory Manual,* Cold Spring Harbor Laboratory Press, New York (1989)). PINPOINT (Promega Corp.; Madison Wis.) is a commercially available system for expression of a caspase-14 polypeptide or functional fragment thereof as a fusion protein with a heterologous biotinylated peptide.

A functional fragment of a caspase-14 polypeptide also can be produced. for example, by chemical or proteolytic cleavage of an isolated caspase-14 polypeptide. Methods for chemical and proteolytic cleavage and for purification of the resultant polypeptide fragments are well known in the art (Deutscher, supra, 1990).

A caspase-14 polypeptide or functional fragment thereof can be part of a heterodimer or a heterotetrameric apoptotic complex. Conversely, a caspase-14 inhibitor such as the large subunit of caspase-14 that lacks the active site QACRG (SEQ ID NO:3; positions 134–138 of SEQ ID NO:2; positions 130–134 of SEQ ID NO:5), for example, can bind the small subunit of caspase-14 and prevent an active protease complex from forming. Thus, a caspase-14 polypeptide or functional fragment thereof can be screened, for example, for apoptotic activity and a caspase-14 inhibitor can be screened for anti-apoptotic activity. Apoptotic activity is the ability either alone, or in combination with another molecule, to produce cell death accompanied by at least one of the morphological or biochemical alterations characteristic of apoptosis. Morphological alterations characteristic of apoptosis are well known in the art and include, for example, condensed and rounded cellular morphology; membrane blebbing; the formation of apoptotic bodies, which are membrane-bound bodies containing cytoplasmic and nuclear components; and condensation of the nucleus, with cytoplasmic organelles being relatively well maintained (Cohen, Gerald. supra, 1997; Studzinski (Ed.), *Cell Growth and Apoplosis,* Oxford: Oxford University Press (1995)). Biochemical alterations characteristic of apoptosis also are well known in the art. The classical biochemical alteration characteristic of apoptosis is the appearance of oligonucleosome-sized fragments of DNA, which produce a "ladder" upon agarose gel electrophoresis. This extensive fragmentation can be preceded by an earlier endonucleolytic cleavage of chromatin, producing DNA fragments of about 50 kb to 300 kb in size.

A variety of assays for determining whether a caspase-14 polypeptide or functional fragment thereof has apoptotic activity or whether a caspase-14 inhibitor has anti-apoptotic activity are well known in the art. Such methods include light microscopy for determining the presence of one or more morphological characteristics of apoptosis, such as condensed or rounded morphology, shrinking and blebbing of the cytoplasm, preservation of structure of cellular organelles including mitochondria, and condensation and margination of chromatin.

A caspase-14 polypeptide or functional fragment thereof or a caspase-14 inhibitor also can be assayed for respective apoptotic or anti-apoptotic activity using terminal deoxytransferase-mediated (TdT) dUTP biotin nick end-labeling (TUNEL) (Gavriel et al., *J. Cell Biol.* 119:493 (1992); Gorczyca et al., *Int. J. Oncol.* 1:639 (1992); Studzinski, supra, 1995). APOPTAG (ONCOR, Inc.; Gaithersburg Md.) is a commercially available kit for identification of apoptotic cells using digoxygenin labeling. In addition, a caspase-14 polypeptide or functional fragment thereof or a caspase-14 inhibitor can be assayed for respective apoptotic or anti-apoptotic activity by detecting nucleosomal DNA fragments using agarose gel electrophoresis (Studzinski, supra, 1995; Gong et al., *Anal. Biochem.* 218:314(1994)).

DNA filter elution methodology also can be used to detect apoptosis-associated DNA fragmentation and to determine apoptotic or anti-apoptotic activity (Studzinski, supra, 1995; Bertrand et al., *Drug Devel.* 34:138 (1995)). Apoptotic or anti-apoptotic activity also can be detected and quantitated by determining an altered mitochondrial to nuclear DNA ratio as described in Tepper et al., *Anal. Biochem.* 203:127 (1992) and Tepper and Studzinski, *J. Cell Biochem.* 52:352 (1993). One skilled in the art understands that these, or other assays for apoptotic or anti-apoptotic activity, can be performed using routine methodology.

In another embodiment, the invention provides antibodies that specifically bind to caspase-14-specific epitopes. Such caspase-14-specific epitopes are present in caspase-14 polypeptides and functional fragments thereof but not in other caspase polypeptides. Antibodies that bind caspase-14-specific epitopes readily are identified by their inability to cross react with other caspases, ced-3 and the like.

A caspase-14 polypeptide or functional fragment thereof can comprise an immunogenic amino acid sequence or, if haptenic, can be conjugated to another molecule to become immunogenic, as described below. Thus, a caspase-14 polypeptide or functional fragment thereof can be useful for eliciting production of an anti-caspase-14 antibody. In addition, the invention provides a cell line producing an anti-caspase-14 antibody.

As used herein, the term "antibody" is used in its broadest sense to include polyclonal and monoclonal antibodies, as well as antigen binding fragments of such antibodies. With regard to an anti-caspase-14 antibody of the invention, the term "antigen" means a caspase-14 polypeptide or a functional fragment thereof. An anti-caspase-14 antibody, or antigen binding fragment of such an antibody, is characterized by having specific binding activity for a caspase-14-specific epitope of at least about $1 \times 10^5$ $M^{-1}$, generally at least about $1 \times 10^6$ $M^{-1}$ and preferably at least about $1 \times 10^8$ $M^{-1}$. Fab, $F(ab')_2$, Fd and Fv fragments of an anti-caspase-14 antibody, which retain specific binding activity for a caspase-14-specific epitope, are encompassed within the anti-caspase-14 antibody of the invention.

In addition, the term "antibody" as used herein includes naturally occurring antibodies as well as non-naturally occurring antibodies, including, for example, single chain antibodies, chimeric. bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (Huse et al., *Science* 246:1275–1281 (1989)). These and other methods of making, for example, chimeric, humanized, CDR-grafted, single chain, and bifunctional antibodies are well known in the art (Winter and Harris, *Immunol. Today* 14:243–246 (1993): Ward et al., *Nature* 341:544–546 (1989); Harlow and Lane, *Antibodies: A Laboratory Manual,* Cold Spring Harbor Laboratory, New York (1992); Borrabeck, *Antibody Engineering,* 2d ed., Oxford Univ. Press (1995); Hilyard et al., *Protein Engineering A practical approach,* IRL Press (1992)).

An anti-caspase-14 antibody can be raised using as an immunogen such as, for example, an isolated caspase-14 polypeptide such as SEQ ID NOS:2 or 5, which can be prepared from natural sources or produced recombinantly, as described above, or a functional fragment of a caspase-14 polypeptide, including synthetic peptides, as described above. A non-immunogenic peptide portion of a functional fragment of a caspase-14 polypeptide can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (Harlow and Lane, supra, 1992).

An anti-caspase-14 antibody is useful, for example, for determining the presence or level of caspase-14 in a tissue sample, which can be a cell lysate or a histological section. The identification of the presence or level of caspase-14 in a sample can be made using well known immunoassay and immunohistochemical methods (Harlow and Lane, supra, 1992). In addition, an anti-caspase-14 antibody can be used in a screening assay to identify agents that modulate the activity of caspase-14 or that modulate the binding of caspase-14 to a second protein.

A particularly useful anti-caspase-14 antibody is one that binds a caspase-14 polypeptide, such as SEQ ID NOS:2 or 5, but not to either the large or small subunit cleavage products of the caspase-14 polypeptide, such as amino acid positions 1 to 156 and 163 to 257 of SEQ ID NO:2 or 1 to 146 and 147 to 242 of SEQ ID NO:5, respectively, as well as the corresponding large and small subunits of splice variant isoforms. Similarly, an antibody that binds to either the large subunit or the small subunit of a caspase-14 polypeptide, but not to the other subunit or the caspase-14 polypeptide, as well as an antibody that binds to a heterodimer comprising the large subunit and the small subunit of a caspase-14 polypeptide or a heterotetramer, but not to the caspase-14 polypeptide, is useful. An antibody that binds a caspase-14 polypeptide is useful to isolate caspase-14 from a sample, whereas an antibody that binds the large subunit or the small subunit of a caspase-14 polypeptide is useful to identify samples with caspase-14 processing activity. An antibody that binds a caspase-14 subunit heterodimer or heterotetramer is useful to isolate caspase-14 with apoptotic activity or in a screening assay to identify, for example, an agent that inhibits heterodimer or heterotetramer formation and, therefore, apoptosis. For convenience, reference herein to an anti-caspase-14 antibody generally includes all such antibodies, although the skilled artisan will recognize that the choice of a particular antibody will depend on the purpose for which the antibody will be used.

A kit incorporating an anti-caspase-14 antibody can be particularly useful. Such a kit can contain, in addition to an anti-caspase-14 antibody, a reaction cocktail that provides the proper conditions for performing the assay, control samples that contain known amounts of caspase-14 or other appropriate caspase-14 antigen recognized by the antibody and, if desired, a second antibody specific for the anti-caspase-14 antibody. Such an assay also can include a simple method for detecting the presence or amount of caspase-14 in a sample that is bound to the anti-caspase-14 antibody.

An anti-caspase-14 antibody, as well as a caspase-14 polypeptide or functional fragment thereof, can be labeled so as to be detectable using methods well known in the art (Hermanson, *Bioconjugate Techniques,* Academic Press (1996); Harlow and Lane, supra, 1992). For example, an anti-caspase-14 antibody can be labeled with various detectable moieties including a radiolabel, an enzyme, biotin or a fluorochrome. Reagents for labeling an anti-caspase-14 antibody can be included in a kit containing the antibody or can be purchased separately from a commercial source.

Following contact, for example, of a labeled antibody with a sample such as a tissue homogenate or a histological section of a tissue, specifically bound labeled antibody can be identified by detecting the particular moiety. Alternatively, a labeled second antibody can be used to identify specific binding of an unlabeled anti-caspase-14 antibody. A second antibody generally will be specific for the particular class of the first antibody. For example, if an anti-caspase-14 antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, which is an anti-caspase-14 antibody, then the sample is contacted with the labeled second antibody, which specifically binds to the anti-caspase-14 antibody and results in a labeled sample.

Methods for raisin, polyclonal antibodies, for example, in a rabbit, goat, mouse or other mammal, are well known in the art. In addition, monoclonal antibodies can be obtained using methods that are well known and routine in the art (Harlow and Lane, supra, 1992). For example, spleen cells from a caspase-14-immunized mammal can be fused to an appropriate myeloma cell line such as SP/02 myeloma cells to produce hybridoma cells. Cloned hybridoma cell lines can be screened using a labeled caspase-14 polypeptide or functional fragment thereof to identify clones that secrete anti-caspase-14 monoclonal antibodies having the desired specificity. Hybridomas expressing anti-caspase-14 monoclonal antibodies having a desirable specificity and affinity can be isolated and utilized as a continuous source of the antibodies, which are useful, for example, for preparing standardized kits as described above. Similarly, a recombinant phage that expresses, for example, a single chain anti-caspase-14 also provides a monoclonal antibody that can used for preparing standardized kits.

A monoclonal anti-caspase-14 antibody can be used to prepare anti-idiotypic antibodies, which present an epitope that mimics a caspase-14-specific epitope recognized by the monoclonal antibody used to prepare the anti-idiotypic antibodies. Where the epitope mimicked includes, for example, a portion of the caspase-14 catalytic domain. the anti-idiotypic antibody can act as a competitor of caspase-14 and, therefore, can be useful for reducing the level of activity of caspase-14 and, consequently, the level of apoptotic activity. Thus, the invention further provides an anti-idiotypic anti-caspase-14 antibody, which mimics a caspase-14-specific epitope, such as an epitope of SEQ ID NOS:2, 5, 7. or 9, an epitope of the large or small subunit of a caspase-14 polypeptide or an epitope of a caspase-14 heterodimer or heterotetramer.

The invention also provides an isolated nucleic acid molecule encoding a caspase-14 polypeptide or functional fragment thereof. The term "isolated" means in a form that is relatively free from contaminating lipids, polypeptides, unrelated nucleic acid molecules and other cellular material normally associated with the nucleic acid molecule in the cell and at least 30% of the total material. In other embodiments of the invention, the nucleic acid molecule is 50% or 70% of the total material. In other embodiments of the invention, the nucleic acid molecule is 90% or 95% of the total material. In yet another embodiment of the invention the nucleic acid molecule is greater than 95% of the total material. Thus, an isolated nucleic acid molecule of the invention is one that is in a form that is different from the naturally occurring state.

One exemplary nucleic acid molecule of the invention is provided by SEQ ID NO:1, which is 850 nucleotides in length and encodes SEQ ID NO:2 (see FIG. 1). Another exemplary nucleic acid molecule is provided by SEQ ID NO:4. which is 777 nucleotides in length and encodes SEQ ID NO:5 (see FIG. 7). Additional nucleic acid molecules of the invention are those that have an oligonucleotide or polynucleotide sequence that encodes SEQ ID NOS:2 or 5 or a functional fragment thereof. In addition, the invention provides nucleic acid molecules that have an oligonucleotide or polynucleotide sequence that encodes a caspase-14 polypeptide or a functional fragment thereof such as SEQ ID NOS:6 and 8.

Such an oligonucleotide or polynucleotide sequence also can be useful, for example, as a probe or a PCR primer. Such probes can be used to screen a genomic DNA library or a cDNA library to obtain other nucleic acid molecules encoding caspase-14 polypeptides or to diagnose a disease associated with enhanced or inhibited apoptosis (see below). Thus, the invention provides oligonucleotide sequences that comprise at least 12 contiguous nucleotides of SEQ ID NOS:1, 4, 6, or 8. In other embodiments, the invention provides oligonucleotide sequences that comprise at least 15, 18 or 21 contiguous nucleotides of SEQ ID NOS:1, 4, 6, or 8. In another embodiment, the invention provides a nucleic acid molecule encoding SEQ ID NOS:2, 5, or splice variants thereof. In yet another embodiment, the invention provides a nucleic acid molecule encoding a caspase-14 polypeptide. Oligonucleotide sequences consisting of nucleotide positions 454 to 474 or positions 460 to 477 of SEQ ID NO:1, or nucleotide positions 430 to 450 or positions 436 to 453 of SEQ ID NO:4 and/or homologous positions of splice variant forms, or any contiguous portion thereof, however, are not encompassed within the nucleic acid molecules of the invention. Similarly. nucleic acid molecules that consist of the expressed sequence tag having GenBank accession number AA103647, or any contiguous portion thereof, also are not encompassed within the nucleic acid molecules of the invention.

In another embodiment, the invention provides an isolated gene encoding caspase-14, as well as functional fragments of a caspase-14 gene. A gene encoding caspase-14 can be obtained by screening a genomic library using, for example, an oligonucleotide or polynucleotide sequence of SEQ ID NOS: 1, 4, 6, or 8 as a probe, as discussed above. Methods of preparing genomic libraries are known in the art (Perbal, Bernard, *A Practical Guide to Molecular Cloning*, John Wiley & Sons, Inc. (1 988), ch. 17, and the various references cited therein).

In addition, nucleic acid molecules that do not encode a caspase-14 gene product but, instead, are regulatory elements are considered part of the gene encoding caspase-14, particularly functional fragments of a caspase-14 gene. Specific examples of such functional fragments of a caspase-14 gene include promoters, enhancers and other gene expression regulatory elements present in a caspase-14 encoding gene. Thus, upon obtaining a caspase-14 gene, as described above, regulatory elements present in the caspase-14 gene can be identified using routine methods.

To identify sequences having homology to the caspase family of proteases, nucleic acid molecules encoding apoptotic cysteine proteases can be enriched by PCR amplification of a cDNA library using a primer designed to encompass homologous regions in nucleic acid sequences that encode known caspase protease family members. The enriched library can be further amplified by PCR using a primer with sequences having homology to the putative novel protease cDNA but not to the other caspase family of proteases. For example, to obtain a caspase-14 polypeptide, such as a mammalian homologue of SEQ ID NOS:2, 5, 7, or 9, a primer with sequences homologous to SEQ ID NOS:1, 4, 6, or 8, respectively, but not to the other caspases can be used.

As searching a genetic data base will yield homologous sequence matches to any query nucleotide sequence, additional criteria must be used to identify authentic caspase homologs from non-specific matches. Caspase family members share the highest degree of homology in the active site and catalytically important amino acid residues (FIG. 2). A given EST returned by a search may not necessarily include one of these highly homologous sites but, rather, may only include a region within the protease having cryptic homology. Confirming an EST as encoding part of a novel caspase protease involves translation of all the positive EST hits in three different reading frames and subsequent identification of conservative active site or catalytically important amino acid sequence motifs. Then, using conventional cDNA cloning, a full length cDNA of the putative novel protease can be obtained and 1) analyzed for overall structural homology to caspase family members, 2) recombinantly expressed and analyzed for cysteine protease activity, and 3) analyzed for the induction of apoptosis by heterologous expression of the cDNA in appropriate cells.

Alternative methods for isolating a caspase-14 encoding nucleic acid molecule also can be employed. For example, using the teachings described herein, those skilled in the art can routinely isolate and manipulate caspase-14 nucleic acid molecules using well known methods. All that is necessary is a disclosed sequence of a caspase-14 encoding nucleic acid molecule, for example, SEQ ID NOS:1, 4, 6, or 8, or its deduced amino acid sequence, for example, SEQ ID) NOS:2, 5, 7, or 9, respectively. Such methods include, for example, screening a cDNA or genomic library by using synthetic oligonucleotides, nucleic acid fragments or primers as hybridization probes. Alternatively, antibodies to a caspase-14 polypeptide or functional fragment thereof, particularly to a caspase-14-specific epitope, can be generated and used to screen an expression library to isolate caspase-14 encoding nucleic acids.

The above described methods are known to those skilled in the art (Sambrook et al., supra, 1989, and the various references cited therein; Ansubel et al., *Current Protocols in Molecular Biology*, John Wiley and Sons, Baltimore, Md., Supp. 39 (1997)). Furthermore, recombinant DNA methods currently used by those skilled in the art include the polymerase chain reaction (PCR), which, combined with the caspase-14 nucleotide and amino acid sequences described herein, allows reproduction of caspase-14 encoding sequences. Desired sequences can be amplified exponentially starting from as little as a single gene copy by means of PCR. The PCR technology is the subject matter of U.S. Pat. Nos. 4,683,195, 4,800,159, 4,754,065, and 4.683,202.

A caspase-14 nucleic acid molecule of the invention, as well as a caspase-14 polypeptide or functional fragment thereof, can be used to diagnose, or to generate reagents to diagnose. pathological conditions associated with increased or decreased levels of apoptosis. Such methods of diagnosis include using a nucleic acid probe, which can hybridize with a caspase-14 containing nucleotide sequence, or using an antibody or ligand, which binds a caspase-14 polypeptide. Methods of diagnosis further include detecting caspase-14 enzymatic activity in a sample (see Example 2). Such methods, which are disclosed herein or otherwise known in the art, can be performed ex vivo, for example, by removing a cell or tissue sample from an individual exhibiting or suspected of having a pathological condition associated with increased or decreased levels of apoptosis. Correlation of increased caspase-14 expression or activity, as compared to normal levels of caspase-14, which can be determined by taking samples from apparently normal individuals, is indicative of a disease associated with increased levels of apoptosis, whereas correlation of decreased caspase-14 expression or activity is indicative of a disease associated with decreased levels of apoptosis. As used herein, reference to "increased" or "decreased" expression or activity of caspase-14 or "increased" or "decreased" levels of apoptosis means at least about one standard deviation and, preferably, at least about two standard deviations, above or below, respectively, the normal expression or activity or levels of caspase-14 in a corresponding sample of a normal individual.

A caspase-14 encoding nucleic acid of the invention, as well as a caspase-14 polypeptide or functional fragment thereof, can be used to reduce the severity of a pathological condition characterized, in part, by increased or decreased levels of apoptosis. A caspase-14 polypeptide or functional fragment thereof that includes, for example, the catalytic domain of caspase-14 can be formulated into a pharmaceutical composition and, therefore, can be used as a medicament. Such a medicament is useful in the treatment of an individual having a disease characterized, in part, by decreased levels of apoptosis, which is associated with increased cell survival and proliferation. Such a caspase-14 polypeptide or functional fragment thereof can increase the levels of apoptosis in an individual with such a disease and, thereby, decrease cell survival and proliferation. Examples of pathological conditions associated with decreased levels of apoptosis and, therefore, increased cell survival include cancers such as lymphomas and hormone dependent tumors such as breast, prostate and ovarian cancer, autoimmune diseases such as systemic lupus erythematosus, immune-mediated glomeruloncphritis and viral infections such as herpesvirus, poxvirus and adenovirus.

Additionally, molecules that interact with caspase-14, directly or indirectly, to induce caspasc-14 mediated apoptosis can be used to treat such a disease. Such molecules that interact directly with caspase-14 can be identified based on their physical association with caspase-14 using, for example, an affinity matrix comprising caspase-14 or a method such as the two hybrid assay (U.S. Pat. No. 5,283,173).

To be effective, caspase-14 polypeptides or functional fragments thereof must be introduced into cells characterized by decreased levels of apoptosis. Introduction can be accomplished by a variety of means known in the art including, for example, using lipid vesicles or receptor mediated endocytosis. Targeting the appropriate cell type also can be accomplished by conjugating the caspase-14 polypeptide or functional fragment thereof to a specific receptor ligand or a target cell specific antibody, producing a caspase-14 fusion protein comprising the ligand or antibody.

In contrast to the induction of caspase-14 mediated apoptosis for the treatment of pathological conditions characterized by increased cell survival or proliferation, inhibitors of caspase-14 can be used to treat pathological conditions associated with increased levels of apoptosis. Examples of pathological conditions associated with increased levels of apoptosis and, therefore, decreased cell survival include, for example, degenerative disorders such as Alzheimer's disease, Parkinson's disease, amyotrophic lateral sclerosis, retinitis pigmentosa, cerebellar degeneration, myelodysplastic syndromes such as aplastic anemia and ischemic injury, including myocardial infarction, stroke and reperfusion injury.

Such inhibitors of caspase-14 can be, for example, inhibitors of the caspase-14 protease activity or inhibitors of the conversion of the inactive, proenzyme into the active caspase-14 protease. Specific examples of such inhibitors can include. for example, anti-caspase-14 antibodies, proteins, small peptidyl protease inhibitors and small non-peptide, organic molecule inhibitors. Such inhibitors are formulated in a medium that allows introduction into the desired cell type. Alternatively, such inhibitors can be attached to targeting ligands for introduction by cell mediated endocytosis and other receptor mediated events. Specific caspase-14 peptidyl inhibitors can include suicide inhibitors and substrate analogues such as the tetrapeptide DEVD aldehyde and the cowpox virus protein Crm A, for example.

Other inhibitors of caspase-14 include, for example, small molecules or organic compounds that bind and inactivate caspase-14 by a competitive or non-competitive inhibitory type mechanism. Molecules or compounds that indirectly inhibit the caspase-14 pathway can also be used as inhibitors of caspase-14. Caspase-14 inhibitors can be identified by screening for molecules that demonstrate specific or beneficial caspase-14 inhibitory activity. Such methods are described herein and can be practiced by those skilled in the art in view of the disclosed caspase-14 nucleotide sequences and amino acid sequences.

Dominant/negative inhibitors of caspase-14 also can be used to treat or reduce the severity of pathological conditions associated with enhanced apoptosis. For example, a dominant/negative inhibitor comprising the large subunit of caspase-14, but lacking the active site QACRG (SEQ ID NO:3; positions 134–138 of SEQ ID NO:2; positions 130–134 of SEQ ID NO:5 or 7; positions 102–106 SEQ ID NO:9), can bind the small subunit of caspase-14 to form a complex that lacks protease activity. Such a mechanism of dominant negative inhibition of caspase-14 is similar to the dominant negative inhibition due to alternately spliced isoforms of caspase-2, caspase-7 and caspase-8 (Cohen. *J. Biochem.* 326:1–16 (1997)). Subunits from other caspascs similarly can be used to form dominant/negative inhibitors of caspase-14 activity and, therefore, to treat pathological conditions associated with increased levels of apoptosis. Such subunits should be selected so that they bind either the large or small subunit of caspase-14 polypeptides to prevent their assembly into active heterotetrameric protease complexes. An anti-idiotypic anti-caspase-14 antibody also can serve this purpose. Moreover, caspase-14 subunits that have been modified so as to be catalytically inactive can be used as dominant/negative inhibitors of caspase-14. Such modifications include, for example, mutation of the active site cysteine residue (amino acid position 136 of SEQ ID NO:2; amino acid position 132 of SEQ ID NO:5) to another amino acid such as alanine or glycine.

Caspase-14 substrate antagonists also can be used to treat or reduce the severity of pathological conditions associated with increased levels of apoptosis. Such substrate antagonists can bind to and inhibit cleavage by caspase-14, thereby preventing commitment progression of apoptosis. Substrate antagonists include. for example, ligands and small molecule compounds.

A caspase-14 polypeptide or functional fragment thereof, or an inhibitor of caspase-14, can be administered by conventional therapeutic methods, in dosages that are sufficient to respectively increase or decrease the levels of apoptosis in the target cells. Such dosages can be determined by those skilled in the art using, for example, Phase I and Phase II trials. Administration can be accomplished by injection, for example, intravenous, intraperitoneal or subcutaneous injection, and can be performed in a variety of different regimes, including single high dose administration, repeated small dose administration or a combination of both. The dosing will depend on the cell type, progression of the pathological condition and the overall health of the individual.

Treatment or reduction of the severity of pathological conditions associated with increased or decreased levels of apoptosis also can be accomplished by introducing expressible nucleic acid molecules encoding respectively caspase-14 polypeptides or functional fragments thereof or caspase-14 inhibitors such as antisense caspase-14 nucleic acid molecules into cells characterized by such pathological conditions. For example, treatment to reduce the severity of a pathological condition associated with decreased levels of apoptosis can be accomplished by elevating the synthesis rates of caspase-14 using recombinant caspase-14 expression vectors and gene transfer technology. Conversely, treatment or reduction of the severity of pathological conditions associated with increased levels of apoptosis can be accomplished by introducing and expressing antisense caspase-14 nucleic acid molecules, which inhibit endogenous caspase-14 expression. Such methods of introduction and expression are well known in the art and described below with reference to recombinant viral vectors. Other vectors compatible with the appropriate targeted cell can accomplish the same goal and can be substituted in the methods described herein in place of recombinant viral vectors.

Further embodiments include the inhibition of neoplasia or apoptosis by utilizing specific antisense polynucleotides complementary to all or part of the nucleic acid sequences SEQ ID NOS:1, 4, 6, or 8 encoding a caspase-14. Such complementary antisense polynucleotides may include substitutions, additions, deletions, or transpositions, as long as specific hybridization to the relevant target sequence in SEQ ID NOS:1, 4, 6, or 8 is retained as a functional property of the polynucleotide. Antisense polynucleotides that prevent transcription and/or translation of mRNA corresponding to caspase-14 may inhibit apoptosis. Antisense polynucleotides of various lengths may be produced and used, however, the sequence length is typically at least 20 consecutive nucleotides that are substantially or wholly identical to the sequence of SEQ ID NOS: 1,3, 4, 6, or 8. (see U.S. Pat. No. 5,691,179 and *Antisense RNA and DNA,* D. A. Melton, Ed., Cold Spring Harbor Laboratory, Cold Spring Harbor, N.Y. 1988. each of which is incorporated herein by reference).

Recombinant viral vectors are useful for in vivo expression of a desired nucleic acid molecule because such vectors can offer advantages such as lateral infection and targeting specificity. Lateral infection is inherent in the life cycle of viral vectors such as retroviruses and is the process by which a single infected cell produces many progeny virions that bud off and infect neighboring cells. Lateral infection can result in rapid infection of a large area, most of which were not initially infected by the original viral particles. Viral vectors that are unable to spread laterally can be useful where it is not necessary to introduce a specified gene into all of the targeted cells.

Typically, viruses infect and propagate in specific cell types. Therefore, viral vectors are useful for specifically introducing a desired gene into predetermined cell types. The vector to be used in the methods of the invention will depend on desired cell type to be targeted. For example, if neurodegenerative diseases are to be treated by decreasing the caspase-14 activity of affected neuronal cells, then a vector specific for cells of the neuronal cell lineage, for example herpesvirus based vectors, should be used (Kaplitt and Loewy, *Viral Vectors,* Academic Press, Inc. (1995)). Similarly, if diseases or pathological conditions of the hematopoictic system are to be treated, then a viral vector such as an HIV based vector that is specific for blood cells and their precursors, preferably for a specific type of hematopoictic cell, should be used. Moreover, such vectors can be modified with specific receptors or ligands to modify target specificity through receptor mediated events. These modification procedures can be performed by recombinant DNA techniques or synthetic chemistry procedures or the like. The specific type of vector will depend upon the intended application. Thus, the invention provides a vector that contains a nucleic acid molecule encoding a caspase-14 polypeptide or functional fragment thereof. As described herein, vectors of the invention can be used in an appropriate host cell. Thus, the invention provides a cell containing a vector of the invention. Vectors of the invention are known and readily available within the art or can be constructed by one skilled in the art using well known methodology.

A vector of the invention, such as one encoding a caspase-14 polypeptide or an inhibitor of caspase-14, for example, an antisense nucleic acid molecule, can be administered in several ways to obtain expression of such a sequence, which can increase or decrease, respectively, the level of activity of caspase-14 in the cells affected by the disease or pathological condition. If a viral vector is used, the procedure can take advantage of their target specificity and, consequently, a vector does not necessarily have to be administered locally at the diseased site. However, local administration can provide a quicker and more effective treatment. Administration can be performed by conventional methods, for example, intravenous or subcutaneous injection into the subject. Injection of a viral vector into the spinal fluid also can be used as a mode of administration, especially in the case of neurodegenerative diseases of the central nervous system. Following injection, the viral vector will bind to a target cell expressing an appropriate receptor.

A caspase-14 encoding vector can be administered locally at the site of the disease or pathological condition. Local administration is advantageous because there is no dilution effect and, therefore, a smaller dose is required to achieve caspase-14 expression in a majority of the targeted cells. Additionally, local administration can alleviate the targeting requirement of other forms of administration, since a vector can be used that infects all cells in the locally administered area. If expression is desired in only a specific subset of cells within the administered area, then promoter and expression elements that are specific for the desired subset can be incorporated in the vector, which can be a viral vector, viral genome, plasmid or phagemid. A transfection vehicle such as a liposome can be used to introduce the vector into recipient cells within the inoculated area. Such transfection vehicles are known by those skilled in the art. Alternatively, the vector can be administered directly into a tissue of an individual (Wolff et al., *Science* 247:1465–1468 (1990)).

Additional features can be added to a vector to ensure safety and/or enhance therapeutic efficacy. Such features include, for example, markers that can be used to negatively select against cells infected with the recombinant virus. An example of such a negative selection marker is the TK gene that confers sensitivity to the antibiotic gancyclovir. Negative selection is a means by which infection can be controlled because it provides inducible suicide through the addition of antibiotic.

Additionally, a caspase-14 encoding nucleic acid molecule of the invention, as well as a caspase-14 polypeptide or functional fragment thereof, can be used to screen for pharmaceutical compounds and macromolecules that modulate, that is, inhibit or enhance, caspase-14 activity. Such a caspase-14 encoding nucleic acid molecule, caspase-14 polypeptide or functional fragment thereof can be used in a sample to screen for inhibitors of caspase-14, including those that inhibit enzymatic or apoptotic activity. Alternatively, a caspasc-14 encoding nucleic acid molecule, caspase-14 polypeptide or functional fragment thereof can be used in a sample to screen for compounds that enhance caspase-14 activity such as by inducing cleavage of the caspase-14 proenzyme into its active subunits. Such a sample can contain a cell lysate and also can contain isolated caspase-14 encoding nucleic acid molecules. caspase-14 polypeptides or functional fragments thereof.

Candidate inhibitors and enhancers may be isolated or procured from a variety of sources, such as bacteria, fungi, plants, parasites, libraries of chemicals, peptides or peptide derivatives and the like. Inhibitors and enhancers may be also be rationally designed, based on the protein structure determined from X-ray crystallography (see, Mittl et al., *J. Biol. Chem.*, 272:6539–6547, 1997). In certain preferred embodiments, the inhibitor targets a specific caspase (e.g.. caspase-3 and not any other caspases).

Without being held to a particular mechanism, the inhibitor may act by preventing processing of caspase or by preventing enzymatic activity, or by other mechanism. The inhibitor may act directly or indirectly. In preferred embodiments, inhibitors interfere in the processing of the caspase protein. In other preferred embodiments, the inhibitors are small molecules. In a most preferred embodiment, the inhibitors prevent apoptosis. Inhibitors should have a minimum of side effects and are preferably non-toxic. Inhibitors that can penetrate cells are preferred.

In addition, enhancers of caspase activity or expression are desirable in certain circumstances. At times, increasing apoptosis will have a therapeutic effect. For example, tumors or cells that mediate autoimmune diseases are appropriate cells for destruction. Enhancers may increase the rate or efficiency of caspase processing, increase transcription or translation, or act through other mechanisms. As is apparent to one skilled in the art, many of the guidelines presented above apply to the design of enhancers as well.

Screening assays for inhibitors and enhancers will vary according to the type of inhibitor or enhancer and the nature of the activity that is being affected. Assays may be performed in vitro or in vivo. In general, in vitro assays are designed to evaluate caspase protein processing or caspase enzymatic activity, and in vivo assays are designed to evaluate caspase protein processing, caspase enzymatic activity, apoptosis, or caspase cleavage of substrate. In any of the assays, a statistically significant increase or decrease compared to a proper control is indicative of enhancement or inhibition.

One type of in vitro assay can be performed by examining the effect of a candidate compound on the processing of caspase-14 into two subunits. Briefly, a caspase-14, that is a primary translation product, is obtained from an in vitro translation system. The caspase-14 is preferably constructed to be capable of normal auto-processing, but can be constructed to be cleaved by other protease components present or added to the reaction. This primary product is contacted with or without, or translated in the presence or absence of a candidate compound and assessed for appearance of the two subunits. To facilitate detection, typically, the caspase-14 is labeled during translation. The two subunits may be readily detected by autoradiography after gel electrophoresis. One skilled in the art will recognize that other methods of labeling and detection may be used alternatively.

An alternative in vitro assay is designed to measure cleavage of a caspase substrate (e.g., Acetyl DEVD-aminomethyl coumarin (amc), lamin, PRPP, and the like). Substrate turnover may be assayed using either cleavable or noncleavable rev-caspase. Briefly, in this method, caspase-14 is translated and allowed sufficient time to be processed or subjected to a protease which activates caspase-14. The caspase substrate along with the candidate compound is added to the reaction. Detection of cleaved substrate is performed by any one of a variety of standard methods. Generally, the substrate will be labeled and followed by an appropriate detection means.

Moreover, any known enzymatic analysis can be used to follow the inhibitory or enhancing ability of a candidate compound with regard to a caspase-14 of this invention. For example, one could express caspase-14 in a cell line be it bacterial, insect, mammalian or other, and purify the caspase. The purified caspase-14 could then be used in a variety of assays to follow its catalytic ability in the presence of candidate compounds, as noted above. Such methods of expressing and purifying recombinant proteins are known in the art and examples can be found in Sambrook et al., *Molecular Cloning, A Laboratory Manual,* Cold Spring Harbor Press, 1989 as well as in a number of other sources.

In vivo assays are typically performed in cells transfected either transiently or stably with an expression vector containing a caspase-14 gene, such as those described herein. These cells are used to measure caspase-14 processing. substrate turnover or apoptosis in the presence or absence of a candidate compound. When assaying apoptosis, a variety of cell analyses may be used including, for example, dye staining and microscopy to examine nucleic acid fragmentation and porosity of the cells. Further. in vivo assaying for the ability of the transfected caspase-14 to cleave known substrates that are co-transfected or placed in the cell culture media in the presence of the candidate compound can be performed thereby allowing for the detection and determination of substrate turnover.

The assays briefly described herein may be used to identify an enhance or inhibitor that is specific for an individual caspase. In a preferred embodiment candidate compounds would be analyzed using a variety of caspases (erg., caspase-1 through caspase-14) to identify specific inhibitors and enhancers for individual caspases.

A variety of methodologies exist can be used to investigate the effect of a candidate compound. Such methodologies are those commonly used to analyze enzymatic reactions and include, for example, SDS-PAGE, spectroscopy, HPLC analysis, autoradiography, chemiluminescence. chromogenic reactions, and immunochemistry (e.g., blotting, precipitating, etc.).

Inhibitors and enhancers may be used in the context of this invention to exert control over the cell death process or cytokine activation. Thus, these inhibitors and enhancers will have utility in diseases characterized by either excessive or insufficient levels of apoptosis. Inhibitors of caspase proteases have potential to treat the major neurodegenerative diseases: stroke, Parkinson's Disease, Alzheimer's Disease, and ALS. As well, caspase-14 protease inhibitors may be used to inhibit apoptosis in the heart following myocardial infarction, in the kidney following acute ischemia, and in diseases of the liver. Enhancers of caspase-14 activity may be used in contexts when apoptosis or cytokine activation are desired. For example, inducing or increasing apoptosis in cancer cells or aberrantly proliferating cells may be effected by delivery of a caspase enhancer.

Such screening methods are known to those skilled in the art and can be performed by either in vitro or in vivo procedures. For example. Example 2 provides a specific in vitro assay for caspase-14 protease activity. This assay employs a sample containing a caspase-14 polypeptide expressed in an active, processed form recombinantly in *E. coli*. The protease activity of the polypeptide is measured by incubation with a fluorescent substrate. This assay can be used to screen synthetic or naturally occurring compound libraries, including macromolecules, for agents that either inhibit or enhance caspase-14 activity. The caspase-14 polypeptides or functional fragments thereof to be used in the assay can be obtained by, for example, in vitro translation, recombinant expression or biochemical procedures. Methods other than that described in Example 2 also can be used to screen and identify compounds that inhibit or enhance caspase-14 activity including, for example, those described supra and other methodologies such as using phage display peptide libraries, where greater than $10^8$ peptide sequences can be screened in a single round of panning. Such methods, as well as others, are known in the art and can be utilized to identify compounds that inhibit or enhance caspase-14 activity.

As noted above, caspase-14 nucleic acid molecules may be delivered to cells in combination with a vector or other gene delivery vehicle. These methods may be accomplished by delivery of DNA or cDNA capable of in vivo transcription caspase-14 or an active fragment thereof. More specifically, in order to produce caspase-14 in vive, a nucleic acid sequence coding for caspase-14 is placed under the control of a eukaryotic promoter (e.g., a pol III promoter, CMV or SV40 promoter). Where it is desired to more specifically control transcription, the caspase-14 encoding nucleic acid molecule may be placed under the control of a tissue or cell specific promoter (e.g., to target cells in the liver), or an inducible promoter, such as MMTV LTR, CMV IE promoter, RSV LTR, SV40, metallothionein promoter (see, e.g., U.S. Pat. No. 4,870,009), ecdysone response element system, tetracycline-reversible silencing system (tet-on, tet-off), and the like.

Many techniques for introduction of nucleic acids into cells are known. Such methods include retroviral vectors and subsequent retrovirus infection, adenoviral or adeno-associated viral vectors and subsequent infection, and complexes of nucleic acid with a condensing agent (e.g., polylysine). These complexes or viral vectors may be targeted to particular cell types by way of a ligand incorporated into the vehicle. Many ligands specific for tumor cells and other cells are well known in the art.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner el al., *Cell* 75(2):207–216, 1993; Li et al., *Hum Gene Ther.* 4(4):403–409, 1993; Caillaud et al., *Eur. J Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218.

Within certain aspects of the invention, nucleic acid molecules that encode caspase-14 may be introduced into a host cell utilizing a gene delivery vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et. al., *Proc. Natl. Acad Sci. USA* 84:7413–7417, 1989), micro-projectile bombardment (Williams et al., *PNAS* 88:2726–2730, 1991), polycation compounds such as polylysine, receptor specific ligands, liposomes entrapping the nucleic acid molecules spheroplast fusion whereby *E. coli* containing the nucleic acid molecules are stripped of their outer cell walls and fused to animal cells using polyethylene glycol, viral transduction, (Cline et al., *Pharmac. Ther.* 29:69. 1985; and Friedmann et al., *Science* 244:1275, 1989), and DNA ligand (Wu et at al., *J. Biol. Chem.* 264:16985–16987, 1989), as well as psoralen inactivated viruses such as Sendai or Adenovirus. In one embodiment, the caspase-14 encoding construct is introduced into the host cell using a liposome.

In an additional embodiment, the compositions of caspase-14 may be administered either alone, or as a pharmaceutical composition. These compositions may contain any of the above described inhibitors, enhancers, DNA molecules, vectors or host cells, along with a pharmaceutically or physiologically acceptable carrier. excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific scrum albumin are exemplary appropriate diluents.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate, utilizing appropriate excipients which provide stability as a lyophilizate, and subsequent to rehydration. One killed in the art may further formulate the enhancers or inhibitors of this invention in n appropriate manner, and in accordance with accepted practices. such as those isclosed in *Remington's Pharmaceutical Sciences,* Gennaro, Ed., Mack Publishing Co., Easton, Pa. 1990. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

It is understood that modifications that do not substantially affect the various embodiments of the invention also are included within the invention. Accordingly, the following examples are intended to illustrate but not limit the present invention.

EXAMPLES

Example 1

Characterization of Caspase-14

This example shows the sequencing and analysis of caspase-14.

An EST, GenBank accessionse number AA103647, was identified during a homology search of the GenBank database using a query nucleotide sequence based on caspase-3 and caspase-6 coding sequences. The EST is a sequence of 483 nucleotides in length.

The EST was derived from a mouse cell clone, which was obtained from IMAGE Consortium. The EST was resequenced, revealing that it contained numerous sequencing errors, including at nucleotide positions 13, 54 and 164 of SEQ ID NO:1, where the corresponding positions in the EST contain nothing. Full sequencing of the clone revealed a sequence of 850 nucleotides in length encoding a polypeptide (SEQ ID NO:2), designated herein as caspase-14, which is similar to members of the caspase family of proteases.

Following this characterization, amplification of a partial human caspase-14 cDNA from a human brain cDNA library was conducted. The set of forward and reverse primers derived from the mouse cDNA sequence of caspase-14 are set forth below:

Forward primer: ATATGATATGTCAGGTGCCCG (SEQ ID NO:69)

Reverse primer: TTCCGGAGGGTGCTTTGGA (SEQ ID NO:70)

To obtain the 5' and 3' coding sequences of human caspase-14 we performed RACE (rapid amplification of cDNA ends) using nested PCR primers derived from the human caspase-14 cDNA and vector specific primers complimentary the library vector.

For 5' amplification
Reverse primers: CCTGTATGATGTACACCTFTGG (SEQ ID NO:71)
AGAGATTCTCCAGCTGAC (SEQ ID NO:72)
ATCTTCTCCCTTGAGGAAG (SEQ ID NO:73)

For 3' amplification
Forward primers: ATATGATATGTCAGGTGCCCG (SEQ ID NO:74)
CMGGTGTACATCATACAGG (SEQ ID NO:75)

Following the above PCR amplification, the derived sequence (SEQ ID NO:4) and the predicted amino acid sequence (SEQ ID NO:5) were compared with the mouse sequence. The human and mouse proteins exhibit 75% identity when compared using, the GCG pileUp program (Gapweight:12, Gaplength weight:4). The pileUp program creates a multiple sequence alignment form a group of related sequences using progressive, pairwise alignments. PileUp creates a multiple sequence alignment using the progressive alignment method of Feng and Doolittle (*J Mol. Evol.* 25:351–360, 1987) and is similar to the method described by Higgins and Sharp (CABIOS 5:151–153, 1989).

Example 2

Kinetic Parameters of Caspase-14

This example provides methods to characterize the protease activity and substrate specificity of caspase-14.

The kinetic properties of bacterially expressed recombinant caspase-14 is determined using tetrapeptide substrates in a continuous fluorometric assay. Examples of two such substrates are DEVD-AMC and the YVAD-AMC, which represent the cleavage sites for the poly(ADP-ribose) polymerase (PARP) and IL-1β P1–P4 substrate tetrapeptides, respectively (Nicholson et al., *Nature* 376:37–43 (1995)). Caspase-14 cDNA lacking most of the propeptide coding sequence is subcloned in-frame into the Bam HI/XhoI sites of the bacterial expression vector pGEX-5X-3 (Pharmacia Biotech Inc.). This vector produces caspase-14 as a fusion protein with glutathione S-transferase (GST) and is used essentially as described in Fernandes-Alnemri et al., *Cancer Res.* 55:6045–605(1995). The GST-caspase-14 expression vector is constructed and transformed into DH5α bacteria using routine molecular biology methods known to those skilled in the art. After induction with IPTG, bacterial extracts are prepared from *E. coli* expressing the recombinant fusion proteins. The extracts are adsorbed to glutathione-Sepharose resin washed several times and then analyzed by SDS-PAGE.

The isolated caspase-14 GST-fusion protein is then used for further enzymatic analyses. The activity of caspase-14 is measured using bacterial lysates prepared with ICE buffer (25 mM HEPES, 1 mM EDTA, 5mM DTT, 0.1% CHAPS. 10% sucrose. pH 7.5) at room temperature (24–25° C.). The $K_i$'s are determined from the hydrolysis rate of 50 $\mu$M DEVD-AMC following a 30 min preincubation of the enzyme with inhibitors DEVD-CHO and recombinant CrmA protein. Prior to incubation with enzyme, purified CrmA is activated by incubation with 5 mM DTT for 10 min at 37° C.

Although the invention has been described with reference to the disclosed embodiments, those skilled in the art will readily appreciate that the specific experiments detailed are only illustrative of the invention. It should be understood that various modifications can be made without departing from the spirit of the invention.

Example 3

Overexpression of Procaspase-14 in MCF-7 Cells

Figure 4:
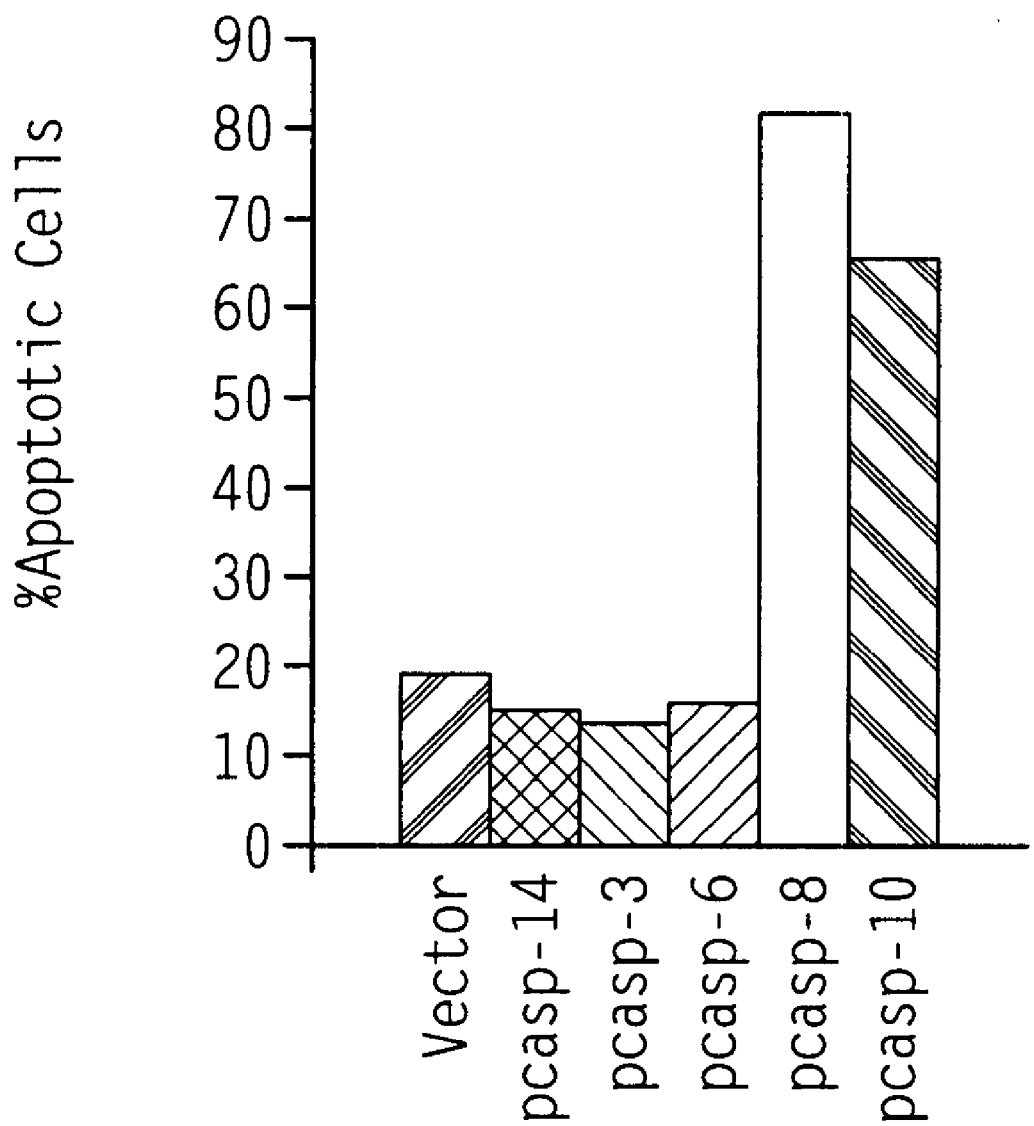
FIG. 4 is a bar diagram representing the ability of procaspase-14 overexpression in MCF-7 cells to initiate apoptosis.

Overexpression of small prodomain executioner procaspases such as procaspase-3 or -6 in mammalian cells does not induce apoptosis, due to their inability to autoprocess themselves. On the other hand overexpression of the large prodomain initiator procaspases such as procaspase-8 can induce apoptosis, due to their ability to undergo prodomain-mediated oligomerization. To test the ability of procaspase-14 to induce apoptosis in transfected cells. MCF-7 cells were transiently transfected with procaspase-14 in a PRSC lac-Z expression construct under the CMV promoter. Cells were also transfected with an empty vector or constructs encoding procaspase-3, -6, -8, or -10 as controls. The cells were stained with X-gal 30 h after transfection and examined for morphological signs of apoptosis. The percentage of round blue apoptotic cells (mean ±SD) were represented as a function of total blue cells under each condition (n≧3). SD was less than 5%. As depicted in FIG. 4, overexpression of procaspase-3 as well as procaspase-14, but not procaspase-8 or -10, was unable to induce any significant amount of apoptosis. This suggests that procaspase-14, like other executioner procaspases with small prodomains, can not undergo self activation to induce apoptosis.

Example 4

Expression of Procaspase-14

Figure 5A:
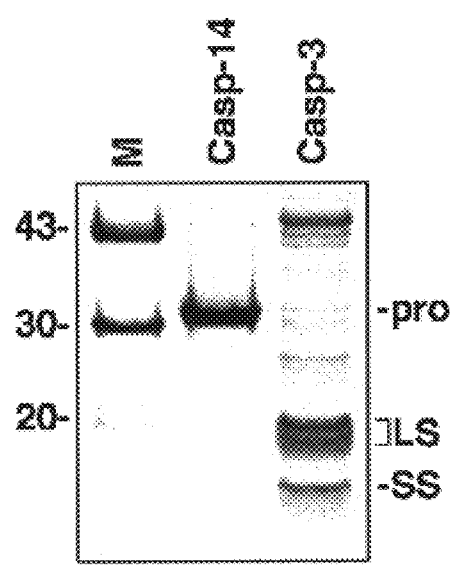
FIGS. 5A–C are scanned images of autoradiograms representing SDS-PAGE analysis of the expression and processing of procaspase-14.

Overexpression of procaspase-14 and procaspase-3 in bacteria. Procaspase-14 and procaspase-3 were expressed in *Escheiichia coli* purified on Talon $Ni^{+2}$-affinity resin (Clontech, and then analyzed by SDS-PAGE and Coomassie staining. As depicted in FIG. 5A, Lane M, molecular mass markers (kDa); lane casp-14, Talon-affinity purified caspase-14, lane casp-3, Talon-affinity purified caspase-3.

Example 5

Processing of Procaspase-14

Figure 5B:
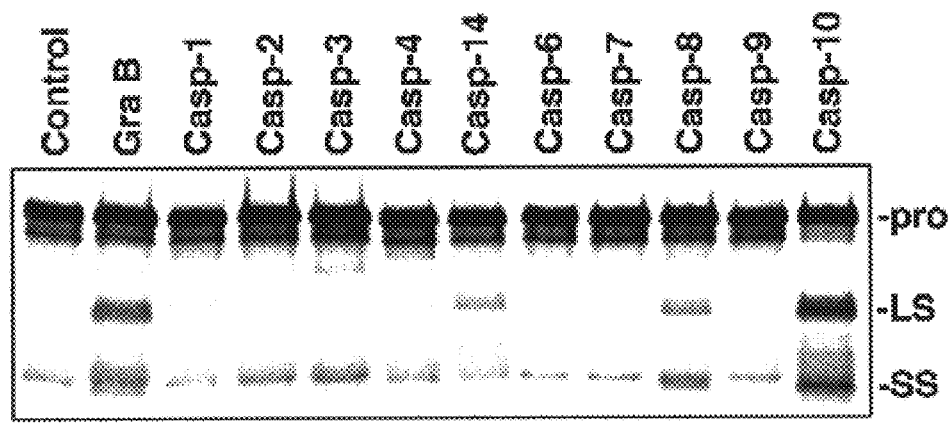

Upon expression in bacteria, all procaspases are known to autoprocess to various degrees to generate the mature caspase which is composed of the large and small subunits. The observed auto-activation in bacterial overexpression systems is probably mediated by overexpression-induced oligomerization. Oligomerization has been shown to induce autoactivation/processing of procaspases. Interestingly, when procaspase-14 was overexpressed in bacteria there was no significant processing of its proenzyme compared to procaspase-3 which was completely processes (FIG. 5A). This suggests that procaspase-14 does not normally process itself and it may require an upstream protease to process it. To test this possibility, procaspase-14 was incubated with Granzyme B which is known to process several caspase proenzymes. In addition procaspase-14 was incubated with different purified recombinant caspases. As shown in FIG. 5B. a significant amount of processing was observed when procaspase-14 was incubated with Granzyme B., caspase-10 and caspase-8, but not with other caspases. Some processing was also observed with recombinant caspase-14 itself, indicating that the purified caspase-14 material contains small amount of active capase-14. These observations suggest that procaspase-14 may participate in the Granzyme B. caspase-8 and caspase-10 protease cascades.

Processing of mouse procaspase-14 by Granzyme B and purified recombinant caspases was carried out under the following conditions: $^{35}S$ labeled procaspase-14 was incubated with purified Granzyme B (14 ng/μl) or the indicated purified recombinant caspases (20 ng/μl) in ICE buffer (25 mM Hepes, 1 mM EDTA, 5 mM DTT, 0.1% CHAPS, pH 7.5) at 37° C. for 1 h. The reactions were stopped by addition of an SDS-sample buffer and then the products were analyzed by SDS-PAGE and autoradiography.

Figure 5C:
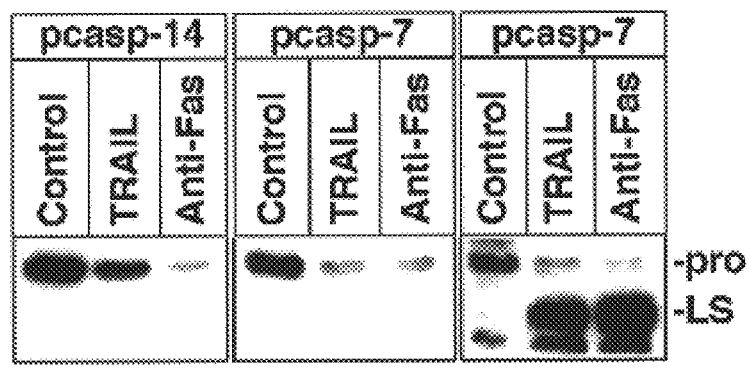

Since caspase-8 and -10 are initiator caspases that are activated by oligomerization of the death receptors (i.e., Fas, TRAIL-R) by their ligands or agonist antibodies, the possibility that procaspase-14 is processed in vivo after induction of apoptosis by anti-Fas antibody or the cytotoxic ligand TRAIL was tested. A mammalian expression construct encoding N-terminal T7-tagged procaspase-14 was transfected into MCF-7-FAS cells. The cells were treated 36 h after transfection with agonist anti-Fas antibody or TRAIL for 3 h. Cells were harvested and lysed by addition of SDS-sample buffer. The cellular proteins were analyzed by SDS-PAGE and then immunoblotted with an anti-T7 HRP-conjugated monoclonal antibody (FIG. 5C, left panel) to detect procaspase-14. The same samples were also immunoblotted with a polyclonal antibody (anti-Mch3α) that preferentially detects the proform of caspase-7 (FIG. 5C, middle panel), or a mixture of the anti-Mch3α antibody and CM-1 antibody that preferentially detects the processes fragments of caspase-7 (FIG. 5C, right panel) to detect the endogenous caspase-7. Pro indicates the proenzyme, LS indicates the large subunit and SS indicates the small subunit. As shown in FIG. 5C, Anti-Fas and TRAIL were able to induce processing of procaspase-14 and procaspase-7 as evident from the decreased intensity of their proenzyme bands. The cleavage products of procaspase-14 were not clearly detectable probably due to loss of the epitope tag after processing of the small prodomain of procaspase-14 at Asp7 or AspI 7. On the other hand, the cleavage products of procaspase-7 were clearly detectable using an antibody that detects the processes large subunit of procaspase-7 (FIG. 5C, right panel). These observations indicate that caspase-14, like caspase-7, is likely involved in the death receptor pathways.

Example 6

Cytochrome C Dependent Processing of Procaspase-14

To determine if caspase-14 was activated by a way of Apaf-1 and caspase-9, cytochrome c dependent activation was tested. $^{35}S$ labeled procaspase-3 (FIG. 6, lanes 1 & 2), procaspase-7 (FIG. 6, lanes 3 & 4), or procaspase-14 (FIG. 6, lanes 5 & 6) were incubated with S100 extracts from human embryonic kidney 293 cells in the absence (−) or presence (+) of cytochrome c (50 ng/μl) and dATP (1 mM) in buffer A (20 mM Hepes, 10 mM KCl, 1.5 mM $MgCl_2$, 1 mM FDTA, 1 mM EGTA, 1 mM DTT. 0.1 mM PMSF, pH 7.5) at 30° C. for 1 h. The reaction products were then analyzed by SDS-PAGE and autoradiography.

Figure 6:
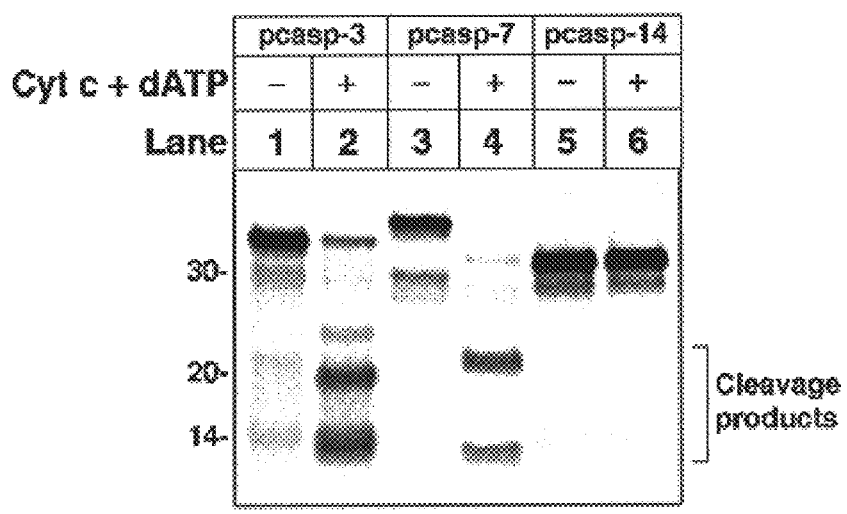
FIG. 6 is a scanned image of an autoradiogram representing SDS-PAGE analysis of the processing of procaspase-14 in S-100 extracts.

As indicated by FIG. 6, unlike caspase-3 or -7, no cleavage/activation of $^{35}S$ labeled procaspase-14 was observed in S-100 extracts activated by cytochrome c and dATP. This indicates that cytochrome c-activated caspase-3, −6, −7, and -9 in the S-100 cellular extract likely cannot process procaspase-14.

SEQUENCE LISTING

<160> NUMBER OF SEQ ID NOS: 78

<210> SEQ ID NO 1
<211> LENGTH: 850
<212> TYPE: DNA
<213> ORGANISM: Mus musculus
<220> FEATURE:
<221> NAME/KEY: modified_base
<222> LOCATION: (537)
<223> OTHER INFORMATION: Where n is Adenine, Cytosine, Guanine or Thymine

<400> SEQUENCE: 1

```
cacgcgtccg cccacgcgtc cggtgagaca gaggcaaaac aaaggtgctg aaagccagac    60
atggagtcag agatgagtga tcctcagcca ttgcaggagg aaagatatga tatgtcaggt   120
gcccgcctgg ccctgacgct gtgtgtcacc aaagcccggg agggttccga ggtagacatg   180
gaggccctgg aacgcatgtt ccgttacctg aaatttgaaa gcaccatgaa gagggatccc   240
accgcccagc aatttctgga agagttggat gaatttcagc agaccataga taattgggaa   300
gagcctgtca gctgtgcctt tgtggtactc atggcacatg gtgaggaagg cctcctcaag   360
ggagaagatg agaagatggt cagactagaa gaccttttg aagtcttgaa caacaagaac    420
tgcaaggccc tgagaggcaa gccaaaggtg tacatcatcc aggcttgtag aggagagcac   480
agagaccccg gtgaggaact acgtggaaat gaggaactag gtggagatga ggaactnggt   540
ggagatgagg ttgctgtgct caagaacaac ccccaaagta tcccaaccta tacggatacc   600
ctccacatct actccacggt agaggggtac ctctcctata gacatgacga gaaaggctct   660
ggcttcatcc agaccctgac ggatgtgttc attcataaaa aaggatccat cttagaactg   720
acagaagaga tcacccgact tatggcaaac acggaggtga tgcaggaagg aaaaccaagg   780
aaagtgaacc ctgaagtcca agcaccctc cggaagaagc tctatttgca ataaaagaga    840
gggcagggat                                                         850
```

<210> SEQ ID NO 2
<211> LENGTH: 260
<212> TYPE: PRT
<213> ORGANISM: Mus musculus

<400> SEQUENCE: 2

```
Lys Pro Asp Met Glu Ser Glu Met Ser Asp Pro Gln Pro Leu Gln Glu
 -3      -1   1           5                  10

Glu Arg Tyr Asp Met Ser Gly Ala Arg Leu Ala Leu Thr Leu Cys Val
         15              20                  25

Thr Lys Ala Arg Glu Gly Ser Glu Val Asp Met Glu Ala Leu Glu Arg
 30              35                  40                  45

Met Phe Arg Tyr Leu Lys Phe Glu Ser Thr Met Lys Arg Asp Pro Thr
                     50                  55                  60

Ala Gln Gln Phe Leu Glu Glu Leu Asp Glu Phe Gln Gln Thr Ile Asp
                 65                  70                  75

Asn Trp Glu Glu Pro Val Ser Cys Ala Phe Val Val Leu Met Ala His
         80                  85                  90

Gly Glu Glu Gly Leu Leu Lys Gly Glu Asp Glu Lys Met Val Arg Leu
     95                  100                 105

Glu Asp Leu Phe Glu Val Leu Asn Asn Lys Asn Cys Lys Ala Leu Arg
110                 115                 120                 125
```

```
Gly Lys Pro Lys Val Tyr Ile Ile Gln Ala Cys Arg Gly His Arg
            130                 135                 140

Asp Pro Gly Glu Glu Leu Arg Gly Asn Glu Glu Leu Gly Gly Asp Glu
            145                 150                 155

Glu Leu Gly Gly Asp Glu Val Ala Val Leu Lys Asn Asn Pro Gln Ser
            160                 165                 170

Ile Pro Thr Tyr Thr Asp Thr Leu His Ile Tyr Ser Thr Val Glu Gly
    175                 180                 185

Tyr Leu Ser Tyr Arg His Asp Glu Lys Gly Ser Gly Phe Ile Gln Thr
190                 195                 200                 205

Leu Thr Asp Val Phe Ile His Lys Lys Gly Ser Ile Leu Glu Leu Thr
                210                 215                 220

Glu Glu Ile Thr Arg Leu Met Ala Asn Thr Glu Val Met Gln Glu Gly
            225                 230                 235

Lys Pro Arg Lys Val Asn Pro Glu Val Gln Ser Thr Leu Arg Lys Lys
            240                 245                 250

Leu Tyr Leu Gln
    255

<210> SEQ ID NO 3
<211> LENGTH: 5
<212> TYPE: PRT
<213> ORGANISM: Mus musculus

<400> SEQUENCE: 3

Gln Ala Cys Arg Gly
1               5

<210> SEQ ID NO 4
<211> LENGTH: 777
<212> TYPE: DNA
<213> ORGANISM: Homo sapien
<220> FEATURE:
<221> NAME/KEY: CDS
<222> LOCATION: (49)...(774)

<400> SEQUENCE: 4
aggatcagac aagggtgctg agagccggga ctcacaacca aaggagaa atg agc aat     57
                                                    Met Ser Asn
                                                        1 ccg cgg tct ttg gaa gag gag aaa tat gat atg tca ggt gcc gcg ctg    105
Pro Arg Ser Leu Glu Glu Glu Lys Tyr Asp Met Ser Gly Ala Ala Leu
  5                  10                  15 gcc cta ata ctg tgt gtc acc aaa gcc cgg gaa ggt tcc gaa gaa gac    153
Ala Leu Ile Leu Cys Val Thr Lys Ala Arg Glu Gly Ser Glu Glu Asp
 20                  25                  30                  35 ctg gat gct ctg gaa cac atg ttt cgg cag ctg aga ttc gaa agc acc    201
Leu Asp Ala Leu Glu His Met Phe Arg Gln Leu Arg Phe Glu Ser Thr
                 40                  45                  50 atg aaa aga gac ccc act gcc gag caa ttc cag gaa gag ctg gaa aaa    249
Met Lys Arg Asp Pro Thr Ala Glu Gln Phe Gln Glu Glu Leu Glu Lys
             55                  60                  65 ttc cag cag gcc atc gat tcc cgg gaa gat ccc gtc agt tgt gcc ttc    297
Phe Gln Gln Ala Ile Asp Ser Arg Glu Asp Pro Val Ser Cys Ala Phe
         70                  75                  80 gtg gta ctc atg gct cac ggg agg gaa ggc ttc ctc aag gga gaa gat    345
Val Val Leu Met Ala His Gly Arg Glu Gly Phe Leu Lys Gly Glu Asp
 85                  90                  95 ggg gag atg gtc aag ctg gag aat ctc ttc gag gcc ctg aac aac aag    393
Gly Glu Met Val Lys Leu Glu Asn Leu Phe Glu Ala Leu Asn Asn Lys
```

-continued

```
       100                 105                 110                 115
aac tgc cag gcc ctg cga gct aag ccc aag gtg tac atc ata cag gcc              441
Asn Cys Gln Ala Leu Arg Ala Lys Pro Lys Val Tyr Ile Ile Gln Ala
            120                 125                 130 tgt cga gga gaa caa agg gac ccc ggt gaa aca gta ggt gga gat gag              489
Cys Arg Gly Glu Gln Arg Asp Pro Gly Glu Thr Val Gly Gly Asp Glu
            135                 140                 145 att gtg atg gtc atc aaa gac agc cca caa acc atc cca aca tac aca              537
Ile Val Met Val Ile Lys Asp Ser Pro Gln Thr Ile Pro Thr Tyr Thr
            150                 155                 160 gat gcc ttg cac gtt tat tcc acg gta gag gga tac atc gcc tac cga              585
Asp Ala Leu His Val Tyr Ser Thr Val Glu Gly Tyr Ile Ala Tyr Arg
            165                 170                 175 cat gat cag aaa ggc tca tgc ttt atc cag acc ctg gtg gat gtg ttc              633
His Asp Gln Lys Gly Ser Cys Phe Ile Gln Thr Leu Val Asp Val Phe
180                 185                 190                 195 acg aag agg aaa gga cat atc ttg gaa ctt ctg aca gag gtg acc cgg              681
Thr Lys Arg Lys Gly His Ile Leu Glu Leu Leu Thr Glu Val Thr Arg
            200                 205                 210 cgg atg gca gaa gca gag ctg gtt caa gaa gga aaa gca agg aaa acg              729
Arg Met Ala Glu Ala Glu Leu Val Gln Glu Gly Lys Ala Arg Lys Thr
            215                 220                 225 aac cct gaa atc caa agc acc ctc cgg aaa cgg ctg tat ctg cag                  774
Asn Pro Glu Ile Gln Ser Thr Leu Arg Lys Arg Leu Tyr Leu Gln
            230                 235                 240 tag                                                                          777
```

<210> SEQ ID NO 5
<211> LENGTH: 242
<212> TYPE: PRT
<213> ORGANISM: Homo sapien

<400> SEQUENCE: 5

```
Met Ser Asn Pro Arg Ser Leu Glu Glu Glu Lys Tyr Asp Met Ser Gly
 1               5                  10                  15

Ala Ala Leu Ala Leu Ile Leu Cys Val Thr Lys Ala Arg Glu Gly Ser
                20                  25                  30

Glu Glu Asp Leu Asp Ala Leu Glu His Met Phe Arg Gln Leu Arg Phe
            35                  40                  45

Glu Ser Thr Met Lys Arg Asp Pro Thr Ala Glu Gln Phe Gln Glu Glu
        50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
            100                 105                 110

Asn Asn Lys Asn Cys Gln Ala Leu Arg Ala Lys Pro Lys Val Tyr Ile
        115                 120                 125

Ile Gln Ala Cys Arg Gly Glu Gln Arg Asp Pro Gly Glu Thr Val Gly
    130                 135                 140

Gly Asp Glu Ile Val Met Val Ile Lys Asp Ser Pro Gln Thr Ile Pro
145                 150                 155                 160

Thr Tyr Thr Asp Ala Leu His Val Tyr Ser Thr Val Glu Gly Tyr Ile
                165                 170                 175

Ala Tyr Arg His Asp Gln Lys Gly Ser Cys Phe Ile Gln Thr Leu Val
            180                 185                 190
```

```
Asp Val Phe Thr Lys Arg Lys Gly His Ile Leu Glu Leu Leu Thr Glu
            195                 200                 205

Val Thr Arg Arg Met Ala Glu Ala Glu Leu Val Gln Glu Gly Lys Ala
        210                 215                 220

Arg Lys Thr Asn Pro Glu Ile Gln Ser Thr Leu Arg Lys Arg Leu Tyr
225                 230                 235                 240

Leu Gln

<210> SEQ ID NO 6
<211> LENGTH: 850
<212> TYPE: DNA
<213> ORGANISM: Homo sapien
<220> FEATURE:
<221> NAME/KEY: CDS
<222> LOCATION: (48)...(737)

<400> SEQUENCE: 6
aggatcagac aagggtgctg agagccggac tcacaaccaa aggagaa atg agc aat        56
                                                    Met Ser Asn
                                                     1 ccg cgg tct ttg gaa gag gag aaa tat gat atg tca ggt gcc cgc ctg       104
Pro Arg Ser Leu Glu Glu Glu Lys Tyr Asp Met Ser Gly Ala Arg Leu
      5                  10                  15 gcc cta ata ctg tgt gtc acc aaa gcc cgg gaa ggt tcc gaa gaa gac       152
Ala Leu Ile Leu Cys Val Thr Lys Ala Arg Glu Gly Ser Glu Glu Asp
 20                  25                  30                  35 ctg gat gct ctg gaa cac atg ttt cgg cag ctg aga ttc gaa agc acc       200
Leu Asp Ala Leu Glu His Met Phe Arg Gln Leu Arg Phe Glu Ser Thr
                 40                  45                  50 atg aaa aga gac ccc act gcc gag caa ttc cag gaa gag ctg gaa aaa       248
Met Lys Arg Asp Pro Thr Ala Glu Gln Phe Gln Glu Glu Leu Glu Lys
             55                  60                  65 ttc cag cag gcc atc gat tcc cgg gaa gat ccc gtc agt tgt gcc ttc       296
Phe Gln Gln Ala Ile Asp Ser Arg Glu Asp Pro Val Ser Cys Ala Phe
         70                  75                  80 gtg gta ctc atg gct cac ggg agg gaa ggc ttc ctc aag gga gaa gat       344
Val Val Leu Met Ala His Gly Arg Glu Gly Phe Leu Lys Gly Glu Asp
     85                  90                  95 ggg gag atg gtc aag ctg gag aat ctc ttc gag gcc ctg aac aac aag       392
Gly Glu Met Val Lys Leu Glu Asn Leu Phe Glu Ala Leu Asn Asn Lys
100                 105                 110                 115 aac tgc cag gcc ctg cga gct aag ccc aag gtg tac atc ata cag gcc       440
Asn Cys Gln Ala Leu Arg Ala Lys Pro Lys Val Tyr Ile Ile Gln Ala
                120                 125                 130 tgt cga gga gaa caa agg gac ccc ggt gaa aca gta ggt gga gat gag       488
Cys Arg Gly Glu Gln Arg Asp Pro Gly Glu Thr Val Gly Gly Asp Glu
            135                 140                 145 att gtg atg gtc atc aaa gac agc cca caa acc atc cca aca tac aca       536
Ile Val Met Val Ile Lys Asp Ser Pro Gln Thr Ile Pro Thr Tyr Thr
        150                 155                 160 gat gcc ttg cac gtt tat tcc acg gta gag gga ccc acg ccc ttc cag       584
Asp Ala Leu His Val Tyr Ser Thr Val Glu Gly Pro Thr Pro Phe Gln
    165                 170                 175 gat ccc ctc tac cta ccc tct gaa gct ccc ccg aac cca cct ctc tgg       632
Asp Pro Leu Tyr Leu Pro Ser Glu Ala Pro Pro Asn Pro Pro Leu Trp
180                 185                 190                 195 aat tcc cag gat aca tcg cct acc gac atg atc aga aag gct cat gct       680
Asn Ser Gln Asp Thr Ser Pro Thr Asp Met Ile Arg Lys Ala His Ala
                200                 205                 210
```

-continued

```
tta tcc aga ccc tgg tgg atg tgt tca cga aga gga aag gac ata tct    728
Leu Ser Arg Pro Trp Trp Met Cys Ser Arg Arg Gly Lys Asp Ile Ser
        215                 220                 225 tgg aac ttc tgacagaggt gacccggcgg atggcagaag cagagctggt            777
Trp Asn Phe
        230 tcaagaagga aaagcaagga aaacgaaccc tgaaatccaa agcaccctcc ggaaacggct  837 gtatctgcag tag                                                     850

<210> SEQ ID NO 7
<211> LENGTH: 230
<212> TYPE: PRT
<213> ORGANISM: Homo sapien

<400> SEQUENCE: 7

Met Ser Asn Pro Arg Ser Leu Glu Glu Glu Lys Tyr Asp Met Ser Gly
 1               5                  10                  15

Ala Arg Leu Ala Leu Ile Leu Cys Val Thr Lys Ala Arg Glu Gly Ser
            20                  25                  30

Glu Glu Asp Leu Asp Ala Leu Glu His Met Phe Arg Gln Leu Arg Phe
        35                  40                  45

Glu Ser Thr Met Lys Arg Asp Pro Thr Ala Glu Gln Phe Gln Glu Glu
    50                  55                  60

Leu Glu Lys Phe Gln Gln Ala Ile Asp Ser Arg Glu Asp Pro Val Ser
65                  70                  75                  80

Cys Ala Phe Val Val Leu Met Ala His Gly Arg Glu Gly Phe Leu Lys
                85                  90                  95

Gly Glu Asp Gly Glu Met Val Lys Leu Glu Asn Leu Phe Glu Ala Leu
            100                 105                 110

Asn Asn Lys Asn Cys Gln Ala Leu Arg Ala Lys Pro Lys Val Tyr Ile
        115                 120                 125

Ile Gln Ala Cys Arg Gly Glu Gln Arg Asp Pro Gly Glu Thr Val Gly
    130                 135                 140

Gly Asp Glu Ile Val Met Val Ile Lys Asp Ser Pro Gln Thr Ile Pro
145                 150                 155                 160

Thr Tyr Thr Asp Ala Leu His Val Tyr Ser Thr Val Glu Gly Pro Thr
                165                 170                 175

Pro Phe Gln Asp Pro Leu Tyr Leu Pro Ser Glu Ala Pro Pro Asn Pro
            180                 185                 190

Pro Leu Trp Asn Ser Gln Asp Thr Ser Pro Thr Asp Met Ile Arg Lys
        195                 200                 205

Ala His Ala Leu Ser Arg Pro Trp Trp Met Cys Ser Arg Arg Gly Lys
    210                 215                 220

Asp Ile Ser Trp Asn Phe
225                 230

<210> SEQ ID NO 8
<211> LENGTH: 693
<212> TYPE: DNA
<213> ORGANISM: Homo sapien
<220> FEATURE:
<221> NAME/KEY: CDS
<222> LOCATION: (49)...(690)

<400> SEQUENCE: 8
aggatcagac aagggtgctg agagccggga ctcacaacca aaggagaa atg agc aat   57
                                                 Met Ser Asn
                                                  1
```

-continued

```
ccg cgg tct ttg gaa gag gag aaa tat gat atg tca ggt gcc cgc ctg    105
Pro Arg Ser Leu Glu Glu Glu Lys Tyr Asp Met Ser Gly Ala Arg Leu
    5                  10                  15 gcc cta ata ctg tgt gtc acc aaa gcc cgg gaa ggt tcc gaa gaa gaa    153
Ala Leu Ile Leu Cys Val Thr Lys Ala Arg Glu Gly Ser Glu Glu Glu
 20                  25                  30                  35 gag ctg gaa aaa ttc cag cag gcc atc gat tcc cgg gaa gat ccc gtc    201
Glu Leu Glu Lys Phe Gln Gln Ala Ile Asp Ser Arg Glu Asp Pro Val
                 40                  45                  50 agt tgt gcc ttc gtg gta ctc atg gct cac ggg agg gaa ggc ttc ctc    249
Ser Cys Ala Phe Val Val Leu Met Ala His Gly Arg Glu Gly Phe Leu
             55                  60                  65 aag gga gaa gat ggg gag atg gtc aag ctg gag aat ctc ttc gag gcc    297
Lys Gly Glu Asp Gly Glu Met Val Lys Leu Glu Asn Leu Phe Glu Ala
         70                  75                  80 ctg aac aac aag aac tgc cag gcc ctg cga gct aag ccc aag gtg tac    345
Leu Asn Asn Lys Asn Cys Gln Ala Leu Arg Ala Lys Pro Lys Val Tyr
     85                  90                  95 atc ata cag gcc tgt cga gga gaa caa agg gac ccc ggt gaa aca gta    393
Ile Ile Gln Ala Cys Arg Gly Glu Gln Arg Asp Pro Gly Glu Thr Val
100                 105                 110                 115 ggt gga gat gag att gtg atg gtc atc aaa gac agc cca caa acc atc    441
Gly Gly Asp Glu Ile Val Met Val Ile Lys Asp Ser Pro Gln Thr Ile
                120                 125                 130 cca aca tac aca gat gcc ttg cac gtt tat tcc acg gta gag gga tac    489
Pro Thr Tyr Thr Asp Ala Leu His Val Tyr Ser Thr Val Glu Gly Tyr
            135                 140                 145 atc gcc tac cga cat gat cag aaa ggc tca tgc ttt atc cag acc ctg    537
Ile Ala Tyr Arg His Asp Gln Lys Gly Ser Cys Phe Ile Gln Thr Leu
        150                 155                 160 gtg gat gtg ttc acg aag agg aaa gga cat atc ttg gaa ctt ctg aca    585
Val Asp Val Phe Thr Lys Arg Lys Gly His Ile Leu Glu Leu Leu Thr
    165                 170                 175 gag gtg acc cgg cgg atg gca gaa gca gag ctg gtt caa gaa gga aaa    633
Glu Val Thr Arg Arg Met Ala Glu Ala Glu Leu Val Gln Glu Gly Lys
180                 185                 190                 195 gca agg aaa acg aac cct gaa atc caa agc acc ctc cgg aaa cgg ctg    681
Ala Arg Lys Thr Asn Pro Glu Ile Gln Ser Thr Leu Arg Lys Arg Leu
                200                 205                 210 tat ctg cag tag                                                    693
Tyr Leu Gln
```

<210> SEQ ID NO 9
<211> LENGTH: 214
<212> TYPE: PRT
<213> ORGANISM: Homo sapien

<400> SEQUENCE: 9

```
Met Ser Asn Pro Arg Ser Leu Glu Glu Glu Lys Tyr Asp Met Ser Gly
 1               5                  10                  15

Ala Arg Leu Ala Leu Ile Leu Cys Val Thr Lys Ala Arg Glu Gly Ser
                20                  25                  30

Glu Glu Glu Glu Leu Glu Lys Phe Gln Gln Ala Ile Asp Ser Arg Glu
         35                  40                  45

Asp Pro Val Ser Cys Ala Phe Val Val Leu Met Ala His Gly Arg Glu
     50                  55                  60

Gly Phe Leu Lys Gly Glu Asp Gly Glu Met Val Lys Leu Glu Asn Leu
 65                  70                  75                  80
```

```
Phe Glu Ala Leu Asn Asn Lys Asn Cys Gln Ala Leu Arg Ala Lys Pro
                85                  90                  95

Lys Val Tyr Ile Ile Gln Ala Cys Arg Gly Glu Gln Arg Asp Pro Gly
            100                 105                 110

Glu Thr Val Gly Gly Asp Glu Ile Val Met Val Ile Lys Asp Ser Pro
        115                 120                 125

Gln Thr Ile Pro Thr Tyr Thr Asp Ala Leu His Val Tyr Ser Thr Val
    130                 135                 140

Glu Gly Tyr Ile Ala Tyr Arg His Asp Gln Lys Gly Ser Cys Phe Ile
145                 150                 155                 160

Gln Thr Leu Val Asp Val Phe Thr Lys Arg Lys Gly His Ile Leu Glu
                165                 170                 175

Leu Leu Thr Glu Val Thr Arg Arg Met Ala Glu Ala Glu Leu Val Gln
            180                 185                 190

Glu Gly Lys Ala Arg Lys Thr Asn Pro Glu Ile Gln Ser Thr Leu Arg
        195                 200                 205

Lys Arg Leu Tyr Leu Gln
    210

<210> SEQ ID NO 10
<211> LENGTH: 22
<212> TYPE: PRT
<213> ORGANISM: Mus musculus

<400> SEQUENCE: 10

Met Ala Glu Asn Lys His Pro Asp Lys Pro Leu Lys Val Leu Glu Gln
1               5                   10                  15

Leu Gly Lys Glu Val Leu
            20

<210> SEQ ID NO 11
<211> LENGTH: 36
<212> TYPE: PRT
<213> ORGANISM: Mus musculus

<400> SEQUENCE: 11

Thr Glu Tyr Leu Glu Lys Leu Val Gln Ser Asn Val Leu Lys Leu Lys
1               5                   10                  15

Glu Glu Asp Lys Gln Lys Phe Asn Asn Ala Glu Arg Ser Asp Lys Arg
            20                  25                  30

Trp Val Phe Val
            35

<210> SEQ ID NO 12
<211> LENGTH: 70
<212> TYPE: PRT
<213> ORGANISM: Mus musculus

<400> SEQUENCE: 12

Asp Ala Met Lys Lys His Ser Lys Val Gly Glu Met Leu Leu Gln
1               5                   10                  15

Thr Phe Phe Ser Val Asp Pro Gly Ser His Gly Glu Ala Asn Leu
            20                  25                  30

Glu Met Glu Glu Pro Glu Glu Ser Leu Asn Thr Leu Lys Leu Cys Ser
        35                  40                  45

Pro Glu Glu Phe Thr Arg Leu Cys Arg Glu Lys Thr Gln Glu Ile Tyr
    50                  55                  60

Pro Ile Lys Glu Ala Asn
```

<210> SEQ ID NO 13
<211> LENGTH: 62
<212> TYPE: PRT
<213> ORGANISM: Mus musculus

<400> SEQUENCE: 13

```
Gly Arg Thr Arg Lys Ala Leu Ile Ile Cys Asn Thr Glu Phe Lys His
 1               5                  10                  15
Leu Ser Leu Arg Tyr Gly Ala Asn Phe Asp Ile Ile Gly Met Lys Gly
            20                  25                  30
Leu Leu Glu Asp Leu Gly Tyr Asp Val Val Lys Glu Glu Leu Thr
        35                  40                  45
Ala Glu Gly Met Glu Ser Glu Met Asp Lys Phe Ala Ala Leu
    50                  55                  60
```

<210> SEQ ID NO 14
<211> LENGTH: 94
<212> TYPE: PRT
<213> ORGANISM: Mus musculus

<400> SEQUENCE: 14

```
Ser Glu His Gln Thr Ser Asp Ser Thr Phe Leu Val Leu Met Ser His
 1               5                  10                  15
Gly Thr Leu His Gly Ile Cys Gly Thr Met His Ser Glu Lys Thr Pro
            20                  25                  30
Asp Val Leu Gln Tyr Asp Thr Ile Tyr Gln Ile Phe Asn Asn Cys His
        35                  40                  45
Cys Pro Gly Leu Arg Asp Lys Pro Lys Val Ile Ile Val Gln Ala Cys
    50                  55                  60
Arg Gly Gly Asn Ser Gly Glu Met Trp Ile Arg Glu Ser Ser Lys Pro
65                  70                  75                  80
Gln Leu Cys Arg Gly Val Asp Leu Pro Arg Asn Met Glu Ala
                85                  90
```

<210> SEQ ID NO 15
<211> LENGTH: 89
<212> TYPE: PRT
<213> ORGANISM: Mus musculus

<400> SEQUENCE: 15

```
Asp Ala Val Lys Leu Ser His Val Glu Lys Asp Phe Ile Ala Phe Tyr
 1               5                  10                  15
Ser Thr Thr Pro His His Leu Ser Tyr Arg Asp Lys Thr Gly Gly Ser
            20                  25                  30
Tyr Phe Ile Thr Arg Leu Ile Ser Cys Phe Arg Lys His Ala Cys Ser
        35                  40                  45
Cys His Leu Phe Asp Ile Phe Leu Lys Val Gln Gln Ser Phe Glu Lys
    50                  55                  60
Ala Ser Ile His Ser Gln Met Pro Thr Ile Asp Arg Ala Thr Leu Thr
65                  70                  75                  80
Arg Tyr Phe Tyr Leu Phe Pro Gly Asn
                85
```

<210> SEQ ID NO 16
<211> LENGTH: 172
<212> TYPE: PRT
<213> ORGANISM: Mus musculus

<400> SEQUENCE: 16

```
Met Ala Ala Arg Arg Thr His Glu Arg Asp Pro Ile Tyr Lys Ile Lys
 1               5                  10                  15
Gly Leu Ala Lys Asp Met Leu Asp Gly Val Phe Asp Leu Val Glu
             20                  25                  30
Lys Asn Val Leu Asn Gly Asp Glu Leu Leu Lys Ile Gly Glu Ser Ala
             35                  40                  45
Ser Phe Ile Leu Asn Lys Ala Glu Asn Leu Val Glu Asn Phe Leu Glu
     50                  55                  60
Lys Thr Asp Met Ala Gly Lys Ile Phe Ala Gly His Ile Ala Asn Ser
 65                  70                  75                  80
Gln Glu Gln Leu Ser Leu Gln Phe Ser Asn Asp Glu Asp Asp Gly Pro
                 85                  90                  95
Gln Lys Ile Cys Thr Pro Ser Ser Pro Ser Glu Ser Lys Arg Lys Val
                100                 105                 110
Glu Asp Asp Glu Met Glu Val Asn Ala Gly Leu Ala His Glu Ser His
            115                 120                 125
Leu Met Leu Thr Ala Pro His Gly Leu Gln Ser Ser Glu Val Gln Asp
130                 135                 140
Thr Leu Lys Leu Cys Pro Arg Asp Gln Phe Cys Lys Ile Lys Thr Glu
145                 150                 155                 160
Arg Ala Lys Glu Ile Tyr Pro Val Met Glu Lys Glu
                165                 170
```

<210> SEQ ID NO 17
<211> LENGTH: 62
<212> TYPE: PRT
<213> ORGANISM: Mus musculus

<400> SEQUENCE: 17

```
Gly Arg Thr Arg Leu Ala Leu Ile Ile Cys Asn Lys Lys Phe Asp Tyr
 1               5                  10                  15
Leu Phe Asp Arg Asp Asn Ala Asp Thr Asp Ile Leu Asn Met Gln Glu
             20                  25                  30
Leu Leu Glu Asn Leu Gly Tyr Ser Val Val Leu Lys Glu Asn Leu Thr
         35                  40                  45
Ala Gln Glu Met Glu Thr Glu Leu Met Gln Phe Ala Gly Arg
     50                  55                  60
```

<210> SEQ ID NO 18
<211> LENGTH: 74
<212> TYPE: PRT
<213> ORGANISM: Mus musculus

<400> SEQUENCE: 18

```
Pro Glu His Gln Ser Ser Asp Ser Thr Phe Leu Val Phe Met Ser His
 1               5                  10                  15
Gly Ile Leu Glu Gly Ile Cys Gly Val Lys His Arg Asn Lys Lys Pro
             20                  25                  30
Asp Val Leu His Asp Asp Thr Ile Phe Lys Ile Phe Asn Asn Ser Asn
         35                  40                  45
Cys Arg Ser Leu Arg Asn Lys Pro Lys Ile Leu Ile Met Gln Ala Cys
     50                  55                  60
Arg Gly Arg Tyr Asn Gly Thr Ile Trp Val
 65                  70
```

```
<210> SEQ ID NO 19
<211> LENGTH: 21
<212> TYPE: PRT
<213> ORGANISM: Mus musculus

<400> SEQUENCE: 19

Ser Thr Asn Lys Gly Ile Ala Thr Ala Asp Thr Asp Glu Arg Val
 1               5                  10                  15

Leu Ser Cys Lys Trp
            20

<210> SEQ ID NO 20
<211> LENGTH: 90
<212> TYPE: PRT
<213> ORGANISM: Mus musculus

<400> SEQUENCE: 20

Asn Asn Ser Ile Thr Lys Ala His Val Glu Thr Asp Phe Ile Ala Phe
 1               5                  10                  15

Lys Ser Ser Thr Pro His Asn Ile Ser Trp Arg Val Gly Lys Thr Gly
                20                  25                  30

Ser Leu Phe Ile Ser Lys Leu Ile Asp Cys Phe Lys Lys Tyr Cys Trp
            35                  40                  45

Cys Tyr His Leu Glu Glu Ile Phe Arg Lys Val Gln His Ser Phe Glu
    50                  55                  60

Val Pro Gly Glu Leu Thr Gln Met Pro Thr Ile Glu Arg Val Ser Met
65                  70                  75                  80

Thr Arg Tyr Phe Tyr Leu Phe Pro Gly Asn
                85                  90

<210> SEQ ID NO 21
<211> LENGTH: 119
<212> TYPE: PRT
<213> ORGANISM: Mus musculus

<400> SEQUENCE: 21

Met Ala Asp Lys Ile Leu Arg Ala Lys Arg Lys Gln Phe Ile Asn Ser
 1               5                  10                  15

Val Ser Ile Gly Thr Ile Asn Gly Leu Leu Asp Glu Leu Leu Glu Lys
                20                  25                  30

Arg Val Leu Asn Gln Glu Glu Met Asp Lys Ile Lys Leu Ala Asn Ile
            35                  40                  45

Thr Ala Met Asp Lys Ala Arg Asp Leu Cys Asp His Val Ser Lys Lys
        50                  55                  60

Gly Pro Gln Ala Ser Gln Ile Phe Ile Thr Tyr Ile Cys Asn Glu Asp
65                  70                  75                  80

Cys Tyr Leu Ala Gly Ile Leu Glu Leu Gln Ser Ala Pro Ser Ala Glu
                85                  90                  95

Thr Phe Val Ala Thr Glu Asp Ser Lys Gly Gly His Pro Ser Ser Ser
                100                 105                 110

Glu Thr Lys Glu Glu Gln Asn
        115

<210> SEQ ID NO 22
<211> LENGTH: 11
<212> TYPE: PRT
<213> ORGANISM: Mus musculus

<400> SEQUENCE: 22
```

Lys Glu Asp Gly Thr Phe Pro Gly Leu Thr Gly
 1               5                  10

<210> SEQ ID NO 23
<211> LENGTH: 28
<212> TYPE: PRT
<213> ORGANISM: Mus musculus

<400> SEQUENCE: 23

Thr Leu Lys Phe Cys Pro Leu Glu Lys Ala Gln Lys Leu Trp Lys Glu
 1               5                  10                  15

Asn Pro Ser Glu Ile Tyr Pro Ile Met Asn Thr Thr
            20                  25

<210> SEQ ID NO 24
<211> LENGTH: 62
<212> TYPE: PRT
<213> ORGANISM: Mus musculus

<400> SEQUENCE: 24

Thr Arg Thr Arg Leu Ala Leu Ile Ile Cys Asn Thr Glu Phe Gln His
 1               5                  10                  15

Leu Ser Pro Arg Val Gly Ala Gln Val Asp Leu Arg Glu Met Lys Leu
            20                  25                  30

Leu Leu Glu Asp Leu Gly Tyr Thr Val Lys Val Lys Glu Asn Leu Thr
        35                  40                  45

Ala Leu Glu Met Val Lys Glu Val Lys Glu Phe Ala Ala Cys
    50                  55                  60

<210> SEQ ID NO 25
<211> LENGTH: 77
<212> TYPE: PRT
<213> ORGANISM: Mus musculus

<400> SEQUENCE: 25

Pro Glu His Lys Thr Ser Asp Ser Thr Phe Leu Val Phe Met Ser His
 1               5                  10                  15

Gly Ile Gln Glu Gly Ile Cys Gly Thr Thr Tyr Ser Asn Glu Val Ser
            20                  25                  30

Asp Ile Leu Lys Val Asp Thr Ile Phe Gln Met Met Asn Thr Leu Lys
        35                  40                  45

Cys Pro Ser Leu Lys Asp Lys Pro Lys Val Ile Ile Gln Ala Cys
    50                  55                  60

Arg Gly Glu Lys Gln Gly Val Val Leu Leu Lys Asp Ser
 65                  70                  75

<210> SEQ ID NO 26
<211> LENGTH: 105
<212> TYPE: PRT
<213> ORGANISM: Mus musculus

<400> SEQUENCE: 26

Val Arg Asp Ser Glu Glu Asp Phe Leu Thr Asp Ala Ile Phe Glu Asp
 1               5                  10                  15

Asp Gly Ile Lys Lys Ala His Ile Glu Lys Asp Phe Ile Ala Phe Cys
            20                  25                  30

Ser Ser Thr Pro Asp Asn Val Ser Trp Arg His Pro Val Arg Gly Ser
        35                  40                  45

Leu Phe Ile Glu Ser Leu Ile Lys His Met Lys Glu Tyr Ala Trp Ser

```
                    50                  55                  60
Cys Asp Leu Glu Asp Ile Phe Arg Lys Val Arg Phe Ser Phe Glu Gln
 65                  70                  75                  80

Pro Glu Phe Arg Leu Gln Met Pro Thr Ala Asp Arg Val Thr Leu Thr
                 85                  90                  95

Lys Arg Phe Tyr Leu Phe Pro Gly His
                100                 105

<210> SEQ ID NO 27
<211> LENGTH: 58
<212> TYPE: PRT
<213> ORGANISM: Mus musculus

<400> SEQUENCE: 27

Met Glu Asn Asn Lys Thr Ser Val Asp Ser Lys Ser Ile Asn Asn Phe
  1               5                  10                  15

Glu Val Lys Thr Ile His Gly Ser Lys Ser Val Asp Ser Gly Ile Tyr
                 20                  25                  30

Leu Asp Ser Ser Tyr Lys Met Asp Tyr Pro Glu Met Gly Ile Cys Ile
             35                  40                  45

Ile Ile Asn Asn Lys Asn Phe His Lys Ser
         50                  55

<210> SEQ ID NO 28
<211> LENGTH: 47
<212> TYPE: PRT
<213> ORGANISM: Mus musculus

<400> SEQUENCE: 28

Thr Gly Met Ser Ser Arg Ser Gly Thr Asp Val Asp Ala Ala Asn Leu
  1               5                  10                  15

Arg Glu Thr Phe Met Gly Leu Lys Tyr Cys Val Arg Asn Lys Asn Asp
                 20                  25                  30

Leu Thr Arg Glu Asp Ile Leu Glu Leu Met Asp Ser Val Ser Lys
             35                  40                  45

<210> SEQ ID NO 29
<211> LENGTH: 28
<212> TYPE: PRT
<213> ORGANISM: Mus musculus

<400> SEQUENCE: 29

Glu Asp His Ser Lys Arg Ser Ser Phe Val Cys Val Ile Leu Ser His
  1               5                  10                  15

Gly Asp Glu Gly Val Ile Tyr Gly Thr Asn Gly Pro
                 20                  25

<210> SEQ ID NO 30
<211> LENGTH: 39
<212> TYPE: PRT
<213> ORGANISM: Mus musculus

<400> SEQUENCE: 30

Val Glu Leu Lys Lys Leu Thr Ser Phe Phe Arg Gly Asp Tyr Cys Arg
  1               5                  10                  15

Ser Leu Thr Gly Lys Pro Lys Leu Phe Ile Ile Gln Ala Cys Arg Gly
                 20                  25                  30

Thr Glu Leu Asp Cys Gly Ile
             35
```

```
<210> SEQ ID NO 31
<211> LENGTH: 4
<212> TYPE: PRT
<213> ORGANISM: Mus musculus

<400> SEQUENCE: 31

Glu Thr Asp Ser
 1

<210> SEQ ID NO 32
<211> LENGTH: 7
<212> TYPE: PRT
<213> ORGANISM: Mus musculus

<400> SEQUENCE: 32

Thr Asp Glu Glu Met Ala Cys
 1               5

<210> SEQ ID NO 33
<211> LENGTH: 42
<212> TYPE: PRT
<213> ORGANISM: Mus musculus

<400> SEQUENCE: 33

Gln Lys Ile Pro Val Glu Ala Asp Phe Leu Tyr Ala Tyr Ser Thr Ala
 1               5                  10                  15

Pro Gly Tyr Tyr Ser Trp Arg Asn Ser Lys Asp Gly Ser Trp Phe Ile
            20                  25                  30

Gln Ser Leu Cys Ser Met Leu Lys Leu Tyr
        35                  40

<210> SEQ ID NO 34
<211> LENGTH: 51
<212> TYPE: PRT
<213> ORGANISM: Mus musculus

<400> SEQUENCE: 34

Ala His Lys Leu Glu Phe Met His Ile Leu Thr Arg Val Asn Arg Lys
 1               5                  10                  15

Val Ala Thr Glu Phe Glu Ser Phe Ser Leu Asp Ser Thr Phe His Ala
            20                  25                  30

Lys Lys Gln Ile Pro Cys Ile Val Ser Met Leu Thr Lys Glu Leu Tyr
        35                  40                  45

Phe Tyr His
        50

<210> SEQ ID NO 35
<211> LENGTH: 81
<212> TYPE: PRT
<213> ORGANISM: Mus musculus

<400> SEQUENCE: 35

Met Thr Asp Asp Gln Asp Cys Ala Ala Glu Leu Glu Lys Val Asp Ser
 1               5                  10                  15

Ser Ser Glu Asp Gly Val Asp Ala Lys Pro Asp Arg Ser Ser Ile Ile
            20                  25                  30

Ser Ser Ile Leu Leu Lys Lys Arg Asn Ala Ser Ala Gly Pro Val
        35                  40                  45

Arg Thr Gly Arg Asp Arg Val Pro Thr Tyr Leu Tyr Arg Met Asp Phe
        50                  55                  60
```

```
Gln Lys Met Gly Lys Cys Ile Ile Ile Asn Asn Lys Asn Phe Asp Lys
 65                  70                  75                  80
Ala
```

<210> SEQ ID NO 36
<211> LENGTH: 47
<212> TYPE: PRT
<213> ORGANISM: Mus musculus

<400> SEQUENCE: 36

```
Thr Gly Met Asp Val Arg Asn Gly Thr Asp Lys Asp Ala Gly Ala Leu
  1               5                  10                  15

Phe Lys Cys Phe Gln Asn Leu Gly Phe Glu Val Thr Val His Asn Asp
                 20                  25                  30

Cys Ser Cys Ala Lys Met Gln Asp Leu Leu Arg Lys Ala Ser Glu
             35                  40                  45
```

<210> SEQ ID NO 37
<211> LENGTH: 28
<212> TYPE: PRT
<213> ORGANISM: Mus musculus

<400> SEQUENCE: 37

```
Glu Asp His Ser Asn Ser Ala Cys Phe Ala Cys Val Leu Leu Ser His
  1               5                  10                  15

Gly Glu Glu Asp Leu Ile Tyr Gly Lys Asp Gly Val
                 20                  25
```

<210> SEQ ID NO 38
<211> LENGTH: 39
<212> TYPE: PRT
<213> ORGANISM: Mus musculus

<400> SEQUENCE: 38

```
Thr Pro Ile Lys Asp Leu Thr Ala His Phe Arg Gly Asp Arg Cys Lys
  1               5                  10                  15

Thr Leu Leu Glu Lys Pro Lys Leu Phe Phe Ile Gln Ala Cys Arg Gly
                 20                  25                  30

Thr Glu Leu Asp Asp Gly Ile
             35
```

<210> SEQ ID NO 39
<211> LENGTH: 4
<212> TYPE: PRT
<213> ORGANISM: Mus musculus

<400> SEQUENCE: 39

```
Gln Ala Asp Ser
  1
```

<210> SEQ ID NO 40
<211> LENGTH: 52
<212> TYPE: PRT
<213> ORGANISM: Mus musculus

<400> SEQUENCE: 40

```
Pro Ile Asn Asp Ile Asp Ala Asn Pro Arg Asn Lys Ile Pro Val Glu
  1               5                  10                  15

Ala Asp Phe Leu Phe Ala Tyr Ser Thr Val Pro Gly Tyr Tyr Ser Trp
                 20                  25                  30

Arg Asn Pro Gly Lys Gly Ser Trp Phe Val Gln Ala Leu Cys Ser Ile
```

```
                     35                  40                  45

Leu Asn Glu His
     50

<210> SEQ ID NO 41
<211> LENGTH: 51
<212> TYPE: PRT
<213> ORGANISM: Mus musculus

<400> SEQUENCE: 41

Gly Lys Asp Leu Glu Ile Met Gln Ile Leu Thr Arg Val Asn Asp Arg
 1               5                  10                  15

Val Ala Arg His Phe Glu Ser Gln Ser Asp Asp Pro Arg Phe Asn Glu
                20                  25                  30

Lys Lys Gln Ile Pro Cys Met Val Ser Met Leu Thr Lys Glu Leu Tyr
             35                  40                  45

Phe Ser Arg
     50

<210> SEQ ID NO 42
<211> LENGTH: 41
<212> TYPE: PRT
<213> ORGANISM: Mus musculus

<400> SEQUENCE: 42

Met Thr Glu Thr Asp Gly Phe Tyr Lys Ser Arg Glu Val Phe Asp Pro
 1               5                  10                  15

Ala Glu Gln Tyr Lys Met Asp His Lys Arg Arg Gly Val Ala Leu Ile
                20                  25                  30

Phe Asn His Glu Arg Phe Phe Trp His
             35                  40

<210> SEQ ID NO 43
<211> LENGTH: 47
<212> TYPE: PRT
<213> ORGANISM: Mus musculus

<400> SEQUENCE: 43

Leu Thr Leu Pro Glu Arg Arg Gly Thr Asn Ala Asp Arg Asp Asn Leu
 1               5                  10                  15

Thr Arg Arg Phe Ser Asp Leu Gly Phe Glu Val Lys Cys Phe Asn Asp
                20                  25                  30

Leu Arg Ala Glu Glu Leu Leu Leu Lys Ile His Glu Val Ser Thr
             35                  40                  45

<210> SEQ ID NO 44
<211> LENGTH: 28
<212> TYPE: PRT
<213> ORGANISM: Mus musculus

<400> SEQUENCE: 44

Ser Ser His Ile Asp Ala Asp Cys Phe Ile Cys Val Phe Leu Ser His
 1               5                  10                  15

Gly Glu Gly Asn His Val Tyr Ala Tyr Asp Ala Lys
                20                  25

<210> SEQ ID NO 45
<211> LENGTH: 51
<212> TYPE: PRT
<213> ORGANISM: Mus musculus
```

-continued

```
<400> SEQUENCE: 45

Ile Glu Ile Gln Thr Leu Thr Gly Leu Phe Lys Gly Asp Lys Cys Gln
 1               5                  10                  15

Ser Leu Val Gly Lys Pro Lys Ile Phe Ile Gln Ala Cys Arg Gly
             20                  25                  30

Ser Gln His Asp Val Pro Val Val Pro Leu Asp Met Val Asp His Gln
         35                  40                  45

Thr Asp Lys
     50

<210> SEQ ID NO 46
<211> LENGTH: 52
<212> TYPE: PRT
<213> ORGANISM: Mus musculus

<400> SEQUENCE: 46

Asn Val Thr Gln Val Asp Ala Ala Ser Val Tyr Thr Leu Pro Ala Gly
 1               5                  10                  15

Ala Asp Phe Leu Met Cys Tyr Ser Val Ala Glu Gly Tyr Tyr Ser His
             20                  25                  30

Arg Glu Thr Val Asn Gly Ser Trp Tyr Ile Gln Asp Leu Cys Glu Met
         35                  40                  45

Leu Ala Arg Tyr
     50

<210> SEQ ID NO 47
<211> LENGTH: 55
<212> TYPE: PRT
<213> ORGANISM: Mus musculus

<400> SEQUENCE: 47

Gly Ser Ser Leu Glu Phe Thr Glu Leu Leu Thr Leu Val Asn Arg Lys
 1               5                  10                  15

Val Ser Gln Arg Arg Val Asp Phe Cys Lys Asp Pro Asp Ala Ile Gly
             20                  25                  30

Lys Lys Gln Val Pro Cys Phe Ala Ser Met Leu Thr Lys Lys Leu His
         35                  40                  45

Phe Cys Pro Lys Pro Ser Lys
     50                  55

<210> SEQ ID NO 48
<211> LENGTH: 250
<212> TYPE: PRT
<213> ORGANISM: Mus musculus

<400> SEQUENCE: 48

Met Asp Phe Gln Ser Cys Leu Asp Ala Ile Ala Glu Glu Leu Gly Ser
 1               5                  10                  15

Glu Asp Leu Ala Ala Leu Lys Phe Leu Cys Leu Asp Tyr Ile Pro His
             20                  25                  30

Lys Lys Leu Glu Thr Ile Glu Asp Ala Gln Lys Leu Phe Leu Arg Leu
         35                  40                  45

Arg Glu Lys Gly Met Leu Glu Glu Gly Asn Leu Ser Phe Leu Lys Glu
     50                  55                  60

Leu Leu Phe His Ile Ser Arg Trp Asp Leu Leu Val Asn Phe Leu Asp
 65                  70                  75                  80

Cys Asn Arg Glu Glu Met Val Arg Glu Leu Arg Asp Pro Arg Gln Cys
                 85                  90                  95
```

```
Pro Arg Phe Leu Pro Tyr Arg Ser Cys Ser Phe Arg Leu Ser Glu Glu
                100                 105                 110

Val Ser Glu Leu Glu Leu Arg Ser Phe Lys Phe Leu Leu Asn Asn Glu
        115                 120                 125

Ile Pro Lys Cys Lys Leu Glu Asp Asp Leu Ser Leu Leu Glu Ile Phe
    130                 135                 140

Val Glu Met Glu Lys Arg Thr Met Leu Ala Glu Asn Asn Leu Glu Thr
145                 150                 155                 160

Leu Lys Ser Ile Cys Asp Gln Val Asn Lys Ser Leu Leu Gly Lys Ile
                165                 170                 175

Glu Asp Tyr Glu Arg Ser Ser Thr Glu Arg Arg Met Ser Leu Glu Gly
        180                 185                 190

Arg Glu Glu Leu Pro Pro Ser Val Leu Asp Glu Met Ser Leu Lys Met
        195                 200                 205

Ala Glu Leu Cys Asp Ser Pro Arg Glu Gln Asp Ser Glu Ser Arg Thr
        210                 215                 220

Ser Asp Lys Val Tyr Gln Met Lys Asn Lys Pro Arg Gly Tyr Cys Leu
225                 230                 235                 240

Ile Ile Asn Asn His Asp Phe Ser Lys Ala
                245                 250

<210> SEQ ID NO 49
<211> LENGTH: 54
<212> TYPE: PRT
<213> ORGANISM: Mus musculus

<400> SEQUENCE: 49

Arg Glu Asp Ile Thr Gln Leu Arg Lys Met Lys Asp Arg Lys Gly Thr
 1               5                  10                  15

Asp Cys Asp Lys Glu Ala Leu Ser Lys Thr Phe Lys Glu Leu His Phe
                20                  25                  30

Glu Ile Val Ser Tyr Asp Asp Cys Thr Ala Asn Glu Ile His Glu Ile
            35                  40                  45

Leu Glu Gly Tyr Gln Ser
    50

<210> SEQ ID NO 50
<211> LENGTH: 28
<212> TYPE: PRT
<213> ORGANISM: Mus musculus

<400> SEQUENCE: 50

Ala Asp His Lys Asn Lys Asp Cys Phe Ile Cys Cys Ile Leu Ser His
 1               5                  10                  15

Gly Asp Lys Gly Val Val Tyr Gly Thr Asp Gly Lys
                20                  25

<210> SEQ ID NO 51
<211> LENGTH: 52
<212> TYPE: PRT
<213> ORGANISM: Mus musculus

<400> SEQUENCE: 51

Glu Ala Ser Ile Tyr Asp Leu Thr Ser Tyr Phe Thr Gly Ser Lys Cys
 1               5                  10                  15

Pro Ser Leu Ser Gly Lys Pro Lys Ile Phe Phe Ile Gln Ala Cys Arg
                20                  25                  30
```

-continued

```
Gly Ser Asn Phe Gln Lys Gly Val Pro Asp Glu Ala Gly Phe Glu Gln
        35                  40                  45

Gln Asn His Thr
    50

<210> SEQ ID NO 52
<211> LENGTH: 47
<212> TYPE: PRT
<213> ORGANISM: Mus musculus

<400> SEQUENCE: 52

Ser Ser His Lys Asn Tyr Ile Pro Asp Glu Ala Asp Phe Leu Leu Gly
 1               5                  10                  15

Met Ala Thr Val Leu Met Cys Val Ser Tyr Arg Asp Pro Val Asn Gly
                20                  25                  30

Thr Trp Tyr Ile Gln Ser Leu Cys Gln Ser Leu Arg Glu Arg Cys
        35                  40                  45

<210> SEQ ID NO 53
<211> LENGTH: 19
<212> TYPE: PRT
<213> ORGANISM: Mus musculus

<400> SEQUENCE: 53

Pro Gln Gly Asp Asp Ile Leu Ser Ile Leu Thr Gly Val Asn Tyr Asp
 1               5                  10                  15

Val Ser Asn

<210> SEQ ID NO 54
<211> LENGTH: 22
<212> TYPE: PRT
<213> ORGANISM: Mus musculus

<400> SEQUENCE: 54

Lys Asp Asp Arg Arg Asn Lys Gly Lys Gln Met Pro Gln Pro Thr Phe
 1               5                  10                  15

Thr Leu Arg Lys Lys Leu
                20

<210> SEQ ID NO 55
<211> LENGTH: 260
<212> TYPE: PRT
<213> ORGANISM: Mus musculus

<400> SEQUENCE: 55

Met Ala Ala Pro Ser Gly Arg Ser Gln Ser Ser Leu His Arg Lys Gly
 1               5                  10                  15

Leu Met Ala Ala Asp Arg Arg Ser Arg Ile Leu Ala Val Cys Gly Met
                20                  25                  30

His Pro Asp His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Gly Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Arg Gln Gly
                100                 105                 110
```

```
His Leu Glu Asp Leu Leu Thr Thr Leu Ser Asp Ile Gln His Val
        115                 120                 125

Leu Pro Pro Leu Ser Cys Asp Tyr Asp Thr Ser Leu Pro Phe Ser Val
130             135                 140

Cys Glu Ser Cys Pro Pro His Lys Gln Leu Arg Leu Ser Thr Asp Ala
145             150                 155                 160

Thr Glu His Ser Leu Asp Asn Gly Asp Gly Pro Pro Cys Leu Leu Val
                165                 170                 175

Lys Pro Cys Thr Pro Glu Phe Tyr Gln Ala His Tyr Gln Leu Ala Tyr
            180                 185                 190

Arg Leu Gln Ser Gln Pro Arg Gly Leu Ala Leu Val Leu Ser Asn Val
        195                 200                 205

His Phe Thr Gly Glu Lys Asp Leu Glu Phe Arg Ser Gly Gly Asp Val
    210                 215                 220

Asp His Thr Thr Leu Val Thr Leu Phe Lys Leu Leu Gly Tyr Asn Val
225                 230                 235                 240

His Val Leu His Asp Gln Thr Ala Gln Glu Met Gln Glu Lys Leu Gln
            245                 250                 255

Asn Phe Ala Gln
            260

<210> SEQ ID NO 56
<211> LENGTH: 11
<212> TYPE: PRT
<213> ORGANISM: Mus musculus

<400> SEQUENCE: 56

Leu Pro Ala His Arg Val Thr Asp Ser Val Cys
1               5                   10

<210> SEQ ID NO 57
<211> LENGTH: 18
<212> TYPE: PRT
<213> ORGANISM: Mus musculus

<400> SEQUENCE: 57

Val Ala Leu Leu Ser His Gly Val Glu Gly Gly Ile Tyr Gly Val Asp
1               5                   10                  15

Gly Lys

<210> SEQ ID NO 58
<211> LENGTH: 56
<212> TYPE: PRT
<213> ORGANISM: Mus musculus

<400> SEQUENCE: 58

Leu Leu Gln Leu Gln Glu Val Phe Arg Leu Phe Asp Asn Ala Asn Cys
1               5                   10                  15

Pro Ser Leu Gln Asn Lys Pro Lys Met Phe Phe Ile Gln Ala Cys Arg
            20                  25                  30

Gly Asp Glu Thr Asp Arg Gly Val Asp Gln Gln Asp Gly Lys Asn His
        35                  40                  45

Thr Gln Ser Pro Gly Cys Glu Glu
    50                  55

<210> SEQ ID NO 59
<211> LENGTH: 53
<212> TYPE: PRT
<213> ORGANISM: Mus musculus
```

```
<400> SEQUENCE: 59

Ser Asp Ala Gly Lys Glu Glu Leu Met Lys Met Arg Leu Pro Thr Arg
 1               5                  10                  15

Ser Asp Met Ile Cys Gly Tyr Ala Cys Leu Lys Gly Asn Ala Ala Met
             20                  25                  30

Arg Asn Thr Lys Arg Gly Ser Trp Tyr Ile Glu Ala Leu Thr Gln Val
         35                  40                  45

Phe Ser Glu Arg Ala
     50

<210> SEQ ID NO 60
<211> LENGTH: 18
<212> TYPE: PRT
<213> ORGANISM: Mus musculus

<400> SEQUENCE: 60

Asp Met His Val Ala Asp Met Leu Val Lys Val Asn Ala Leu Ile Lys
 1               5                  10                  15

Glu Arg

<210> SEQ ID NO 61
<211> LENGTH: 35
<212> TYPE: PRT
<213> ORGANISM: Mus musculus

<400> SEQUENCE: 61

Glu Gly Tyr Ala Pro Gly Thr Glu Phe His Arg Cys Lys Glu Met Ser
 1               5                  10                  15

Glu Tyr Cys Ser Thr Leu Cys Gln Gln Leu Tyr Leu Phe Pro Gly Tyr
             20                  25                  30

Pro Pro Thr
         35

<210> SEQ ID NO 62
<211> LENGTH: 31
<212> TYPE: PRT
<213> ORGANISM: Mus musculus

<400> SEQUENCE: 62

Met Glu Ser Glu Met Ser Asp Pro Gln Pro Leu Gln Glu Glu Arg Tyr
 1               5                  10                  15

Asp Met Ser Gly Ala Arg Leu Ala Leu Thr Leu Cys Val Thr Lys
             20                  25                  30

<210> SEQ ID NO 63
<211> LENGTH: 74
<212> TYPE: PRT
<213> ORGANISM: Mus musculus

<400> SEQUENCE: 63

Ala Arg Glu Gly Ser Glu Val Asp Met Glu Ala Leu Gly Arg Met Phe
 1               5                  10                  15

Arg Tyr Leu Lys Phe Glu Ser Thr Met Lys Arg Asp Pro Thr Ala Gln
             20                  25                  30

Gln Phe Leu Glu Glu Leu Asp Glu Phe Gln Gln Thr Ile Asp Asn Trp
         35                  40                  45

Glu Glu Pro Val Ser Cys Ala Phe Val Val Leu Met Ala His Gly Glu
     50                  55                  60
```

```
Glu Gly Leu Leu Lys Gly Glu Asp Glu Lys
 65                  70
```

<210> SEQ ID NO 64
<211> LENGTH: 56
<212> TYPE: PRT
<213> ORGANISM: Mus musculus

<400> SEQUENCE: 64

```
Met Val Arg Leu Glu Asp Leu Phe Glu Val Leu Asn Asn Lys Asn Cys
 1               5                  10                  15

Lys Ala Leu Arg Gly Lys Pro Lys Val Tyr Ile Ile Gln Ala Cys Arg
                20                  25                  30

Gly Glu His Arg Asp Pro Gly Glu Leu Arg Gly Asn Glu Glu Leu
            35                  40                  45

Gly Gly Asp Glu Glu Leu Gly Gly
        50                  55
```

<210> SEQ ID NO 65
<211> LENGTH: 53
<212> TYPE: PRT
<213> ORGANISM: Mus musculus

<400> SEQUENCE: 65

```
Asp Glu Val Ala Val Leu Lys Asn Asn Pro Gln Ser Ile Pro Thr Tyr
 1               5                  10                  15

Thr Asp Thr Leu His Ile Tyr Ser Thr Val Gly Tyr Leu Ser Tyr
                20                  25                  30

Arg His Asp Glu Lys Gly Ser Gly Phe Ile Gln Thr Leu Thr Asp Val
            35                  40                  45

Phe Ile His Lys Lys
        50
```

<210> SEQ ID NO 66
<211> LENGTH: 15
<212> TYPE: PRT
<213> ORGANISM: Mus musculus

<400> SEQUENCE: 66

```
Ile Leu Glu Leu Thr Glu Glu Ile Thr Arg Leu Met Ala Asn Thr
 1               5                  10                  15
```

<210> SEQ ID NO 67
<211> LENGTH: 8
<212> TYPE: PRT
<213> ORGANISM: Mus musculus

<400> SEQUENCE: 67

```
Glu Val Met Gln Glu Gly Lys Pro
 1               5
```

<210> SEQ ID NO 68
<211> LENGTH: 17
<212> TYPE: PRT
<213> ORGANISM: Mus musculus

<400> SEQUENCE: 68

```
Arg Lys Val Asn Pro Glu Val Gln Ser Thr Leu Arg Lys Lys Leu Tyr
 1               5                  10                  15

Gln
```

<210> SEQ ID NO 69
<211> LENGTH: 21
<212> TYPE: DNA
<213> ORGANISM: Artificial Sequence
<220> FEATURE:
<223> OTHER INFORMATION: Primer derived from mouse caspase-14 cDNA

<400> SEQUENCE: 69
atatgatatg tcaggtgccc g                                              21

<210> SEQ ID NO 70
<211> LENGTH: 19
<212> TYPE: DNA
<213> ORGANISM: Artificial Sequence
<220> FEATURE:
<223> OTHER INFORMATION: Primer derived from mouse caspase-14 cDNA

<400> SEQUENCE: 70
ttccggaggg tgctttgga                                                 19

<210> SEQ ID NO 71
<211> LENGTH: 21
<212> TYPE: DNA
<213> ORGANISM: Artificial Sequence
<220> FEATURE:
<223> OTHER INFORMATION: Primer derived from human caspase-14 cDNA

<400> SEQUENCE: 71
cctgtatgat gtacaccttg g                                              21

<210> SEQ ID NO 72
<211> LENGTH: 19
<212> TYPE: DNA
<213> ORGANISM: Artificial Sequence
<220> FEATURE:
<223> OTHER INFORMATION: Primer derived from human caspase-14 cDNA

<400> SEQUENCE: 72
agagattctc cagcttgac                                                 19

<210> SEQ ID NO 73
<211> LENGTH: 19
<212> TYPE: DNA
<213> ORGANISM: Artificial Sequence
<220> FEATURE:
<223> OTHER INFORMATION: Primer derived from human caspase-14 cDNA

<400> SEQUENCE: 73
atcttctccc ttgaggaag                                                 19

<210> SEQ ID NO 74
<211> LENGTH: 21
<212> TYPE: DNA
<213> ORGANISM: Artificial Sequence
<220> FEATURE:
<223> OTHER INFORMATION: Primer dereived from human caspase-14 cDNA

<400> SEQUENCE: 74
atatgatatg tcaggtgccc g                                              21

<210> SEQ ID NO 75
<211> LENGTH: 20
<212> TYPE: DNA
<213> ORGANISM: Artificial Sequence
<220> FEATURE:
<223> OTHER INFORMATION: Primer derived from human caspase-14 cDNA -continued

```
<400> SEQUENCE: 75
caaggtgtac atcatacagg                                                    20

<210> SEQ ID NO 76
<211> LENGTH: 850
<212> TYPE: DNA
<213> ORGANISM: Mus musculus
<220> FEATURE:
<221> NAME/KEY: modified_base
<222> LOCATION: (537)
<223> OTHER INFORMATION: Where n is Adenine, Cytosine, Guanin or
      Thymidine

<400> SEQUENCE: 76
gtgcgcaggc gggtgcgcag gccactctgt ctccgttttg tttccacgac tttcggtctg         60
tacctcagtc tctactcact aggagtcggt aacgtcctcc tttctatact atacagtcca        120
cgggcggacc gggactgcga cacacagtgg tttcgggccc tcccaaggct ccatctgtac        180
ctccgggacc ttgcgtacaa ggcaatggac tttaaacttt cgtggtactt ctccctaggg        240
tggcgggtcg ttaaagacct tctcaaccta cttaaagtcg tctggtatct attaaccctt        300
ctcggacagt cgacacggaa acaccatgag taccgtgtac cactccttcc ggaggagttc        360
cctcttctac tcttctacca gtctgatctt ctggaaaaac ttcagaactt gttgttcttg        420
acgttccggg actctccgtt cggtttccac atgtagtagg tccgaacatc tcctctcgtg        480
tctctggggc cactccttga tgcacccttta ctccttgatc cacctctact ccttgancca        540
cctctactcc aacgacacga gttcttgttg gggggtttcat agggttggat atgcctatgg        600
gaggtgtaga tgaggtgcca tctccccatg gagaggatat ctgtactgct ctttccgaga        660
ccgaagtagg tctgggactg cctacacaag taagtatttt ttcctaggta gaatcttgac        720
tgtcttctct agtgggctga ataccgtttg tgcctccact acgtccttcc ttttggttcc        780
tttcacttgg gacttcaggt ttcgtgggag gccttcttcg agataaacgt tattttctct        840
cccgtcccta                                                              850

<210> SEQ ID NO 77
<211> LENGTH: 16
<212> TYPE: PRT
<213> ORGANISM: Mus musculus

<400> SEQUENCE: 77

His Ala Ser Ala His Ala Ser Gly Glu Thr Glu Ala Lys Gln Arg Cys
  1               5                  10                  15

<210> SEQ ID NO 78
<211> LENGTH: 5
<212> TYPE: PRT
<213> ORGANISM: Mus musculus

<400> SEQUENCE: 78

Lys Arg Gly Gln Gly
  1               5
```

We claim:

1. An isolate caspase-14 polypeptide, comprising SEQ ID NO:5.

2. The polypeptide of claim 1 comprising a large subunit of caspase-14.

3. The polypeptide of claim 1 comprising a small subunit of caspase-14.

4. An isolated polypeptide, consisting of amino acid sequences selected from the group consisting of positions 1 to 146 of SEQ ID NO:5, positions 1–146 of SEQ ID NO:7, and positions 1–118 of SEQ ID NO:9.

5. An isolated polypeptide, consisting of amino acid sequences selected from the group consisting of positions 147 to 242 of SEQ ID NO:5, positions 147–230 of SEQ ID NO:7, and positions 119–214 of SEQ ID NO:9.

6. An isolated polypeptide, comprising the polypeptide sequence of SEQ ID NO:7.

7. An isolated polypeptide, comprising the polypeptide sequence of SEQ ID NO:9.

8. An isolated human caspase-14 polypeptide having greater than 80% amino acid identity with either SEQ ID Nos: 2 or 5, wherein said polypeptide retains caspase protease activity.

9. An isolated polypeptide, comprising SEQ ID NO:2.

10. An isolated polypeptide, consisting of positions 1 to 156 of SEQ ID NO:2.

11. An isolated polypeptide, consisting of positions 163 to 257 of SEQ ID NO:2.

* * * * *